(12) United States Patent
Kameli

(10) Patent No.: US 9,144,686 B2
(45) Date of Patent: Sep. 29, 2015

(54) IMPLANTABLE MEDICAL DEVICE WITH EXTERNAL ACCESS FOR RECHARGING AND DATA COMMUNICATION

(75) Inventor: Nader Kameli, Hugo, MN (US)

(73) Assignee: Neurocardiac Innovations, LLC, Hugo, MN (US)

( * ) Notice: Subject to any disclaimer, the term of this patent is extended or adjusted under 35 U.S.C. 154(b) by 1040 days.

(21) Appl. No.: 13/011,820

(22) Filed: Jan. 21, 2011

(65) Prior Publication Data

US 2012/0190969 A1     Jul. 26, 2012

(51) Int. Cl.
| | |
|---|---|
| *A61N 1/00* | (2006.01) |
| *A61N 1/37* | (2006.01) |
| *A61N 1/375* | (2006.01) |
| *A61M 5/50* | (2006.01) |
| *A61N 1/05* | (2006.01) |
| *A61N 1/365* | (2006.01) |
| *A61N 1/372* | (2006.01) |

(Continued)

(52) U.S. Cl.
CPC ............... *A61N 1/3706* (2013.01); *A61M 5/50* (2013.01); *A61N 1/378* (2013.01); *A61N 1/3752* (2013.01); *A61N 1/3968* (2013.01); *A61M 2230/62* (2013.01); *A61N 1/056* (2013.01); *A61N 1/36535* (2013.01); *A61N 1/3787* (2013.01); *A61N 1/37288* (2013.01); *A61N 1/3962* (2013.01)

(58) Field of Classification Search
CPC ... A61N 1/375; A61N 1/3787; A61N 1/3962; A61N 1/3752; A61M 2330/62
USPC .................................................. 607/2, 36, 37
See application file for complete search history.

(56) References Cited

U.S. PATENT DOCUMENTS

| | | | |
|---|---|---|---|
| 3,867,950 | A | 2/1975 | Fischell |
| 5,411,538 | A | 5/1995 | Lin |
| 5,464,434 | A | 11/1995 | Alt |

(Continued)

FOREIGN PATENT DOCUMENTS

EP     2 008 581 A2     12/2008

OTHER PUBLICATIONS

Partial Search Report of European Application No. 12151935.9 dated May 16, 2012 (6 pages).

(Continued)

*Primary Examiner* — Christopher D Koharski
*Assistant Examiner* — Roland Dinga
(74) *Attorney, Agent, or Firm* — McDonnell Boehnen Hulbert & Berghoff LLP

(57) ABSTRACT

Embodiments relate to an implantable cardiac system, including a housing, electronic circuitry for controlling one or more of power management, processing unit, information memory and management circuit, sensing and simulation output. The system also includes diagnosis and treatment software for diagnosing health issues, diagnosing mechanical issues, determining therapy output and manage patient health indicators over time, a power supply system including at least one rechargeable battery, a recharging system, an alarm (or alert) system to inform patient of energy level and integrity of system, communication circuitry, one or more electrodes for delivering therapeutic signal to a heart and one or more electrodes for from delivering electrocardiogram signal from the heart to the electronic circuitry. The power sources can include rechargeable batteries. The housing can include receptacles that receive a probe that mechanically and electrically connects to circuitry to recharge the device and receive data from the device.

30 Claims, 28 Drawing Sheets

(51) Int. Cl.
*A61N 1/378* (2006.01)
*A61N 1/39* (2006.01)

(56) References Cited

U.S. PATENT DOCUMENTS

| | | | |
|---|---|---|---|
| 5,556,421 A * | 9/1996 | Prutchi et al. | 607/36 |
| 5,593,428 A * | 1/1997 | Jamshidi | 607/10 |
| 5,865,760 A | 2/1999 | Lidman | |
| 6,044,297 A | 3/2000 | Sheldon et al. | |
| 6,760,625 B1 | 7/2004 | Kroll | |
| 7,203,547 B1 | 4/2007 | Kroll | |
| 7,295,878 B1 | 11/2007 | Meadows | |
| 7,899,537 B1 | 3/2011 | Kroll | |
| 8,219,196 B2 | 7/2012 | Torgerson | |
| 8,244,367 B2 | 8/2012 | Wahlstrand | |
| 2002/0099422 A1 | 7/2002 | Ferek-Petric | |
| 2003/0040778 A1 | 2/2003 | Kroll et al. | |
| 2004/0225333 A1 | 11/2004 | Greatbatch | |
| 2005/0043652 A1 | 2/2005 | Lovett et al. | |
| 2005/0145246 A1 | 7/2005 | Hartley | |
| 2007/0040687 A1 | 2/2007 | Reynolds | |
| 2007/0179539 A1 | 8/2007 | Degroot | |
| 2009/0171228 A1 | 7/2009 | Frischell | |
| 2009/0182388 A1 | 7/2009 | VonArx | |
| 2010/0049063 A1 | 2/2010 | Dobak, III | |
| 2010/0113889 A1 | 5/2010 | Ghanen | |
| 2010/0274230 A1 * | 10/2010 | Edgell et al. | 606/1 |
| 2010/0331924 A1 * | 12/2010 | North | 607/72 |

OTHER PUBLICATIONS

Communication pursuant to Article 94(3) issued in European Patent Application No. 12 151 935.9 on Aug. 13, 2013, 4 pages.

* cited by examiner

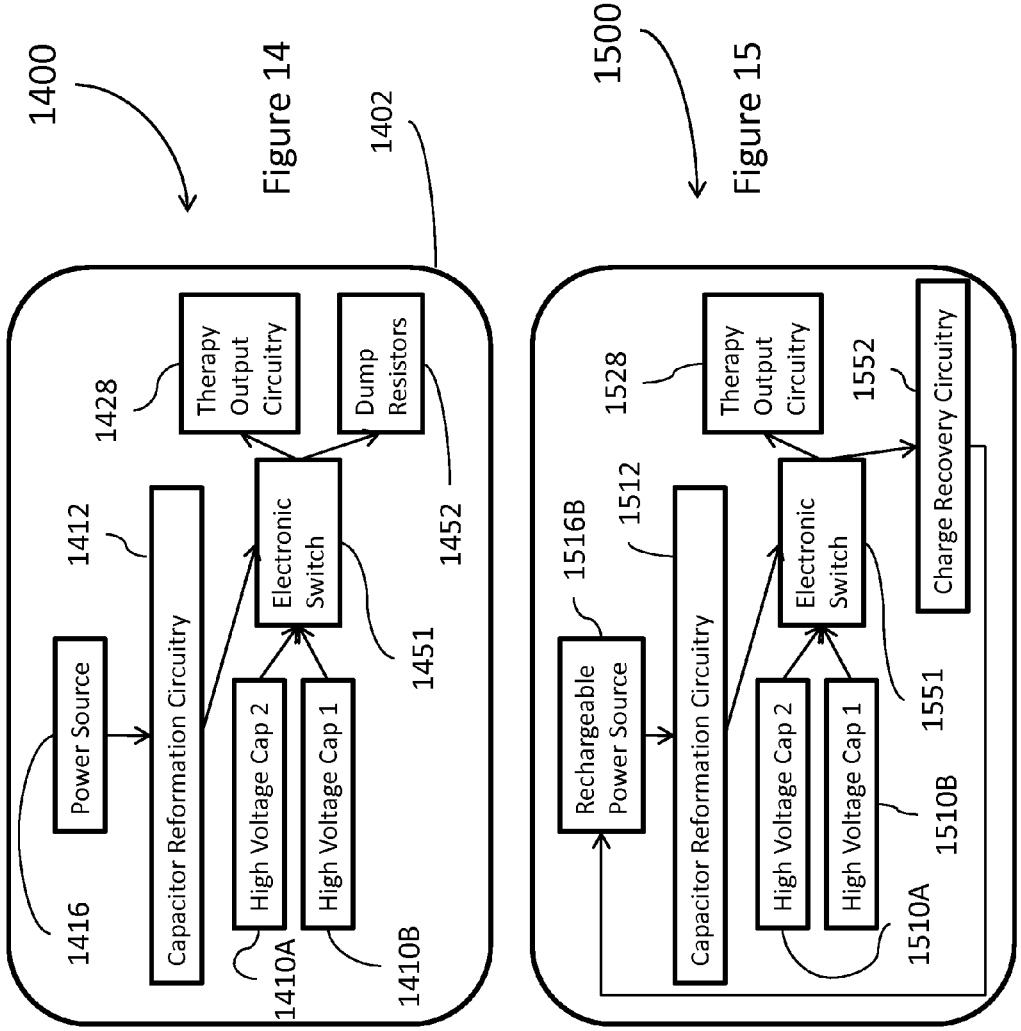

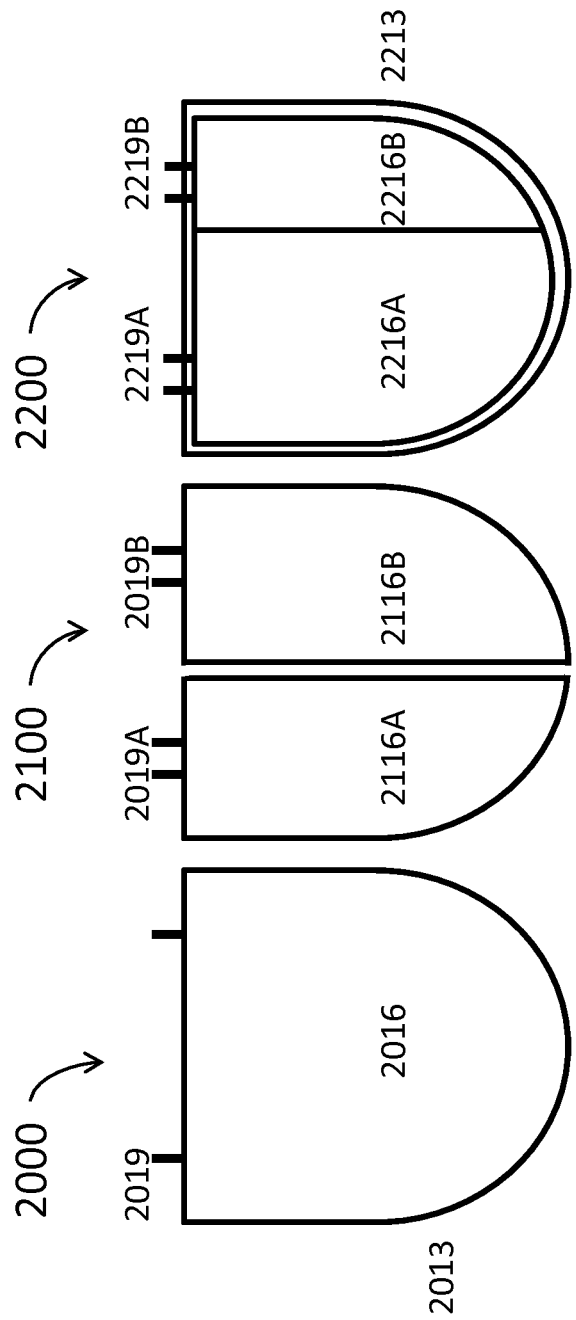

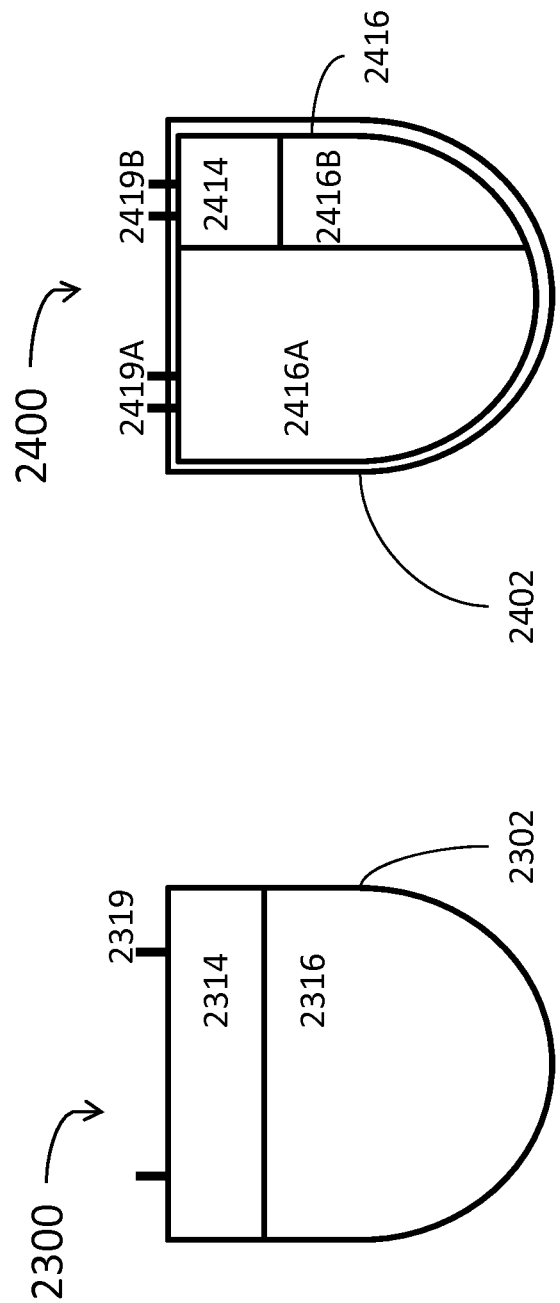

IMPLANTABLE MEDICAL DEVICE WITH EXTERNAL ACCESS FOR RECHARGING AND DATA COMMUNICATION

BACKGROUND

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachyarrythmia. Tachyarrythmia may have its origin in either the atria or the ventricles. Tachyarrythmias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachyarrythmia occurs, for example, when electrical activity arises in the ventricular myocardium at a rate more rapid than the normal sinus rhythm. Ventricular tachyarrythmia includes ventricular tachycardia and ventricular fibrillation. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

In late 1980s, studies identified groups of patients that could benefit from the use of implantable cardiac defibrillators (ICDs). Implantation of ICDs became the medical standard of care for those patients determined to have the indicated level of health risks.

Over time, post market studies have identified a large group of patients who would meet the determined risk levels, but will not receive benefits from these devices in the immediate years. Therefore, such patients would receive an ICD and the device would stay in the body for a long time without ever firing or shocking the patient's heart. The current devices are designed to address complex arrhythmias and implantation of them in the initial group of patients is deemed as unnecessary, and economically irresponsible. Thousands of patients are given devices that treat more than they are at risk for, as the current devices on the market are developed to treat and handle a multitude of cardiac conditions. Additionally, the devices require a specialist to implant and often need a programmer or consultant to initially program the device.

ICDs are utilized more frequently as prophylactic devices for treatment of sudden cardiac death (SCD). In addition to implantable devices, automated external defibrillators (AEDs) are also effective in treatment of SCD but require administration of the therapy by an outside agent (such as a bystander). As long as the AED treatment is given to the patient within the first 2-3 minutes from the onset of the event, the patient will likely have a positive response to the treatment. Studies have shown that more than 75% of the SCDs occur at home and over half occur in the bedroom. Patients at risk of SCD are often alone and asleep and would need their safety product nearby and not rely on the help of a third party.

SUMMARY

Embodiments of the present disclosure relate to an implantable cardiac system, including at least one housing, electronic circuitry for controlling one or more of power management, processing unit, information memory and management circuitry, sensing and simulation output. The system can also include a means to determine the position of the patient, e.g., a patient position sensor. The position information can be information used to diagnose the patient and/or determine operation of the system. The system can also include diagnosis and treatment software (algorithms and instructions stored in a machine readable format) for diagnosing health issues, diagnosing mechanical/electrical issues in the system, determining therapy output and manage patient health indicators over time, a power supply system including at least one rechargeable battery, a recharging system, an alarm system to inform patient of energy level and integrity of system, communication circuitry, one or more electrodes for delivering therapeutic signal to a heart and one or more electrodes for delivering electrocardiogram signal from the heart and other physiological signals to the electronic circuitry.

An embodiment includes one or more cardiac sensors to detect a cardiac episode and outputting cardiac data, a body orientation unit to determine an orientation of a body and to output orientation data, and therapy circuitry to apply cardiac therapy using the cardiac data and the orientation data. In an aspect, the body orientation unit includes an accelerometer. In an aspect, the accelerometer includes at least one of a capacitive device, a MEMS device, a plurality of two-axis devices, a single three-axis device, and a six-axis device, which are to output a signal indicative of an orientation of a patient. In an aspect, the body orientation unit includes an inclinometer. In an aspect, the inclinometer includes at least one of a capacitive device and a MEMS device, which can output a signal indicative of an orientation of a patient. In an aspect, the body orientation unit includes a gyrometer. In an aspect, the gyrometer includes at least one of a MEMS device and a three-axis device, which can output a signal indicative of an orientation of a patient. In an aspect, the therapy circuitry is to deliver only a defibrillation signal. In an aspect, the therapy circuitry is free from pacing determinations and is free from delivering pacing signals.

The embodiments and aspects described herein can further include a housing to be implantable and essentially biologically inert in a body of a person. In an aspect, the housing can enclose cardiac detection circuitry to detect a cardiac episode and cardiac therapy circuitry to deliver a cardiac therapy signal. In an aspect, the housing can enclose the body orientation unit to determine an orientation of a body, wherein the body orientation unit is to control delivery of the cardiac therapy signal to a heart when the body orientation unit determines that the orientation is essentially vertical. In an aspect, the body orientation unit is to allow delivery of the therapy signal to a heart with the orientation being essentially horizontal. The body orientation unit can include at least one of an accelerometer, an inclinometer, or a gyrometer. In an aspect, the cardiac therapy circuitry includes a processor to receive orientation data from the body orientation unit and to control delivery of a defibrillation signal to the heart. In an aspect, the cardiac therapy circuitry includes one or more capacitors to supply energy for a defibrillation signal and capacity reformation circuitry. In an aspect, the cardiac detection circuitry includes sensors to connect to leads, the sensors to analyze a heart signal and indicate an abnormal heart rhythm. In an aspect, the housing includes a data storage system in the housing to store device performance data and patient related data. In an aspect the housing includes a plurality of distinct housings, which can store different circuitry or components of the implant device in respective housings. In an aspect, one housing can store a primary battery and another housing stores a rechargeable battery.

BRIEF DESCRIPTION OF THE DRAWINGS

The accompanying drawings illustrate non-limiting example embodiments of the invention.

FIGS. 14-19 show various schematic views of an implantable device for treating a patient at risk for a cardiac episode, according to some embodiments.

FIGS. 20-22 show schematic views for packaging power sources for implantable medical devices, according to some embodiments.

FIGS. 23-24 show schematic views for packaging power sources for implantable medical devices, according to some embodiments.

DETAILED DESCRIPTION

Figure 1:
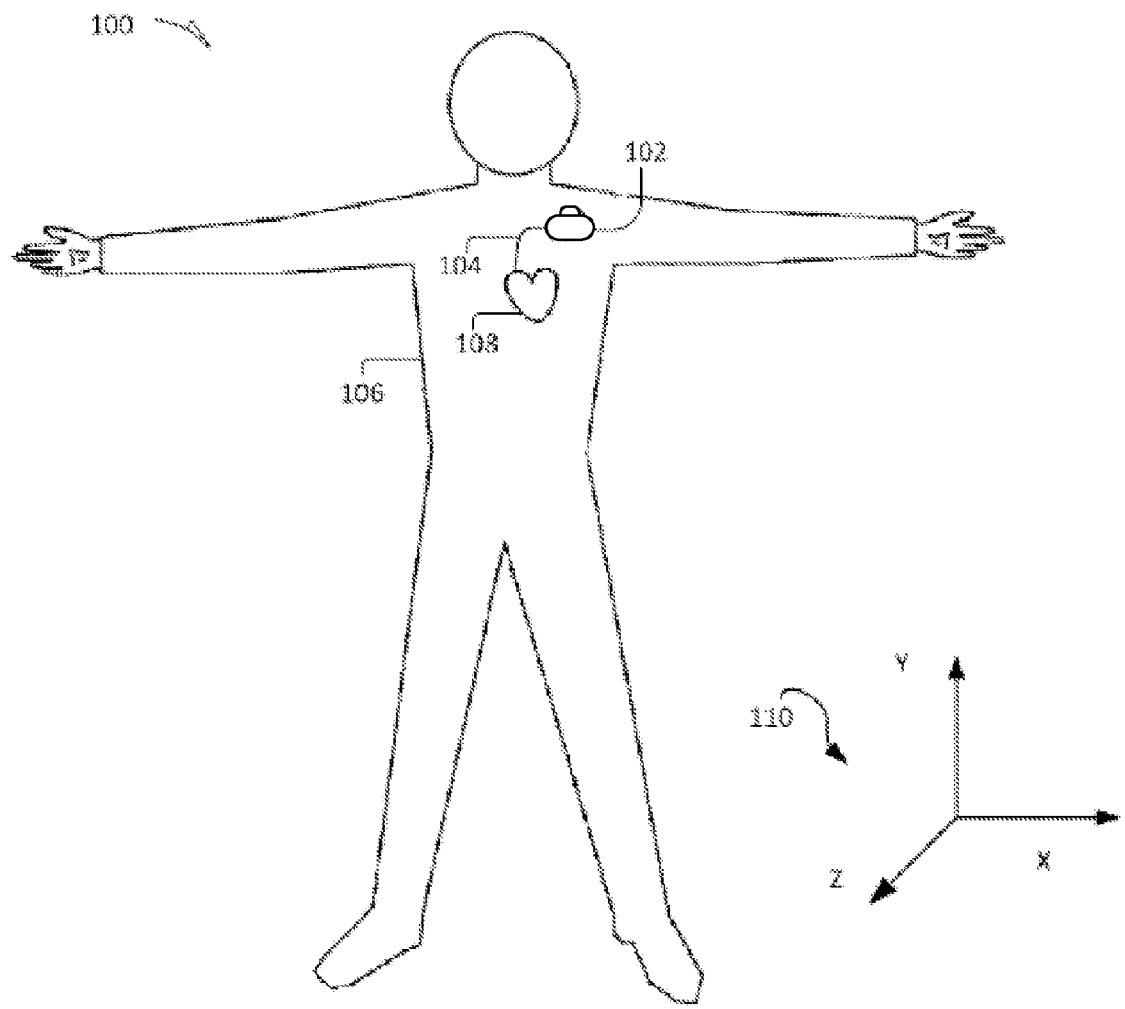
FIG. 1 is a schematic view of an implantable device system within a patient, according to some embodiments.

Throughout the following description, specific details are set forth in order to provide a more thorough understanding of the invention. However, the invention may be practiced without these particulars. In other instances, well known elements have not been shown or described in detail in order to avoid unnecessarily obscuring the invention. The drawings show, by way of illustration, specific embodiments in which the invention may be practiced. These embodiments may be combined, other elements may be utilized or structural or logical changes may be made without departing from the scope of the invention. Accordingly, the specification and drawings are to be regarded in an illustrative, rather than a restrictive, sense.

All publications, patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more". In this document, the term "or" is used to refer to a nonexclusive or, such that "A, B or C" includes "A only", "B only", "C only", "A and B", "B and C", "A and C", and "A, B and C", unless otherwise indicated. In the appended aspects or claims, the terms "first", "second" and "third", etc. are used merely as labels, and are not intended to impose numerical requirements on their objects.

Overview

Embodiments of the present relate to an implantable cardiac defibrillator (ICD) and methods of treating a patient. Currently, there is no stratification in risk levels of cardiac patients for conditions or events such as sudden cardiac arrest (SCA), ventricular fibrillation (VF) and/or ventricular tachycardia (VT), all of which could result in sudden cardiac death (SCD), when determining the implantation of an ICD. If a patient meets the minimum threshold of risk level, they are considered for a "full-featured" implantable device that often includes expensive and unnecessary options for a particular patient, e.g., both pacing and defibrillation features. According to the embodiments of the present invention, a stratification system of evaluation and diagnosis has be developed that identifies patients at higher risk later in the progression cycle of the disease and addresses each patient appropriately with the therapeutic implantable device for the individual patient as opposed to placing the patient in a group that receives only a more expensive option. Those patients in the lower tiers of risk may be outfitted with a simpler, less expensive device that can treat a first cardiac episode within a patient to protect the patient from a potentially fatal cardiac episode. The device can optionally relay further information to a medical professional to more fully evaluate the medical status of the patient and determine the patient's therapeutic needs. The evaluation may recategorize the patient for a different device or cause the medical care provider to change the device. Embodiments of the present invention provide not only a device and method of treatment, but a system for delivering the right product to the right patient at the right time. This approach saves money, saves time and treats the patient's needs in a more efficient way. Additionally, approaches described herein allow the natural system of the human body to take its course and help it recover as much as possible. That is, the present methods and device can assist the body in recovering from a potentially fatal event in a minimally intrusive manner. In an example, the methods and devices can apply a therapy and then wait for the body to respond to the therapy. In some instances the therapy according to the methods and devices herein are complementary to other therapy or therapies. While in some instances drug therapy may be used, the time limitations on drug therapies, e.g., diagnosis and having a therapeutically effective amount at the location in the body at the proper time, may not provide the life saving effect needed if the person is not already on drug therapy or the drug therapy is not effective for that individual. Moreover, as the medical provider, e.g., a cardiologist, treats the heart with medicine to try to assist the natural system of the body to recover from the disease, the patient is still at risk of unexpected events that would result in death. The method and therapy provided by the present disclosure can allow physicians to pursue normal course of treatment with benefit of system that protects the patient against unexpected death events. Such approach will allow medical therapy to treat the disease and not use device therapy only to address events or by-products of the disease.

A current standard of care in medicine will be used to identify patients who indicate (meet the medical threshold for risk) for ICDs. These patients can be generally divided into two groups. The primary prevention group, which has all the indications of being at risk, but has had no incident. The secondary prevention group has already had an event and could be at risk for a second event or subsequent events. The primary group of patients may receive a prophylactic device that is capable of addressing VF that would result in SCD. This device may be augmented with medication to address other needs that the patient may have such as occasional VT.

Studies have shown that patients, who have been identified as indicated for a device, may not receive an implantable device until, on average, 2 years from the indication. Such a delay is part of the current standard of care because device therapy is used as the last resort even though it is essential for protection against sudden death. Cardiologists typically apply conventional standard of care, which includes drug therapy, to help in recovery of the heart and stop of progression of disease. Cardiologists believe that general electrical therapy provided by most devices, in addition to their defibrillation therapy, is not as effective in treating the disease as proven medical (i.e., drug) therapy. Though this may be true of some types of electrical therapy, it is not of defibrillation therapy. Since conventional devices deliver all therapeutic solutions in one package, they all are rejected in one decision by the cardiologist. It is a fact that patients, who are undergoing drug therapy under the care of a cardiologist, could benefit from defibrillation protection that only devices can offer, in the event of a VF or SCD.

The present disclosure describes devices and methods using the need for implantation of a prophylactic device which provides defibrillation therapy-only as soon as patient is indicated at risk. During this period, physicians can use conventional therapy, in conjunction with the device, to treat the patient and try to stop the progression of the patient's disease. Such an approach will give the patients the protection they need, and give the physician more time to treat the patient with ease of mind and hopefully with an improvement in outcomes.

When ICDs were developed over 20 years ago, they were implemented with batteries that resulted in few short years of service prior to complete depletion and generate a need for replacement. Due to battery limitations, the electronics in most all cases outlasted the battery life. Devices were typically implanted in patients and were left implanted in the patient until the battery ran out, indicating a need for replacement. This process worked fine when the battery life was shorter than the life of the electronics. But as battery life increases, it is possible for electronics to fail before the battery. Such failures can result in catastrophic events that leave the patient unprotected. Over the past 20 years, the battery technology has improved allowing the batteries to hold more energy for a longer period of time, and the ICD electronics have improved to consume less energy to operate. These improvements have caused the batteries in some cases to outlast the electronics. Even though the life of a battery is dependent on the energy consumptions level over time, the life of the electronics are typically more a function of time. The increased in longevity of batteries has caused increased reliability concerns with the electronics in implanted medical devices. As electronics have a finite reliable lifetime, the present inventor has recognized the need to consider the overall system in calculation and designation of reliable operating period of the medical implant. Once this reliable period is ended, the device should be replaced to ensure ongoing protection for the patient without undue risk of component and electronics failure. Unfortunately, current medical devices, e.g., an implanted medical device, are still relying on battery depletion to be the indication for replacement of the device. In an example of the present embodiments devices described herein can have an expiration date. The date is calculated, tested and validated through design and development to ensure proper operation of the device during its intended operating period.

Embodiments of the present disclosure allow use of internal electronic circuitry that will terminate the function of the device at a set time or a predetermined time. This termination function will render the device inoperative for output and manipulation of the patient. That is, the device cannot provide medical therapy. This is done to protect the patient from misoperation that could result from a device that has exceeded its reliably useful period. In one embodiment, the internal electronic circuitry of the device includes a fuse or other forms of electronics that act similar to a fuse, which is placed at the output of the device. When the expiration time is reached, the internal electronic circuitry of the device causes the fuse to discontinue the electrical connection that delivers therapy to the electrodes (e.g., outputs a therapy signal from the device). In this embodiment, the device will have sensing and monitoring connection with the heart, but will not have the ability to delivery therapy. Though the termination function will permanently terminate therapeutic output of the device, it can optionally maintain monitoring and storage capabilities to allow a physician access to all physiological events and facts as observed by the device. When such a termination function is activated, the device outputs a notification signal, e.g., to the patient, that the expiration time has been reached or passed. In an example, the termination function can be in the form of a fuse or other signal blocking circuitry to activate the termination function.

In another embodiment, a fuse or other forms of electronics, which act similar to a fuse, is placed at the supply of energy to the signal processing circuitry of the device. Once the expiration date is reached, the fuse is moved to an open circuit position, e.g., physically burned through, to terminate the application of power to the signal processing electronics, leaving this section inoperative.

In another embodiment, the circuitry is unchanged and the instructions stored in the device (e.g., internal software on a machine readable media) are used to disable operation and control of the signal processing, thereby preventing any therapy to be delivered from the device. In this method, the device is fully operational, but the software has prevented its therapy operation to ensure safety of the patient.

As such termination of service will leave the patient unprotected with regard to sudden cardiac death events, embodiment of the present disclosure allows for various methods of alarming the patient and optionally the physician of imminence of such expiration date and gives them ample time to plan replacement procedure. In one embodiment, the device has an internal sound generator or buzzer. The buzzer is attached to, or is in close proximity of the device shell to allow for better delivery of sound outside the device housing. The buzzer is used to alarm the patient of various issues and notes. In the event the device has reached or is close to reaching replacement time, the device uses the internal alerting mechanism to inform the patient by sending periodic alarms to them. Since alarms and internal sounds are disruptive to rest time, the internal body position sensor is used to decide when to deliver the alarm. For example, in the event the alarm is not critical, the device only delivers the alarm when the patient is vertical and moving, and stays quiet during rest time when the body is horizontal.

The prophylactic device will be implemented with a fixed life, such for a period of years, e.g. more than three years, less than or equal to about 10 years, or 5 years. The fixed life can be stored in the device. In an example, the fixed life will provide sufficient time for a drug therapy to be applied and run its course to determine its efficacy for the patient. During this period the device will provide SCD protection in case the patient needs it. Should the patient recover sufficiently such that the patient's health status indicates that the implanted device is no longer needed, then the need for replacement is eliminated. In an example, the device will have a secondary termination mechanism. The device is designed to only support the patient for a limited time, for example 1 month, since the first successful rescue from a SCD event. The device, in this example, is designed to be a protection mechanism for patients who are at risk, but have not exhibited the need for an ongoing ICD protection. Once an episode of SCD is experienced and patient successfully recovered, the patient is then at risk for ongoing events and needs to be supported for a longer period of time.

The prophylactic device has the ability to store information about the event and present it to the physician for medical analysis, e.g., root cause analysis and further event diagnosis. After the first successful rescue, the physician has the role of diagnosing patient's need and prescribing the appropriate device, which can be at least partially based on the data from the device.

Should the patient have a need for protection against complex arrhythmias or more sophisticated care, as diagnosed by the physician, a more capable device with all the available features to program and customize to the need of the patient is chosen. Examples of some current more capable devices can include the COGNIS™ defibrillator or CONTAK RENEWAL™ pacemaker both by Boston Scientific of Natick, Mass. ADAPTA® Pacing System, VIRTUOSO® device and CONCERTO® device, these three by Medtronic of Minneapolis, Minn.

In the event that the patient needs an ongoing protection against SCD and does not have any other known and preventable issues that can be supported by an electronic medical device, then the physician has the choice of replacing the prophylactic, short life device, with a rechargeable long life device. In an aspect with multiple housings, the housing with a battery can be replaced with the other housing, which can be attached to the leads, remains in place in the patient.

The rechargeable device will have a limited life, for example, 10 years or less than 15 years, and can provide defibrillation support for the patients as many times and as much as they need. Such a device would include extended life circuitry relative to some current full therapy implantable devices. The present device has enough energy to last the reliable life of the electronics, and can be charged as many times as the patients needs it if the physician determines that this device and therapy it can deliver is in the best interests of the patient. Given the life saving nature of the present devices and methods, the charging should not be left to the patient. Should the patient forget, or chose to ignore the need, they will be left unprotected. Additionally, given the large battery size, charging using conventional inductive methods would requires hours or days of charge time which impractical and unreliable. The present invention has a method and system that allows the rechargeable device to be charged in office by physicians and using a method of direct connect (e.g., a mechanical connection to flow electrical energy to the battery) that allows the charging mechanism to be plugged to the device to transfer charge. Such approach will allow a fast charge time for the rechargeable battery and safer overall operation of the process by ensuring proper procedure and outcome.

Using embodiments of the present disclosure, the device has a built-in receptacle to mate with a charging probe. The receptacle can be utilized in various designs as needed for each implant application. In an embodiment, the receptacle is part of the header of the device, which header is attached to the housing of the device. The receptacle is a recess with an opening that allows entry of the probe. This opening is covered by a membrane that prevents fluid, e.g., bodily fluid, from entering remainder of the receptacle and the housing. The outside circumference of the entry is marked with opaque material that is easy to see via medical imaging, e.g., x-ray or fluoroscopy imaging system. This marker is used by physicians during the procedure to guide the probe to the right place for mating with the device.

Inside the receptacle, there are various conductive connectors that can make connection to various portions of the probe to form a complete electrical connection. At the bottom of the receptacle there is a switch that allows activation of the electrical connectors. In order to prevent misoperation from misalignment of the electrical connectors with the wrong portion of the probe, the connectors stay inactive until the entire probe is inserted. Once the probe reaches the end, it will press on the switch placed at the bottom of the receptacle and activate the electrical connection between the electronic circuitry inside the device and the probe. At that time the outside charging circuitry and the inside electronic circuitry will have formed a complete electrical connection and the outside system can communicate and deliver energy to the inside electronic circuitry.

Upon completion of charging, the probe is pulled away from the device. The removal of the probe from the receptacle causes termination of electrical connection by releasing the end of the receptacle switch. As the probe is pulled out of the receptacle completely, the membrane at the entry to the receptacle closes the open end of the receptacle with tightly forming a seal and preventing any liquid from leaking into the receptacle.

In an embodiment, the entry into the receptacle is protected by two layers of membrane with glue-like polymer or chemical inside that is body friendly (e.g., bio-compatible) and is biomimetic. The membrane with multiple layers of forms reservoir(s). This reservoir(s) is used to trap any of body fluid leaked in to the receptacle. Upon the removal of the probe from the receptacle, the glue-like polymer from the inside reservoir will leak to the outside prior to the closing of the hole by the pressure of the membranes. In an example, glue-like polymer is body fluid activated and forms a seal on the membrane where the probe was extracted.

This probe is used to pierce through the skin of the patient and connect with the device. This design allows smaller hole in the receptacle membrane and thereby reducing risk of potential fluid leak. Some previous probe designs have multiple layers with each layer tapered along the shaft of the probe with each distal layer being smaller than the one proximal to it. Such design increases the size of the hole needed to puncture the membrane as the tip of the probe is smaller than the end of the probe. Using such design, when the probe is pulled out, leaves large hole in place around the shaft of the probe allowing liquid to seep in from around the probe. The current design improves on this approach by providing a probe that is uniform from top to the tip reducing the possibility for fluid to seep in. Additionally, the current design requires smaller hole for insertion, resulting in smaller and more compact receptacle and a uniformly created hole that is easier to manage for fast and complete closure.

Once the connection is made, the device and the charger are in direct contact though a highly conductive medium, i.e., the probe and conductors in the receptacle. This probe and method of direct connection will allow the outside charger to deliver large amounts of charge, in a faster manner to the battery in order to replenish it and bring it up to full charge. In one embodiment, the device has a battery chemistry that would allow the charge time to be less than 10 minutes in office as opposed to 20 hours at home. Obviously this approach is more convenient, realistic (compliance by patient more likely), and patient friendly.

Given the need for piercing the skin in order to mate with the device, this procedure will have to be done in a medical office. The need to perform this procedure in office, will ensure proper supervision of a physician and a technician that would guarantee the result. Such method of intervention by experts and specialists will remove the issue of patient compliance and ensure that the device is available to the patient at all times.

Once the present, prophylactic device correctly rescues the patient from an episode of SCD, that patient may then be a candidate for a more full-featured device that can provide ongoing therapy without compromise, and specific to the needs of that patient. At that point the prophylactic device may be removed and then is replaced by more capable and longer lasting device.

During the initial phase of therapy, a cardiac patient is under the care of a cardiologist. The prophylactic device acts as insurance against sudden cardiac events. It additionally gives the physician time to apply drug therapy and behavioral therapy to assist the patient in reversing or retarding the progression of the disease. Once an episode of SCD has been experienced, the patient is not at risk, but is proven to be in need. At that point the physician has the option among many device alternatives available to them. If the patient is still progressing nicely with drug therapy and is on the path to recovery, a longer lasting ICD with basic defibrillation capability, e.g., the present device, could be the right choice for a particular patient. On the other hand, if the patient has shown complications in their cardiac rhythm and require different algorithmic support, the use of prophylactic device will provide them a better tool with additional information and data to properly select the right product from the pool of products available from a variety of pacing and ICD device manufacturers, e.g., COGNIS™ defibrillator or CONTAK RENEWAL™ pacemaker both by Boston Scientific of Natick, Mass. or ADAPTA® Pacing System, VIRTUOSO® device and CONCERTO® device, these three by Medtronic of Minneapolis, Minn. Additionally, the information and data from the prophylactic device can be used to better program the algorithms and features of the replacement device used in place of the device of the present disclosure.

Given that a device with a rechargeable device can have a longer life than a conventional ICD with a non-rechargeable battery, the physician has a choice between these two types of devices. If the benefit of a longer life device that can provide basic protection against SCD is what the patient needs, the physician can chose the rechargeable device of the present disclosure and perhaps reduce the number of additional surgeries that would be required for replacement of conventional ICD over time. On the other hand, if the patient needs the complicated rhythmic support, the physician can chose from other devices and provide the appropriate support for the patient.

Devices and systems described in greater detail herein use a plurality of housings to encase various components of the implantable device. The use of multiple housings can allow the implant of a smaller device in more difficult implant locations and a larger device in a more convenient implant location in the patient's body. In an example, a first implantable housing is adjacent the patient's heart. A second implantable housing is remote from the chest cavity. The first and second housings can be in electrical communication over an implanted line, e.g., an electrical line similar to a cardiac lead that has two connectors instead of a connector and an electrode. The second housing can be near the skin for access in the rechargeable embodiments described herein. The second housing can include a greater battery capacity that conventional pacing implants as it is not implanted in the chest cavity.

Definitions

As used herein, "cardiac episode" or "cardiac event" refers to a detectable abnormality in heart function or an abnormality that may affect the heart. Examples of a cardiac episode or event include sudden cardiac death (SCD), ventricular fibrillation (VF) or ventricular tachycardia (VT).

As used herein, "cardiac prophylactic device" refers to a device including at least one function intended to prevent a cardiac episode or treat a patient after a cardiac episode sufficient for the patient to seek further medical attention. For example, a cardiac prophylactic device may be utilized for limited defibrillation in order to treat a patient after a single cardiac episode.

As used herein, "implanting" refers to inserting or embedding a medical device surgically. Implanting may include partial implantation, for example.

As used herein, "shocking" refers to a therapeutic dose of electrical energy delivered to at least a portion of the heart.

As used herein, "removing" refers to dissociating a medical device from a patient. Examples include surgically removing a device from implantation near the heart of a patient.

As used herein, "contacting" refers to electrically, mechanically, physically or chemically associating two or more components. The two components may be connected (e.g., mechanically or electrically) or in close proximity, for example.

As used herein, "replacement device" or "replacement cardiac device" refers to a medical device utilized after the use of a first device has discontinued. The replacement device may include the same or more features as the first device, for example. A replacement device for cardiac patients may be a full-featured ICD or alternatively include pacemaking functions.

As used herein, "evaluating" refers to testing and monitoring by a health care professional or doctor of a patient in order to assess likelihood of potential cardiac problems. Factors that contribute to a level of increased risk include smoking, high blood pressure, weight, diabetes and high cholesterol. Tests, such as blood tests, may be performed by those skilled in the art in order to assess such risk.

As used herein, "level of risk" refers to the likelihood of a patient suffering one or more cardiac episodes. Traditionally, once a health care professional determines there is even the slightest level of risk that a threshold has been crossed, a patient may be eligible or recommended for an implantable cardiac device. Often, such devices include features beyond what the patient may ever utilize or be at risk for. A "one size fits all" approach has been conventionally used. According to the embodiments of the present invention, a tiered or stratification of risk levels may be formed in order to treat the patient with a device more customized or suitable for their level of risk.

As used herein, "cardiac death (SCD)" refers to death resulting from an abrupt loss of heart function (cardiac arrest). The victim may or may not have diagnosed heart disease. The time and mode of death are unexpected. It may occur within minutes after symptoms appear. The most common underlying reason for patients to die suddenly from cardiac arrest is coronary heart disease (fatty buildups in the arteries that supply blood to the heart muscle). All known heart diseases can lead to cardiac arrest and sudden cardiac death. Most of the cardiac arrests that lead to sudden death occur when the electrical impulses in the diseased heart become rapid (i.e., ventricular tachycardia) or chaotic (i.e., ventricular fibrillation) or both. This irregular heart rhythm (arrhythmia) causes the heart to suddenly stop beating. Some cardiac arrests are due to extreme slowing of the heart. This is called bradycardia.

As used herein, "ventricular fibrillation (VF)" refers to a condition in which there is uncoordinated contraction of the cardiac muscle of the ventricles in the heart, making them quiver rather than contract properly. Ventricular fibrillation is a cause of cardiac arrest and sudden cardiac death. The ventricular muscle twitches randomly, rather than contracting in a coordinated fashion (from the apex of the heart to the outflow of the ventricles), and so the ventricles fail to pump blood into the arteries and into systemic circulation.

As used herein, "ventricular tachycardia (VT)" refers to a tachycardia, or fast heart rhythm, that originates in one of the ventricles of the heart. The condition is a potentially life-threatening arrhythmia because it may lead to ventricular fibrillation, asystole, and sudden death.

As used herein, "features" refer to characteristics of a medical device or capabilities of a device. Features may include one or more of longer battery life, number of conditions detected, number of conditions treated, level of detection for conditions, energy output and communication features.

As used herein, "notifying" or "alerting" refers to informing a person or processor of an event or condition. For example, an implantable cardiac device may notify a patient or a patient's health care professional of the operational status of the device or in response to a cardiac episode.

As used herein, "alarm" or "alarm component" refers to an electrical, electronic or mechanical component or system for notifying or warning. The warning may be relayed to a person, such as a patient, or to a processor for further analysis or communication relay. Examples of alarms in a cardiac device may be an audio tone or buzzer, a vibration or a visual indicator, such as symbols or words on a display.

As used herein, "operating life" refers to a length of time a device may be reliably utilized. Operating life may be limited by its power source, circuitry or mechanical components, for example.

As used herein, "housing" refers to a frame, bracket, box, can or container for protecting or supporting one or more components of a device. A housing may surround one or more of a power supply, capacitors, circuitry or processor of a device, to name a few.

As used herein, "accelerometer" refers to a device for measuring acceleration and gravity induced reaction forces. Accelerometers may be used to sense or detect inclination, vibration or shock. With regard to a cardiac device, an accelerometer may be utilized to detect if a patient is in an upright or horizontal position. An onboard alarm may be utilized for notification based on the readings of the accelerometer, for example.

As used herein, "capacitor" refers to an electrical or electronic component that can store energy in the electric field between two conductors.

As used herein, "energy source" or "power source" or "power supply" refers to a source of electrical power. Examples of energy sources may be a primary or secondary battery.

As used herein, "electrode" refers to a conducting component that may deliver or receive electrical signals. Electrodes may be positioned in or on a lead that is in electrical communication with an implantable device, for example.

As used herein, "electrocardiogram signal" refers to a tracing of the electric currents that initiate the heartbeat. Such signals may be used to diagnose possible heart disorders or detect cardiac episodes.

As used herein, "primary battery" refers to battery in which the electrochemical reaction of interest is not substantially reversible. Primary batteries are most often of a one time use or are disposable. Types of primary batteries may include Li/CF$_x$, Li/BrCl$_2$, Li/MnO, Li/SO$_2$Cl$_2$, Li/SOCl, or Li/SVO for example.

As used herein, "secondary battery" or "rechargeable battery" refers to a rechargeable or storage battery. Secondary batteries are electrochemical cells that can be restored to full or near full charge by the application of electrical energy. Their electrochemical reaction is essentially reversible, making the cell a rechargeable type. A common type of rechargeable battery is a lithium ion battery.

As used herein, "implantable cardiac defibrillator (ICD)" or "implantable cardioverter-defibrillator" refers to an electrical impulse generator which is fully or partially implanted within a patient who are at risk of sudden cardiac death or other heart ailments that are diagnosable by an implant. The device is capable of delivering one or more electrical shocks to the patient's heart.

Description

FIG. 1 illustrates an implantable cardiac system 100 and an environment 106 (e.g., body or specifically subcutaneous pocket made in the wall of a subject's chest, abdomen, or elsewhere) in which the system 100 can be used. In varying examples, system 100 can be used for delivering or receiving electrical pulses or signals to stimulate or sense a heart 108 of a subject, such as a patient. As shown in FIG. 1, ICD system 100 includes cardiac prophylactic device 102, e.g., an implantable cardiac defibrillator (ICD), and an implantable lead 104. Device 102 includes a source of power as well as electronic circuitry. In this example, device 102 is a battery-powered device that senses intrinsic signals of heart 108 or other body parameters and can then respond in a variety of ways, as discussed below according to the embodiments of the present invention.

The device 102 can further include a body position sensing unit that determines the orientation of a patient's body. Orientation of the patient's body can be determined relative to a horizontal plane, for example, the X-Z plane of the X-Y-Z graph 110. The Y axis is the vertical direction. Correspondingly, the patient 106 shown in FIG. 1 is standing upright in the vertical direction. In an example, the device 102 would not provide therapy if it senses that the patient is standing in the vertical direction. If the patient's body 106 was lying essentially in the X-Z plane then the device 102 is enabled to output certain therapy signals, e.g., defibrillation signals through the leads 104 to the patient's heart 108. In an example, the device 102 determines the orientation of the patient's torso or thorax but not the patient's limbs or head. The patient's body 106 need not be perfectly in the horizontal plane (here, shown as X-Z plane) to allow the device 102 to sense cardiac events and provide therapy. In an example, the device 102 can sense patient physiological parameters in any orientation. In an example, the patient's body can be on a slight incline from horizontal and therapy can be provided. The incline can be less than 20 degrees and, preferably, less than 15 degrees, and more preferably, less than 10 degrees from horizontal. In a further example, the incline is less than 5 degrees. The incline of the patient's body can also include the body being positioned in the reverse Trendelenburg position with the incline being represented in negative inclination relative to the XZ plane of FIG. 1. For example, the incline can be less than −20 degrees and, preferably, less than −15 degrees, and more preferably, less than −10 degrees from horizontal. In a further example, the incline is less than −5 degrees.

In a further example, the device 102 will always sense and provide an output therapy signal if the patient is in a Trendelenburg position, which is the patient body essentially supine with the head below the feet. The device 102 can sense the Trendelenburg position and, in an example, limit an output therapy signal to when the decline is slight from the horizontal. Decline with reference to FIG. 1 is the negative Y coordinates on the graph 110 The decline can be less than 20 degrees and, preferably, less than 15 degrees, and more preferably, less than 10 degrees from horizontal. In a further example, the decline is less than 5 degrees.

The above descriptions refer to the reverse Trendelenburg position and the Trendelenburg position, however, the present disclosure is not limited to the supine position of the patient. Other rotations of the body from supine to prone, inclusive, will not affect the operation of the device 102. In an example, the patient, who is experiencing a cardiac event, may fall to a floor on their side or be lying in bed on their side. The device 102 will still determine that this is a horizontal position and can output the therapy signal. Specifically, the rotation of patient's body in the Y-axis, Z-axis, or X-axis will not prevent the device 102 from outputting a therapy signal.

The device 102, in an example, does not sense nor limit its operation using the position of the limbs of the patient. Instead the device 102 only senses the position of the torso or thorax of the patient. In a specific example, the patient's body being in a semi-supine position with the knees raised bent upward with the soles of the feet and upper body remain in contact with the horizontal surface would be processed as a horizontal supine position in the device 102.

The device 102 can sense cardiac related signals regardless of the position if the body 106. However, the device 102 will not apply a defibrillation signal to the patient's heart through the lead(s) 104 if the body 106 is not essentially horizontal. If the patient is experiencing a fibrillation event and remains vertical, either standing or sitting, then the device 102 will terminate attempt to output a therapy signal. The device 102 may further diagnose itself as having a fault if a serious cardiac event is detected and the patient remains vertical. In another example, the device 102 will wait for the patient to lie down or fall into an essentially horizontal position (i.e., become substantially horizontal due to the cardiac event) and then apply the defibrillation therapy signal. The device 102 will also wait a period of time after it senses the body in the generally horizontal position before outputting the defibrillation signal. In an example, the period of time is in the range of seconds, e.g., less than 10 seconds, less than 6 seconds or less than 4 seconds. The period of time can be about a minute.

The device 102, in an example, is designed free from pacing functions and operates to save a patient in a fibrillation event. In this aspect of the device 102, it operates as an internal automatic defibrillation device. In another example, the device has a brief pacing capability to follow defibrillation therapy to further assist the heart back to normal sinus rhythm. In an example, a pacing algorithm is launched only after the defibrillation therapy and further sensing to determine that pacing is needed. In an example, pacing is only provided for a day. In an example, pacing is only provided for less than a day, less than 12 hours, less than 6 hours, or less than an hour. In a further example, the pacing therapy by the device 102 lasts for only a few minutes (e.g, less than 10 minutes, less than 5 minutes, or preferably less than about 2 minutes) or for only seconds (e.g., less than a minute, less than 45 seconds, less than 30 seconds, or less than 15 seconds)

The device 102, and other examples of an implantable device described herein, use cardiac signal and signal processing algorithms to detect presence of QRS signal which is indicative of heart's rhythmic activity. Irregularities in the electrical operation of the heart are detected from irregularities in detected QRS signal, or sequence(s) of QRS waveforms. Internal algorithms and circuits are used to look at sequence of QRS signals and assess those signals as normal or irregular. Additional algorithms are used to look at irregular signals and further classify them as bradycardia, tachycardia, VF and SCD.

As used in various descriptions herein, the coronal plane of the body is used to compare the position of the body 108 to a horizontal plane (XZ plane in FIG. 1) for purposes described herein with reference to horizontal orientation and applying a therapy signal. Specifically, the part of the coronal plane as it passes through the torso or thorax is used to prevent or apply therapy. Specifically, the part of the coronal plane as it passes through the thorax is used to prevent or apply therapy.

The present devices, systems and methods can further use a plane that includes the left mid-clavical line to determine the orientation of the patient's body. The left mid-clavical plane being perpendicular or essentially perpendicular to the horizontal plane would allow the device 102 to apply a therapy signal. If the device 102 determines that the left mid-clavical plane is not essentially perpendicular to horizontal, then device 102 will not apply a therapy signal.

While the present description uses the heart and a specific example of an implantable device that can use a body orientation sensing unit, the medical implant using the body orientation (position sensing) unit can address other physical conditions of the patient. In an example, the medical device is a neurostimulation device that uses the sensed position of the body in its therapy algorithm or in its sensing functions to correlate patient condition and health to the physical orientation of the patient body.

Figure 2A:
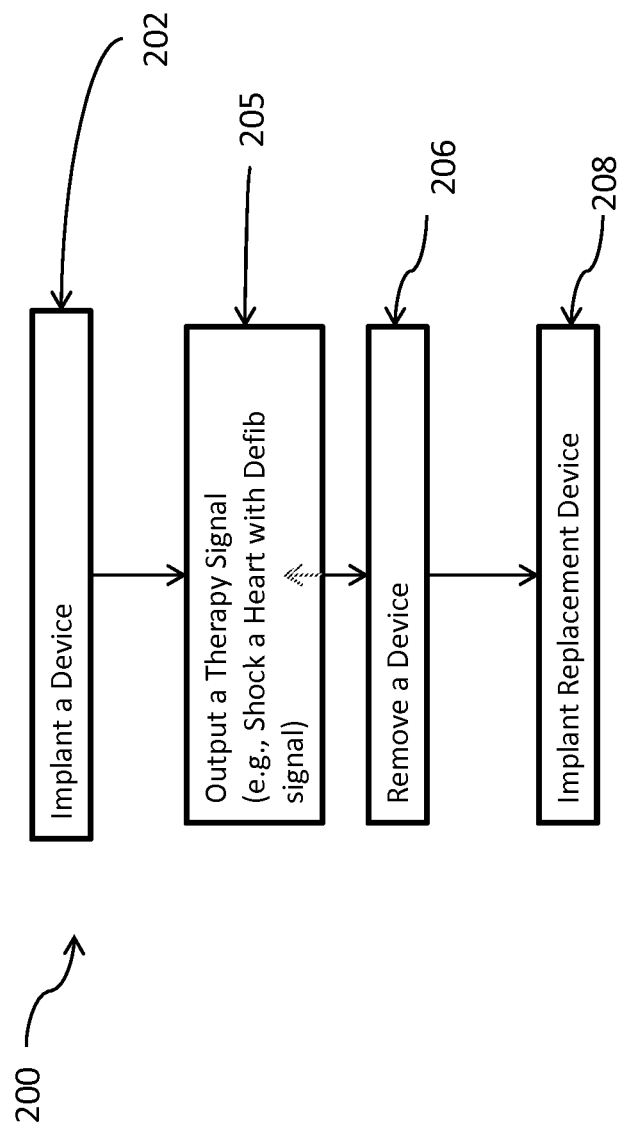
FIG. 2A is a block flow diagram of a method of treating a patient at risk for a cardiac episode, according to some embodiments.

FIG. 2A illustrates a block flow diagram 200 of a method of treating a patient at risk for a cardiac episode, according to some embodiments. At step 202, a cardiac prophylactic device, e.g., device 102 of FIG. 1, can be implanted within a patient. The implantation of the device can be done without defibrillation threshold testing ("DFT"). The device may then output a therapy signal 204 (e.g., shock with an electrical signal) to the patient's heart in response to an adverse cardiac episode. The adverse cardiac episode can be sensed by the device. In an example, the device senses the position of the body, e.g., the torso. The device will not output a therapy signal until the body is sensed to be in essentially horizontal. The device can also wait until the body of the patient is in a correct position, e.g., generally horizontal. Once a shock has been administered and, in the case of a single or limited episode device, at 206, the device can be removed by a health care professional, for example. The device removal occurs in a short period of time following the administration of the first therapy. The period of time could be in the order of days, or few weeks. During this period of time, the prophylactic device of the present disclosure will continue to protect the patient and warn the patient of the urgency of replacement of the device. A replacement cardiac device may then be implanted 208. The replacement device may be a more "full-featured" device or a device capable of treating more conditions or a specific condition now identified by the prophylactic device or by the physician using data from the prophylactic device, or a longer lasting, simple protective device (see e.g., the rechargeable energy source(s), battery or capacitor of the below description), for example.

Examples of a cardiac episode, event or condition can include cardiac arrest, sudden cardiac death (SCD), ventricular fibrillation (VF) or ventricular tachycardia (VT). Once a ventricular fibrillation event or episode or sudden cardiac death event or episode is detected by the device, the heart may be shocked in an attempt to return the heart to a more normal rhythm. Prior to shocking the heart, the device may notify the patient of the event and the possible shock event. The notification can inform the patient of the event and alert the patient move from a generally horizontal position to a generally vertical position so that the device, e.g., device 102 of FIG. 1, terminates the output of a therapy signal. An example of notification may be through an alarm mechanism or component. The alarm can include a tone emitting from the device or a vibration. In an example, the device can emit a signal that is received by an indicator, which includes a visual display, outside the patient's body. After delivery of the therapy, the device can continue to emit an alarm, which may progressively strengthen in intensity, frequency or both as time passes in order to encourage the patient to see a health care professional. This is desired in the event that the device is a "single use" (e.g., a single event or single therapy session) which requires that the patient see their physician as the device is not able to provide further therapies over extended periods of time, e.g., multiple days, weeks or months.

Alternatively or in parallel, the device can emit a signal that is then sent to a health care professional over a communication system, e.g., computer system, telephone system, wireless communication, or combinations thereof, to notify the health care professional of the event.

In another embodiment, the alarm may monitor battery life within the device and emit a warning if the battery life is below a dangerous threshold. The alarm mechanism can be used in conjunction with a body orientation unit to determine if a patient is vertical or prone, for example. If the patient is vertical, then the alarm continues to sound or be emitted. In an example, the alarm may only sound when the patient is in a vertical position, in order to allow sleep but to continue the encouragement to see a health care professional.

The alarm will continue to sound, subject to some limitations in various embodiments described herein, until the patient sees the health care professional, who will have the authority and ability to turn off the alarm.

The prophylactic device initially implanted in step 202 can include fewer features than the replacement device (implanted in step 208), which can apply a greater number of therapies and apply numerous therapy algorithms. Features that may be excluded from device 102 and can be included in a replacement device (implanted in step 208) can include one or more of longer battery life, number of conditions detected, number of conditions treated (e.g., pacing), level of detection for conditions, energy output and communication features. The replacement device can also include pacing features, which is not included in an example of the prophylactic device 102.

The cardiac prophylactic device (e.g., device 102 of FIG. 1) can be limited in operating life after issuing a single event. The single event can include multiple shocks to restore the heart to an acceptable rhythm. In another embodiment, the cardiac prophylactic device is limited in operating life after issuing a second shock in response to a second cardiac episode. The prophylactic device can have a finite life to maintain a high level of known integrity of the device. Alternatively, the device can have a finite life after issuing a shock in order to encourage a patient to see a health care professional, for example. A rechargeable system can include internal circuitry that would purposely expire or terminate the operability of the device after a predetermined length of time, such as from the start date of the device. The device can include various levels of alarms or notifications to a patient or doctor of the device's remaining operating life. A switch can be utilized to control the operation of the device. The switch can be set on a timer or manipulated by a health care professional. For example, a doctor can use a magnet to turn off an alarm, reset the device or otherwise manipulate the device once a cardiac episode has occurred and the patient has returned for treatment. In another example, the physician or other medical personnel can use a remote wireless programmer to interact with the device, e.g., manipulating the switch, setting the life or otherwise downloading or reading data to or from the device.

Before implantation of the device, the patient may be evaluated by a health care professional or indicator system in order to determine the possible risk for a cardiac episode. This step may also be utilized to determine if the patient is not a candidate for implantation, is a candidate for a prophylactic device or is a candidate for a more "full-featured" device. Thus, stratification or tiering of risk level evaluations for an individual patient may be established. The prophylactic device is meant to save a patient from a more serious condition, e.g., cardiac episode that may result in death that may then be subsequently treated by the replacement device and, optionally, medicine and suggested treatment options.

The implanting step 202 can include addition steps. In an example, an external system is electrically connected to the implant, which can include electrical connectors as described herein or connectors designed to be accessed only at implantation. In an example, the electronic system to communicate with an implantable device can include a housing, a connector that can mate with other systems, e.g., an implantable medical device, circuitry to receive electrical energy from outside the housing, an electronics to evaluate and communicate with outside the housing, circuitry to generate electrical signal to communicate status with a device outside the housing. In the specific example of FIG. 2A, the system is mated (e.g., in electrical communication with) with a human implantable cardiac arrhythmia treatment devices, including pacemakers, ICDs, and resynchronization therapy devices. In an example, the connection between the system and device can be an IS-4 connector or a cardiac lead. The circuitry, which can include electronics, inside the system can place an electrical load placed on the input connector at selectable values. In an example, the system housing can include an indicator that communicates status and results to user. The indicator can include a visual display that can communicate messages to the user. In an example, the indicator includes one or more light emitting diodes (LEDs). Implantation can further, using the system, assess proper operation of the medical device, e.g., an ICD or pacemaker, before the device is connected and implanted inside a patient. The assessment, using an internal signal generator, can be programmed to output a signal that imitates heart rhythm to evaluate signal detection capability of the implantable medical device.

Figure 2B:
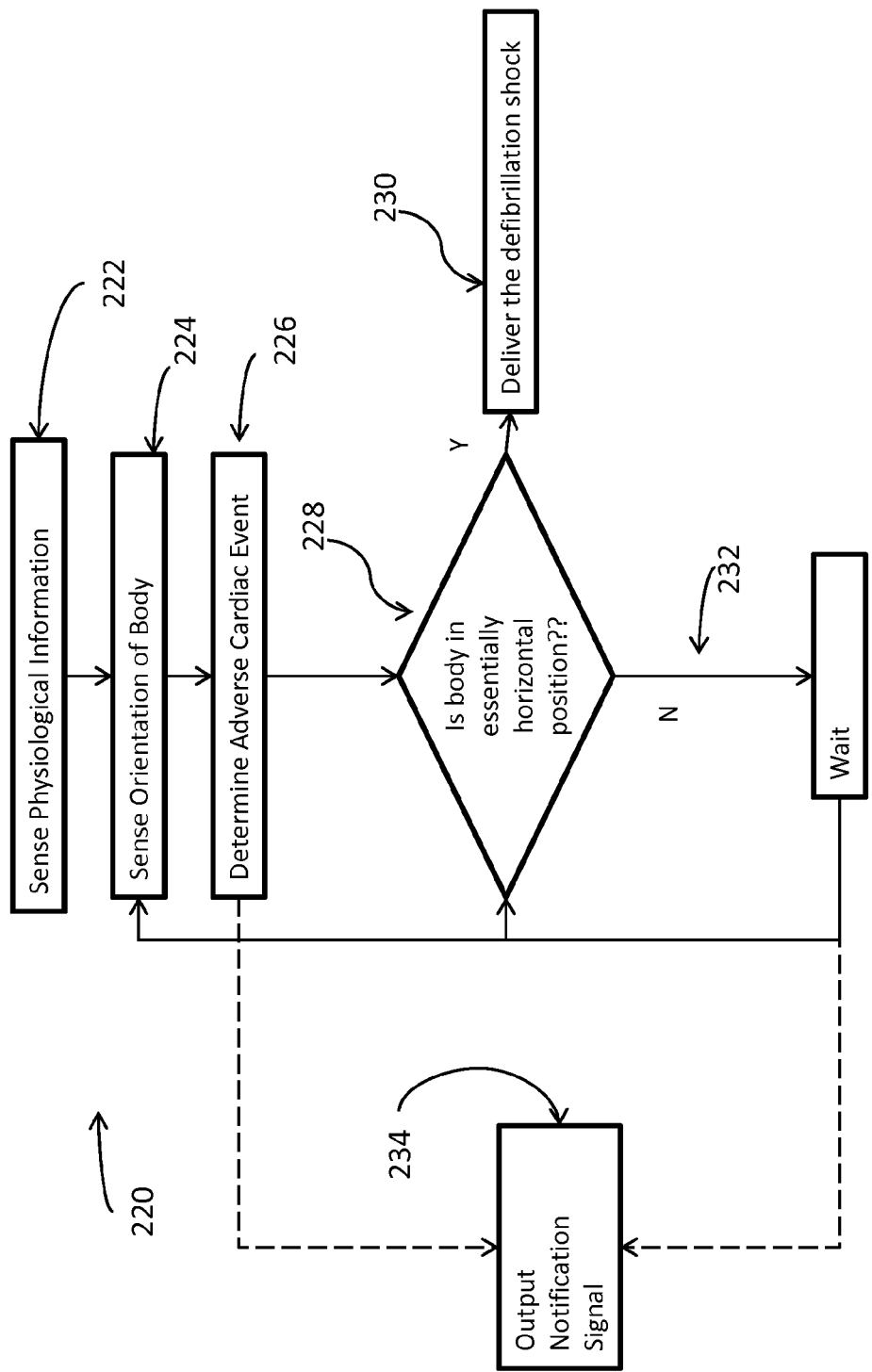
FIG. 2B is a block flow diagram of a method of treating a patient at risk for a cardiac episode, according to some embodiments.

FIG. 2B illustrates a block flow diagram 220 of a method of sensing a condition of a patient and generating an output signal for treating a patient. A medical device, for example implant device 102 of FIG. 1, other at least partially implanted device, or other medical sensor, senses physiological information of the patient. Physiological parameters can include heart signals, breath sounds, blood pressure, ECG data, cardiac output, respiration rate, blood oximetry, patient temperature, and/or other sensed physiological data from the patient. At 222, the device senses patient's physiological parameter(s). At 224, sensing the physical orientation of a person's body is performed. In an example, modules or circuitry in an implanted device, e.g., device 102 described above, provide signals that are analyzed to determine the patient's body orientation. The sensed signals are processed, for example by an electronic device with electronic circuitry, to determine an adverse medical event, for example, a cardiac event, at 226. At 228, it is determined whether or not the body is in an essentially horizontal position. If yes, then a therapy signal is generated by and output from the device at 230. This signal can be output to the leads, through the housing or by other means to electrodes or interfaces with the patient's body. The therapy signal, once output from the implanted device, is intended to be applied to the patient's body. In an example, the therapy signal is a cardiac therapy signal, e.g., a defibrillation signal. If at 228, the body is not in an essentially horizontal position, the process will move to 232 and wait a period of time. This time period can be short, e.g., a few seconds, tens of seconds or a minute or less. After the wait period, there are three possible flow paths for embodiments of the present disclosure. In a first flow, the process returns to step 228 to determine if the body is now in the correct therapy position, i.e., an essentially horizontal position. In a second flow, the process moves to outputting a notification signal that indicates that an adverse event was sensed but the person is in an essentially vertical position at 234. In this flow, it is indicated that an error in the device has occurred and the patient should seek medical care, i.e., review of performance of the implanted device by medical personnel or other trained personnel. In a third flow, the process moves to the sense orientation step 224 and repeats the flow path. This flow is done if the sensing of the orientation stops after the method moves to step 226. In an example, the steps 222 and 224 can be continuous such that the sensing continues while other steps are being performed.

Figure 2C:
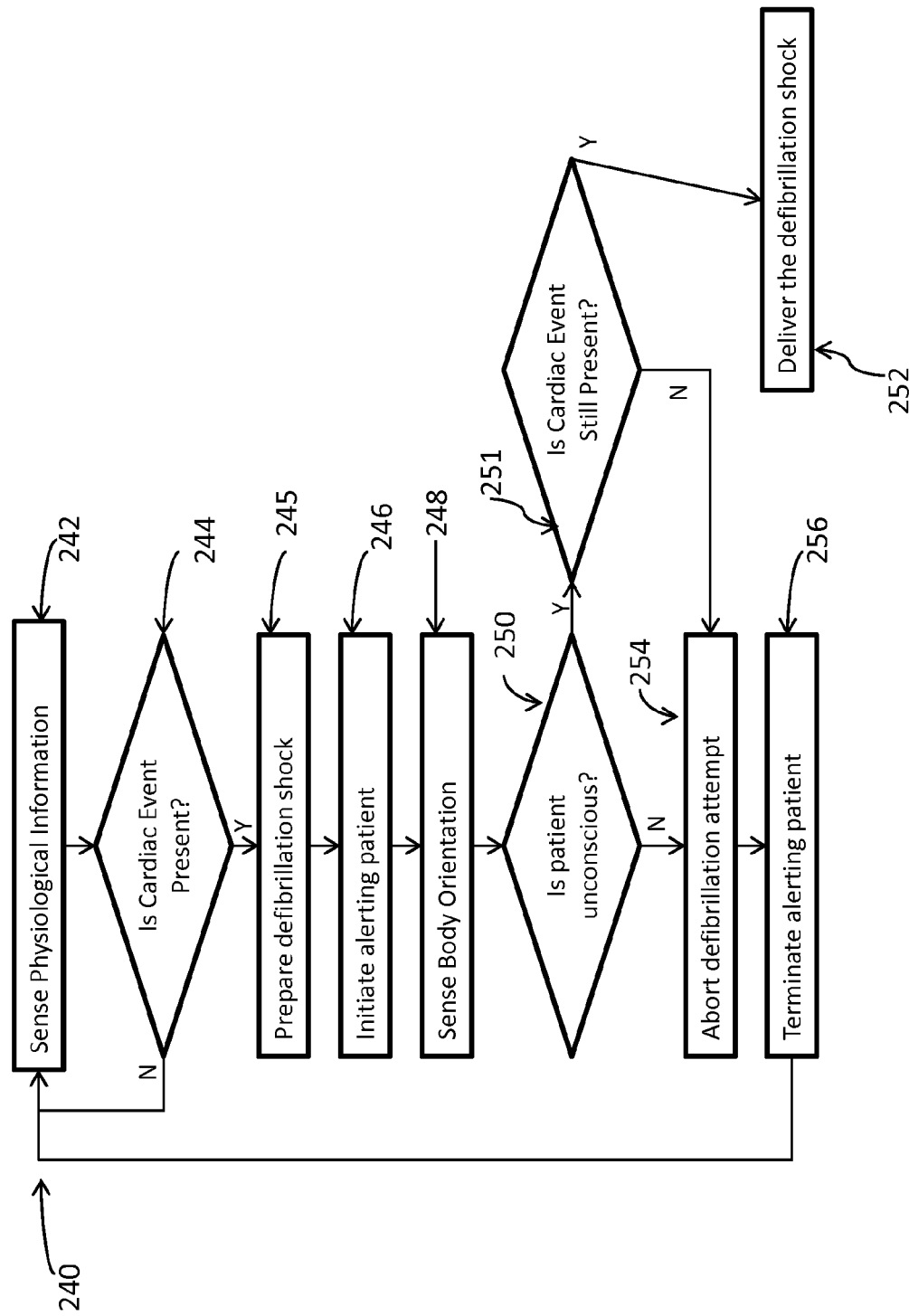
FIG. 2C is a block flow diagram of a method of treating a patient at risk for a cardiac episode, according to some embodiments.

FIG. 2C illustrates a block flow diagram 240 of a process of sensing a condition of a patient and generating an output signal for treating a patient. A medical device, for example implant device 102 of FIG. 1, other at least partially implanted device, or other medical sensor, senses physiological information of the patient. At 242, the device senses patient's physiological parameters. At 244, it is determined whether a cardiac event associated with the patient is present. If no cardiac event is present, then the process 240 returns or continues sensing physiological information at 242. If step 244 determines that a cardiac event is present, then the process moves to 245 and begins preparing a defibrillation shock signal, e.g., charging output energy sources such as capacitors. At 246, the patient is alerted that delivery of a therapy shock is impending. Therapy shocks to a patient's body from a medical device, such as an implant, without warning can be painful for the patient, e.g., when the therapy signal is of sufficient strength and is about to be applied to a sensitive part of the patient's anatomy, e.g., the heart. At 248, the orientation of the patient is sensed. The output therapy signal can be delayed if the patient is in an essentially vertical position. In another example, the orientation can be used to stop output of the therapy signal altogether. At 250, it is determined whether the patient is unconscious. If the patient is conscious, then the process moves to 254 and aborts the defibrillation signal output. At 256, the process terminates alerting the patient. At 251, the cardiac event is confirmed. If the cardiac event is no longer occurring, then the process moves to step 254. If the cardiac event is still present, then the process moves to step 252. At 252, the medical device prepares the circuitry to output the therapy signal and outputs the signal from the device.

While the above process as described with diagram 240 refers to alerting the patient, it will be within the scope of the present disclosure to alert the patient and the medical care provider or family of the patient. It is further within the scope of the present disclosure to record all of the data on which the process relies and computes for later analysis. The process of diagram 240 provides safeguards to only apply a therapy signal to a patient when the therapy signal is required. Applying a defibrillation signal to a patient when the defibrillation signal is not needed is very painful for the patient. If the patient does not lose consciousness or can remain vertical, then the device may be in error if it diagnoses a fibrillation and should not output a defibrillation signal. By alerting a patient that a therapy signal, e.g., a defibrillation signal, is about to be applied, the patient can move to a vertical position, e.g., merely stand up and remain standing, to prevent the output of the possibly painful therapy signal.

Figure 3:
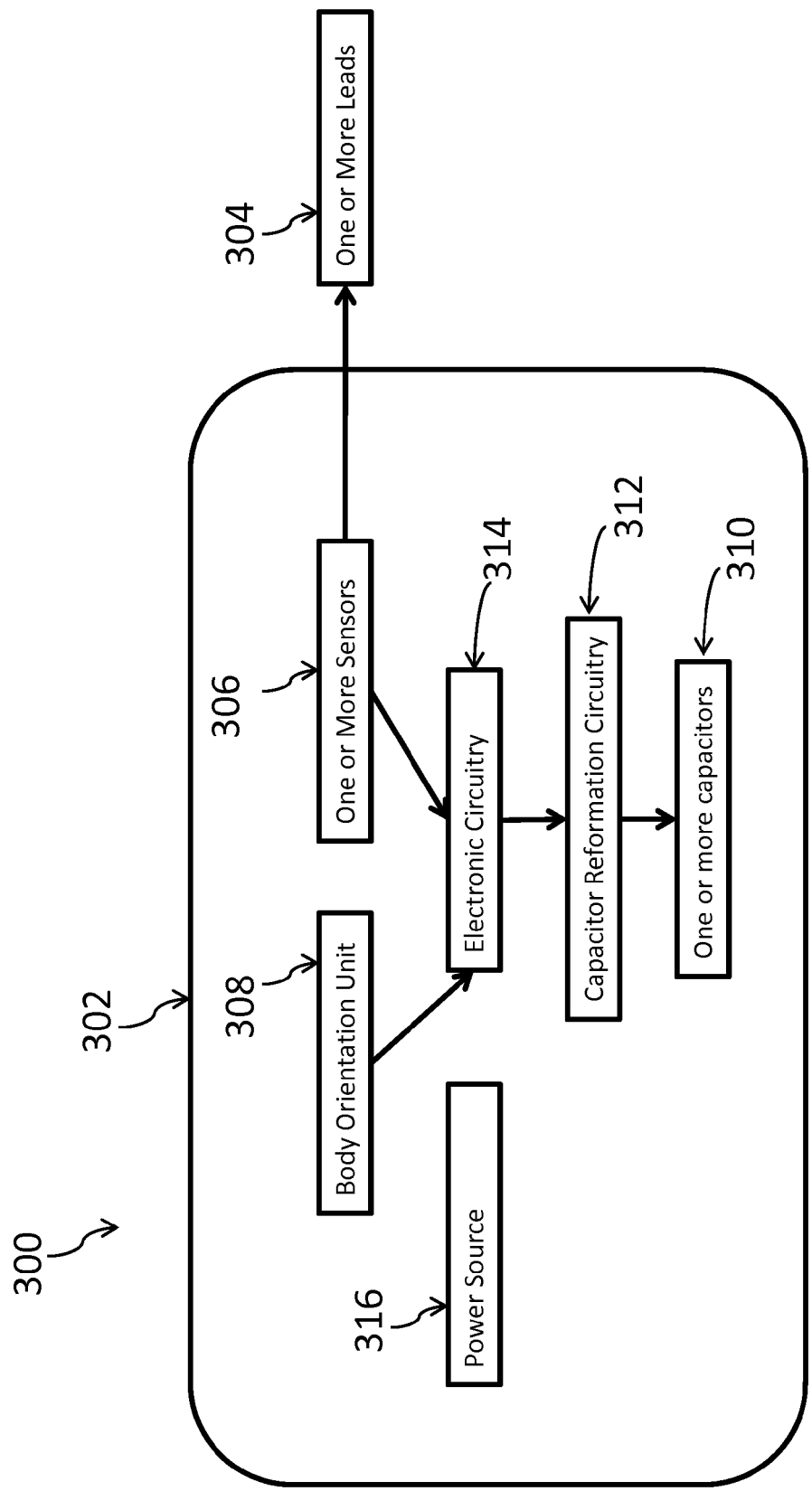
FIG. 3 is a schematic view of an implantable device for treating a patient at risk for a cardiac episode, according to some embodiments.

Referring to FIG. 3, a schematic view 300 of an implantable device for treating a patient at risk for a cardiac episode is shown, according to some embodiments. The device 300 can include a housing 302 including an integrated lead and/or connected to one or more leads 304, which extend from the housing 302. In some uses, the housing is referred to as a can, which is biologically inert in a body of a mammal, such as a person. One or more cardiac sensors 306 for detecting cardiac episode are positioned within the housing 302. Some sensors or parts of the sensors may be positioned with the leads 304. A power or energy source 316 can be in electrical contact with the housing 302, electronic circuitry 314, body orientation unit 308, capacitor reformation circuitry 312, and one or more capacitors 310. The body orientation unit 308 can be located within the housing 302 in order for the device to detect whether the patient is positioned in an upright (vertical) position or lying flat (horizontal). The body orientation unit can include the features described above with regard to FIG. 1.

The body orientation unit 308 includes means, software, hardware or both, to determine the orientation of the body that the device 300 is sensing. The unit 308 can sense body orientation(s) described herein. The body orientation unit 308 can output orientation data or control data to the electronic circuitry 314. The orientation data can be processed by the electronic circuitry, which can include a processor or logic circuits, to allow or prevent output of a therapy signal by the circuitry 314 using power that can be stored in the capacitors for rapid delivery of an electrical therapy signal to a patient's heart for therapy. In an example, the circuitry 314 includes control circuitry for the device 300 and therapy circuitry to determine and apply therapy signals.

The body orientation unit 308 can include an accelerometer. The accelerometer can be a single-axis and multi-axis device to detect magnitude and direction of acceleration as a vector quantity, which can be used to sense orientation. The accelerometer can also sense acceleration, vibration shock, and falling. In the event of falling, the accelerometer can determine that the body of the patient is or has fallen. Accordingly, the patient would be in a position or orientation where the device 300 can output a therapy signal. An example of an accelerometer that can be positioned in the housing 302 is a micromachined device or microelectromechanical system (MEMS). Such device can be referred to as a micromachine (in Japan), or micro systems technology—MST (in Europe). Accelerometers that are made on a nano-scale are included in the present use of MEMS. The accelerometer can be a digital device or an analog device. A plurality of different accelerometer devices, e.g., a plurality of two-axis devices, a single three-axis device, and a six-axis device, can be combined together in the unit 308, which outputs a signal indicative of an orientation of a patient. The accelerometer can be a capacitive device that relies on changes in capacitance based on the position of the accelerometer to determine its position relative to a horizontal plane.

The body orientation unit 308 can include an inclinometer. In an example, the inclinometer generates an artificial horizon and measure angular tilt with respect to the artificial horizon. The artificial horizon can be set at the time of implantation of the device, e.g., device 102 or 302. During an implantation procedure, the patient is lying in the horizontal position so the implanted device is started and sets the horizon, which is in the horizontal plane. An example of an inclinometer can be positioned in the housing 302. The inclinometer can be a micromachined device or microelectromechanical system (MEMS). In an example, the inclinometer can be at least one of a capacitive device and a MEMS device, which can output a signal indicative of an orientation of a patient.

The body orientation unit 308 can include a gyrometer or gyroscope. The gyrometer can include at least one of a MEMS device and a three-axis device, which can output a signal indicative of an orientation of a patient.

In an example, the device 300 includes a therapy circuitry, e.g., part of electronic circuitry, to deliver only a defibrillation signal. In an example, the therapy circuit does not include or does not have active pacing functions. In an example, the therapy circuitry cannot make a determination regarding pacing. The therapy circuitry is free from structures for delivering pacing signals in this example.

The body orientation unit 308 can be set such that it knows the horizontal plane at the time of implantation of the device 302 (or 102). The unit 308 can be powered up upon implantation with the knowledge that the patient is lying down on a surgical table. Typically, the patient is supine on the surgical table. Thus, the unit 308 can determine the rotational position of itself as well as determining the horizontal plane. This initial data provides the basis for determining the orientation of the patient and, hence, when therapy can be applied or withheld.

The capacity reformation circuitry 312 is to manage the charging and unloading of the capacitors 310. The capacitors 310 can be powered by the power source for delivery of the shock or therapeutic signal. The capacitors can deliver a shock to the heart of about 500V, about 600V, about 700V, about 750V or about 800V. The capacitors may deliver energy to the heart up to about 30 J, up to about 40 J or up to 50 J, for example. The capacitors can be tantalum capacitors, for example. In an example, the capacitors 310 include a smaller capacity capacitors to act as charge pumps between the battery and larger therapy signal output capacitor(s). In an example, the output capacitor(s) is connected to an output that is connected to the leads or housing to deliver the therapy signal.

The energy source 316 can include one or more of primary batteries or secondary batteries. For example, the energy source 316 can be a primary battery that would have a life of about 3 years, about 4 years or about 5 years. Additionally, the energy source 316 may have a reliable battery life after delivering shock therapy of about 1 month, about 2 months or about 3 months. The batteries can include multiple cells. The batteries can be based on lithium-silver vanadium oxide chemistries. The batteries can provide 3 volts, 6 volts or more.

If one or more rechargeable batteries are utilized as part of the energy source 316, the batteries may be recharged by the patient through an optional recharging port or interface. An example is described in greater detail below. Rechargeable batteries can be utilized to capture back the capacity reformation energy, increasing the efficiency of the device (300 or 102) and potentially extending the life of the capacitors 310 and the device 302. In order to maintain the life of the capacitors 310, energy is periodically charged into the capacitors. If no shock is needed, the energy is typically dumped and, hence, wasted. In embodiments of the present disclosure, this energy can be re-directed to one or more rechargeable batteries. The capacity reformation circuitry 312 can act to manage the flow of energy between the capacitors 310 and the energy source 316, which can include non-rechargeable batteries and rechargeable batteries. The circuitry 312 can include overcharge protection to ensure gradual restoration of energy and improve safety of the device 300. Circuitry 312 can also include thermal fuses and/or current fuses to limit thermal output of the device 300 and/or current flow in the device 300.

In many conventional rechargeable devices, only small rechargeable batteries, which deplete quickly and need to be charged up often, are provided. Small batteries refer to the amount of charge stored in the battery. In an example, a small battery does not store charge for more than two out therapy signals and, in some example, does not store sufficient charge for a single medical therapy signal from an ICD, such as devices 102 or 300. Such a conventional implantable battery design requires daily or weekly charge and would require patient's support to ensure the device includes sufficient charge for operation of the device. Such rechargeable batteries have not been adopted in life saving devices, e.g., conventional cardiac implant devices, that must be functional at all times as patient compliance may not be complete or sufficient with regard to the recharging regimen. Examples of the present disclosure include at least one non-small, i.e., large, rechargeable battery that would last months with multiple uses and last years if used less. The present device is more patient friendly and will not require constant care and upkeep by the patient and the medical care provider.

In an example, the capacitor reformation circuitry 312 can also act as a reformation device for the rechargeable batteries. Rechargeable batteries have batteries have a finite life based on unwanted chemical or physical changes to or the loss of active materials in the battery. Circuitry 312 can sense the formation of a reduced charge storing state of the battery and attempt to reform the battery by applying a charge-discharge pattern that will affect cell chemistry, e.g., break down unwanted crystals in the battery chemistry. The circuitry 312 may be able to restore the rechargeable battery to, or near to, its full capacity by repeating the specific charge-discharge pattern controlled. Circuitry 312 can transfer the charge between rechargeable batteries or between the rechargeable battery and the capacitors.

In an optional embodiment, the device (300 or 102) can rely substantially on the capacitors for charging and delivery of therapeutic shock signals, with little need for batteries. A small rechargeable battery may be available as a temporary storage device for capacitor charging and reformation to maintain the life of the capacitors and possibly the battery as well. Alternatively, capacitors may be substantially removed from the device and batteries utilized to deliver shock therapy and maintain the integrity and monitoring of the device. In yet a further embodiment, some combination of energy may be drawn from both capacitors and batteries to deliver the high energy output therapy. The therapy circuitry as part of circuitry 314 can control the location from which a therapy signal is generated.

The capacity reformation circuitry 312 can include a feature that monitors the residual energy in the battery (part of energy source 316) and prevents the start of a charge cycle if the energy available is not sufficient to deliver the proper intensity of shock. The circuitry and system may maintain enough energy for communication and processing functions to proceed until replacement of the device, for example.

The housing 302 surrounds or contains one or more of the components of the device. The housing 302 may provide separation, protection, support or increased safety of the components, for example. The housing 302 further acts to protect the patient from one or more the components, such as the electrochemical reactions occurring within a power source 316 or leakage of material in the components to the patient's body.

The cardiac sensors 306 can be on or integrated into one or more electrodes of one or more leads 304 positioned in or near the heart. The sensors 306 can detect cardiac arrhythmias, for example. Cardiac sensors 306 may be simplified to only, and reliably, detect for VF. In combination with an accelerometer, such an indication of VF episode and patient position would output a very reliable set of instructions for the device 300 or 102 to begin shock therapy.

Electronic circuitry 314 can be in electrical communication with one more components of the device 300 in order to manage sensing and stimulation of the heart via a shock signal output. The circuitry 314 manages the generation and delivery of the biphasic or monophasic shock waveforms delivered to heart in response to a cardiac episode, which can be sensed by sensors 306. The electronic circuitry 314 can include an expiration system. The circuitry 314 may be activated at implant, but is programmed or mechanically or electrically triggered to discontinue operation of the device upon certain conditions. Such conditions may include time or operating life of the device, time from a first or subsequent delivery of a therapeutic shock or in the event of some failure or depletion of one or more of the components of the device.

In an embodiment, the expiration system of the electronic circuitry 314 can be in the form of hardware, software instructions, or both. The expiration system can be a fuse or other forms of electronics that act similar to a fuse (such as an antifuse). Such a fuse could be positioned at the output of the device, e.g., at the connection of the electronics to the leads. When the expiration time has been reached, the fuse electrically open circuits the internal electronic circuitry 314 from the output such that therapy electrical signals cannot output to the leads and, hence the patient. The device can continue sensing and monitoring the patient, e.g., through the sensors and leads, but will not have the ability to delivery therapy signals. This approach is useful for cases where the ongoing monitoring is needed and required. It is expected that the physician or other medical care provider will ensure the device is replaced before reaching this point of operation.

It is within the scope of the present disclosure to position the fuse in other positions in implant device (300 or 102). In another embodiment, a fuse, or other forms of electronic circuitry that act similar to a fuse, is placed at the output of the energy source to prevent powering the device. Once the expiration time (e.g., a stored date) is reached, the fuse is physically burned to terminate the application of power to the circuitry, e.g., signal processing electronic circuitry, leaving the section inoperative.

In another embodiment, the electronic circuitry 314 is unchanged and the internal software of the device is used to disable operation and control of the signal processing, preventing any therapy to be delivered. In this method, the device is fully operational, but the software has prevented its therapy operation to ensure safety of the patient.

In another embodiment, the electronic circuitry 314 continues to operate but the fuse is positioned at the energy source to prevent charging of the high power, fast discharge energy sources, e.g., capacitors. Accordingly, a therapy signal cannot be produced by the device after the expiration time is reached. Even if the device 300 or 102 cannot output a therapy signal, the device can continue to sense and record data relative to the health of the patient and the device's operation. In an example, the device 300 or 102 continues to monitor the QRS signal and the position of the patient's body. The device 300 or 102 also stores data related to when it stopped its ability to output a therapy signal and, possibly, the reason for such a therapy signal stoppage. The reasons can include position of the patient, lack of sufficient electrical charge in the device, or expiration of the device.

While described as a fuse, it will be recognized that other forms of electronic control devices can be used. In an example, a switch, e.g., see FIGS. 14-19 and corresponding description, to prevent the output of a therapy signal, e.g., a high voltage or high power electrical signal) from the device. The switch can open circuit the output of the medical device and allow other functions such as sensing and recording data and outputting data from the device. The switch can comprise transistors, transistor circuitries, operational amplifiers (op amps) or other circuitries to control the output or generation of therapy signals.

As such termination of service will leave the patient in an unprotected state, the present disclosure can further include for various methods and devices of informing the patient and the physician of imminence of the expiration time. Informing can include circuitry and mechanical devices to output and alarm signal from the device (102 or 300). The alarm methods and systems can be implemented in the circuitry 314 or be part of a separate component as described below with regard to FIG. 4.

The electronic circuitry 314 may be utilized to gradually increase the amount of electric shock delivered until the patient is recovered from the cardiac episode. The shock signals may be stepped up in intensity over set increments of time or in response sensor readings. The shock output may begin at 20 J and then increase by 10 J until the patient is recovered, for example.

The circuitry 314 may also be configured to allow for abortion of the shock sequence by the user in the case of a false positive event. If a patient is not suffering from a cardiac event, the patient would be able to terminate the sequence by contacting a tool (i.e. magnet) with the device or by entering a code into a user interface, for example. This function may be in place of or in conjunction with both the alarm system and accelerometer readings. In another embodiment, the patient may be able to change positions and thus engage the body position sensor in order to terminate sequence.

In operation, the prophylactic device 300 can operate to reduce cases of what is called inappropriate shock. These are cases where the device has misdetected the presence of a VF or SCD and administers shock to the patient when it is not needed. The experience of a defibrillation shock while awake and alert is a very unpleasant experience, which is not appreciated by the patients. It has always been a desire of the device companies to improve the detection algorithms and operation of the device to the point where no inappropriate shocks are delivered, while the detection of VF is not compromised. The present prophylactic device (300 or 102) includes sensors, such as body position sensors 308, that can inform the device 300 of the position of the torso (or thorax) of the patient in relation to the earth surface. The device 300 will use the position of the body as a confirmation of the detection of a cardiac event in need of a defibrillation signal. In many cases, the occurrence of VF will result in loss of consciousness and collapse of the patient. Once the device detects the presence of a VF episode and confirmation of the horizontal position of the body, then it proceeds with administration of the defibrillation shock. The process of shock release requires charge of the capacitors which will take a few seconds, for example, 10 seconds. During this period the device will sound its internal alarm to alert the patient that a shock will be administered. Should the patient be alert and the detection of the VF inappropriate, all the patient has to do to divert the shock is to stand or sit upright. The movement of the body and vertical position of the torso or thorax is an indication to the device that a shock is no longer needed, therefore the shock process terminated and administration of it stopped. The energy stored in the capacitors can be used for other purposes. In an example, the capacitor energy can be restored to the battery, if the battery is rechargeable. In another example, the capacitor energy can be used to drive the other circuits of the device, e.g., sensing, computing, and storing data.

Tools (i.e. magnets) may be utilized before implantation in order for the surgeon, doctor or other health care professional to test the device (300 or 102). In place of the leads, a mating unit may be inserted to test the device to ensure proper functioning. The mating unit can also be attached to the receptacle described below with regard to FIGS. 12A-12C. The mating unit and/or device may include an internal integrity self-test that may be triggered by a tool. A light or other indicating component may be inserted into the electrode or lead connector. Once the self-test has been run, the device may output a signal to light up the connected light or indicating component to signal the results of the test. Both high voltage and low voltage functions of the device may be tested in this way prior to implantation. The doctor or other health care professional may use the magnets to turn the sensors or alarms to the "off" or "on" position respectively. Different magnets may be provided to a patient or health care professional that would provide different functions.

The device (300 or 102) can optionally include a communication system for transferring data within the device or from the device to a processor, a network, a health care facility or professional or to the patient. A data storage system may be associated with the device, either internally or via a connection from an external location. The device may store physiological information about the patients prior to, during and after the cardiac episode that would allow a physician or health care professional to diagnose and understand the condition of the patient, post intervention. Such information may assist the physician or professional in determining future device implantation or treatment regime.

Figure 4:
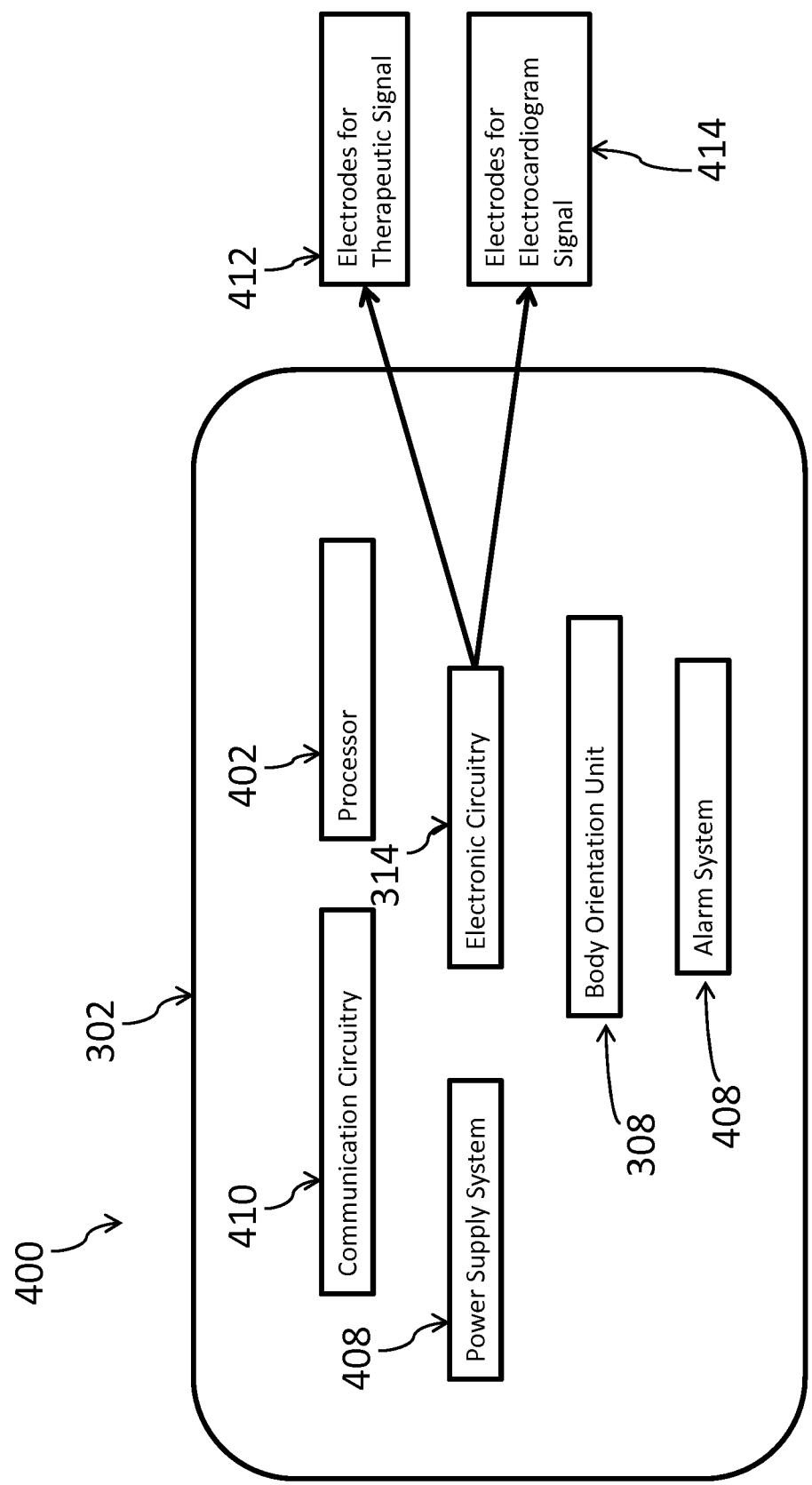
FIG. 4 is a schematic view of an implantable device system for treating a patient at risk for a cardiac episode, according to some embodiments.

Referring to FIG. 4, a schematic view of an implantable device system 400 for treating a patient at risk for a cardiac episode is shown, according to some embodiments. An implantable cardiac system 400 includes a housing 302 and electronic circuitry 314 for controlling one or more of power management, processing signal processing, information memory and management circuit, and sensing and simulation output. The system can also include diagnosis and treatment processor, with machine readable software instructions, 402 for diagnosing health issues, diagnosing mechanical issues, determining therapy output and manage patient health indicators over time. The system 400 includes a power supply system 404 with at least one rechargeable battery and an associated recharging system 406.

An alarm system 408 is provided to inform the patient of energy levels and the integrity of system. The alarm system 408 will notify the patient and/or the physician in ample time to plan replacement procedure for the replacement of the device when the device has expired. In an embodiment, the alarm system 408 includes an internal sound generator, e.g., a buzzer or speaker, in the can or one of the housings. The sound generator is attached to, or is in close proximity of the outer shell of the device housing to provide improved audio delivery outside the device and outside the patient's body. The sound generator can emit an alarm signal with tone and/or notes. In the event the device has reached or is close to reaching replacement time, the device uses the internal alerting mechanism to inform the patient by sending periodic alarms. Since alarms and internal sounds are disruptive to rest time, the internal body position sensor is used to decide when to deliver the alarm. For example, in the event the alarm is not critical, the device only delivers the alarm when the patient is vertical, and stays quiet during rest time when the patient's body is horizontal. In another example, the patient must be at rest, i.e., not in motion, for the device to activate the sound generator.

Communication circuitry 410 may be associated with a communication system for relaying information within the system or to an outside source. Outside sources may include a remote processor, health care professional, network or a patient. One or more output electrodes 412 are included in the system for delivering a therapeutic signal to a heart. The output electrodes 412 may be positioned in or adjacent to a lead, for example. Furthermore, one or more sensing electrodes 414 for delivering an electrocardiogram signal from the heart to the electronic circuitry 314 can be part of the device. Optionally, a programming or user interface (not shown in FIG. 4) may be utilized. An emergency device or component may optionally be utilized to activate an immediate reaction in the device.

Figure 5:
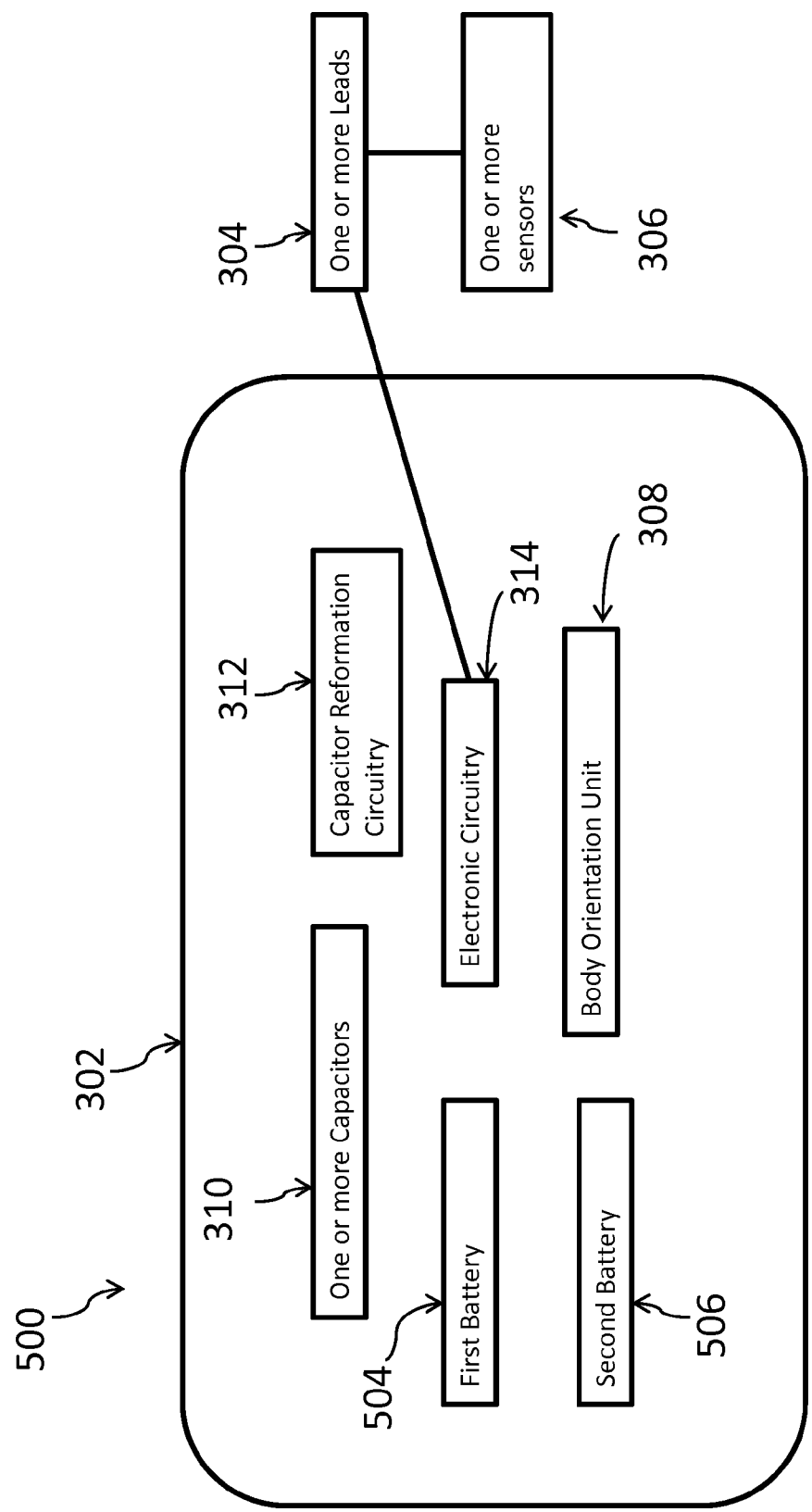
FIG. 5 is a schematic view of an implantable device for treating a patient at risk for a cardiac episode, according to some embodiments.

Referring to FIG. 5, a schematic view of an implantable device 500 for treating a patient at risk for a cardiac episode is shown, according to some embodiments. In another embodiment, the ICD includes one or more housings 302 associated with a first battery 504 for powering diagnostic and monitoring functions and a second battery 506 for powering a shock output. The device utilizes one or more leads 304 and one or more cardiac sensors 306 for detecting a cardiac episode. Additionally, the device uses an accelerometer 308 for detecting patient position. One or more capacitors 310, capacity reformation circuitry 312 and electronic circuitry 314 may be located within at least one of the one or more housings 302. The first battery 504 and second battery 506 are a primary battery or secondary battery, but not both primary or both secondary.

In one embodiment, the first battery may be a primary battery and the second battery may be a secondary battery (i.e., rechargeable battery). Alternatively, the first battery includes a secondary battery and the second battery includes a primary battery. The device may further include an electrical connection between the first battery and second battery under a control of the device to prevent a back charge attempt from the rechargeable battery to the primary battery.

The primary battery may be utilized to power diagnostic and monitoring functions while the secondary battery may power the high energy shocking function. Alternatively, the primary battery may be utilized for high energy output and the secondary battery used for diagnostic, monitoring and optional pacing.

The rechargeable battery may be charged from energy stored in the primary battery. The first and second batteries may be housed in a single housing or in separate housings, in electrical contact with one another. In one embodiment, the primary battery and the monitoring and diagnostic circuitry and their associated charge command and control system may be positioned in a first housing. A second housing may include the charge delivery system and associated secondary battery.

Figure 6:
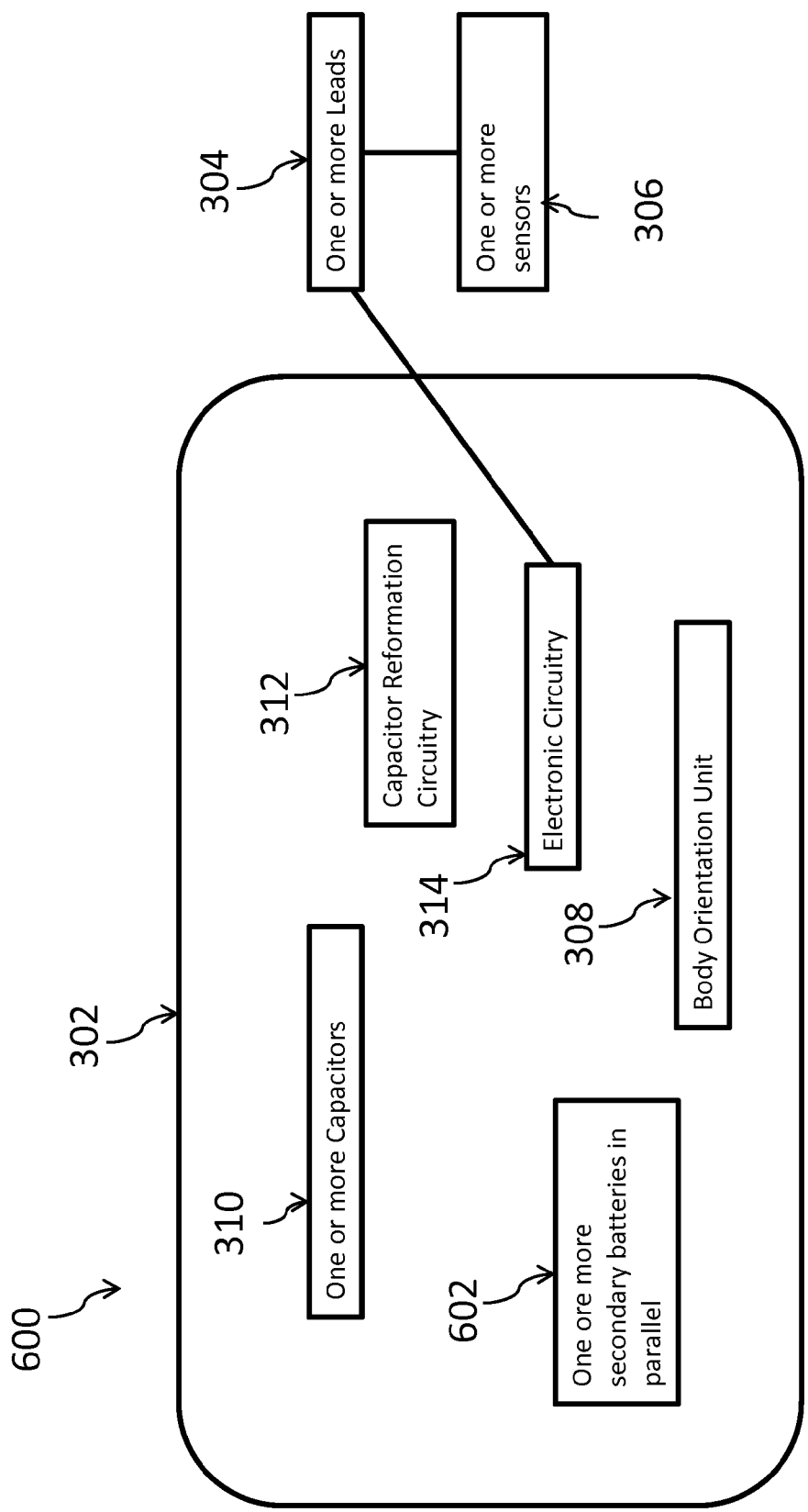
FIG. 6 is a schematic view of an implantable device for treating a patient at risk for a cardiac episode, according to some embodiments.

Referring to FIG. 6, a schematic view 600 of an implantable device for treating a patient at risk for a cardiac episode is shown, according to some embodiments. In another embodiment, an ICD includes one or more housings 302 and two or more cylindrical rechargeable batteries 602 electrically connected in parallel with one another. The device utilizes one or more leads 304 and one or more cardiac sensors 306 for detecting a cardiac episode. Additionally, the device uses a body orientation unit 308 for detecting patient position. One or more capacitors 310, capacity reformation circuitry 312 and electronic circuitry 314 may be located within at least one of the one or more housings 302.

The batteries 502 may be cylindrical in shape to lower the cost of manufacturing and increase compatibility while maintaining an acceptable energy density. Each battery may be associated with independent circuitry for independent operation and charge collection. The device may also include circuitry to manage incoming charge and multiplex to individual cells. Multiple batteries electrically connected in parallel may allow for a smaller charge to collect in each battery. The charging time is then reduced by the number of batteries used since each battery may be charged independently.

The body orientation unit 308 can be incorporated into any of the prophylactic devices described herein. The features of the body orientation unit 308 can detect the position of the patient, vertical or horizontal and numerous angles between vertical and horizontal. In an example, the body orientation unit 308 can provide resolution of the patient's position to a resolution of two degrees.

The prophylactic device 102, 300, 400 or 500 can have a limited life device that has the features needed to detect and treat episodes of SCD and VF that are best treated via a defibrillation shock. The device will have large enough battery that allows it to deliver the max shock energy needed to revive the heart in a single defibrillation attempt. Therefore rescue attempt should recover the patient in a single shock or sequence of shocks of similar energy nature. The ability of the device to output maximum energy of 40 J on each attempt will eliminate the need for Defibrillation Threshold Testing ("DFT") testing. There is a belief by a group of physicians and scientists that application of DFT testing in implant setting exposes patients to unnecessary risk and unnatural cardiac stress. The present device not having the energy limitations of the present cardiac implants will allow the physicians to skip the DFT step and move on to the implantation of the device.

Figure 7:
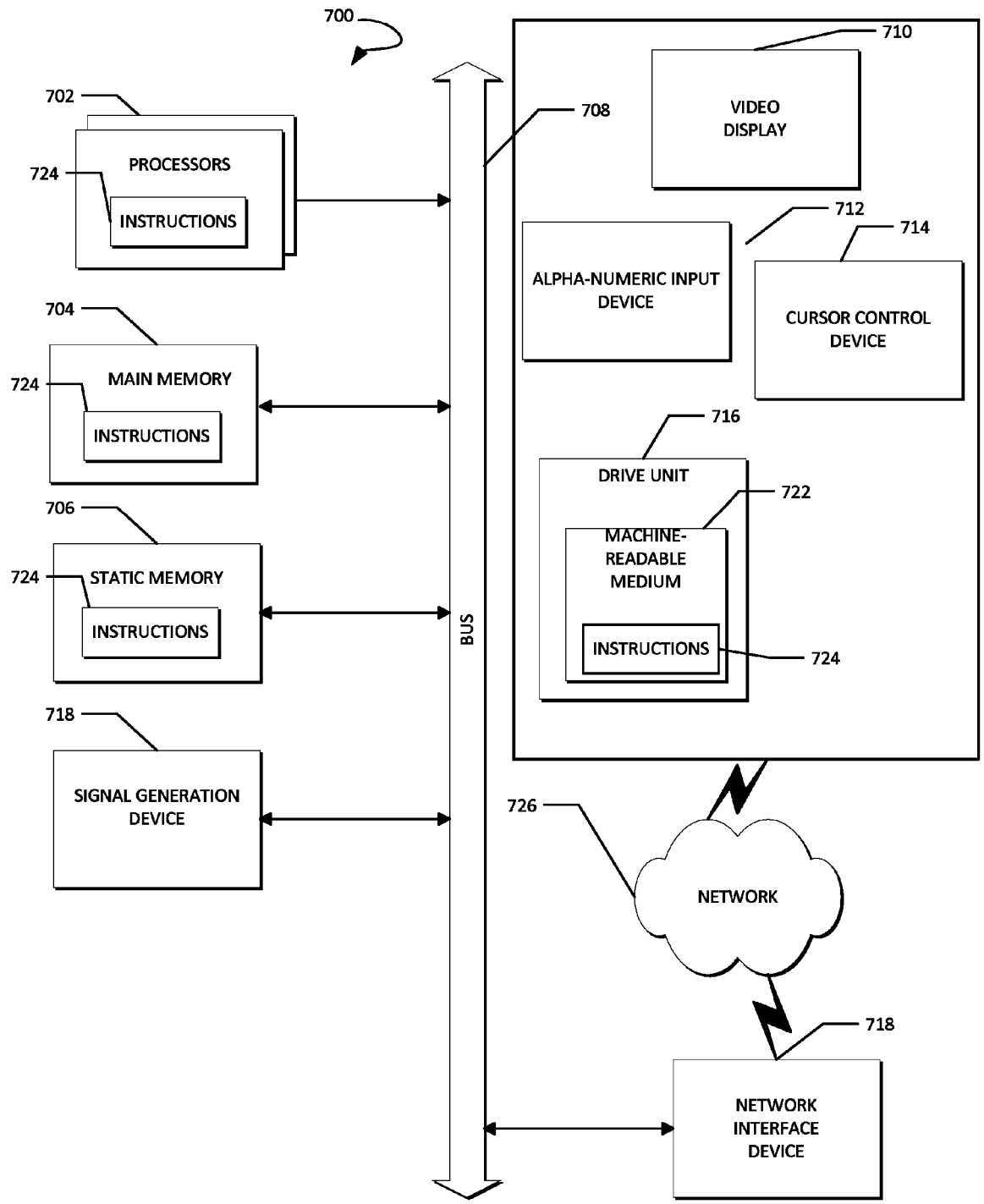
FIG. 7 shows a diagrammatic representation of a machine in the example form of a computer system within which a set of instructions for causing the machine to perform any one or more of the methodologies discussed herein may be executed, according to an example embodiment.

FIG. 7 shows a diagrammatic representation of a machine in the example form of a computing device 700 within which a set of instructions for causing the machine to perform any one or more of the methodologies discussed herein may be executed. In some embodiments, the computing device 700 may incorporate the functionality and associated modules illustrated in FIGS. 1-6. In alternative embodiments, the machine operates as a standalone device or may be connected (e.g., networked) to other machines. In a networked deployment, the machine may operate as a peer machine in a peer-to-peer (or distributed) network environment. The machine may be any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. The example machine 700 includes a processor 702 (e.g., a Central Processing Unit (CPU), a Arithmetic Processing Unit (APU), application specific integrated circuit, logic circuits, or any of the listed in combination), a main memory 701 and a static memory 706, which communicate with each other via a bus 708. The computing system 700 can also connect to programmer through a wireless connection. The programmer can include an alphanumeric input device 717 (e.g., a keyboard), a User Interface (UI) cursor controller 710 (e.g., a mouse), a memory unit 716, a signal generation device 729 (e.g., a speaker) and a network interface device (e.g., a transmitter)

720. The memory unit 716 includes a machine-readable medium 722 on which is stored one or more sets of instructions (such as instructions 721) and data structures (e.g., software) embodying or used by any one or more of the methodologies or functions illustrated herein. The software can also reside, completely or at least partially, within the main memory 701 and/or within the processor 702 during execution thereof by the computer system 700. The main memory 701 and the processor 702 also constitute machine-readable media.

Figure 8:
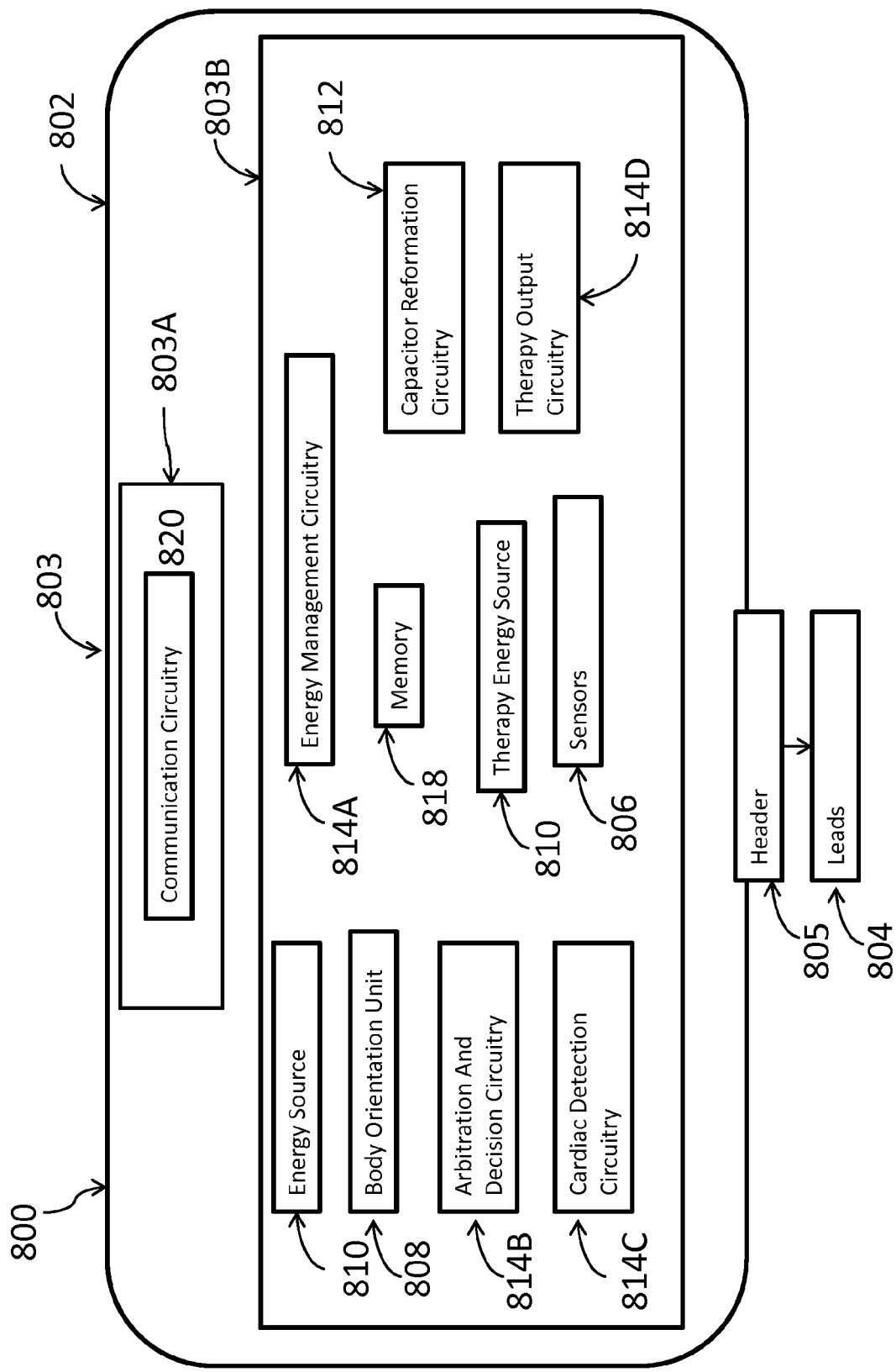
FIG. 8 is a schematic view of an implantable, medical system, according to some embodiments.

FIG. 8 shows an implantable cardiac therapy system 800, which can be implanted in a mammal, such as a person, to sense and/or to provide therapy. The system 800 can include an implant device 802, which can sense cardiac events and, optionally, to provide cardiac therapy. In an example, the device 802 is an implantable cardiac defibrillator (ICD). In an example, the device 802 does not provide pacing therapies but is used as a life saving device in event of severe cardiac episode. In various examples, device 802 can sense parameters related to or provide therapy related to at least one of cardiac pacing, cardiac defibrillation, electrical stimulation for management of pain, electrical stimulation for prevention of treatment of obesity, electrical stimulation for treatment of neurological disability, ailment or deficiency, electrical stimulation for treatment of physical disability, chemical release for treatment of pain or any other physiological or neurological ailment, or combinations thereof. In varying examples, device 802 can deliver or receive electrical pulses or signals to stimulate or sense a heart of a subject, such as a patient. The device 802 can include at least one housing 803 or include a plurality of housings 803A, 803B, etc. The housing(s) 803, 803A, 803B is biocompatible with the body of the patient and is designed to be essentially inert when in the patient while protecting the patient from circuitry and other components internal to the housing(s). That is, the housing(s) can be hermetically sealed to be impervious to bodily fluids. The implantable cardiac device can include a connector header 805 to make electrical and mechanical connection with one or more leads 804. The housing can be formed of a suitable body-compatible material approved for medical use. Typically, the housing is formed with major opposed, and sometimes parallel, surfaces joined together by sides enclosing an interior chamber or cavity. The housing cavity receives the components, e.g., circuitry, sensors, energy source(s). The housing can have electrical feed-throughs extending therethrough and into the connector header or between the multiple housings. In an example, the housing is formed from a polymer. In an example, the housing is metal, such as titanium or aluminum. In the case of multiple housings, e.g., 803A, 803B, different components, such as circuitry, power sources (batteries, capacitors), memory, sensors, can be divided into various housings. While only shown as two housings 803A, 803B, it will be within the scope of the present disclosure to have more than two housings. In the illustrated example, the communication circuitry 820 is encased within housing 803A and the remainder of the circuitry is encased within housing 803B. In other examples, the batteries can be in the housing 803A.

Capacitor reformation circuitry 812 is provided to perform capacitor reformation functions to assist in prevention of loss of performance of the therapy energy source(s) 810 in the example with capacitors as part of the source(s) 810. Capacitor reformation circuitry 812 variously charges and discharges the capacitor(s) to help preserve the performance of the capacitor(s). In an example, the circuitry 812 schedules and executes capacitor reformation. Reformation can be important to numerous different capacitors, for example, electrolytic capacitors, tantalum-containing capacitors, and wet tantalum capacitors. In an example, the capacitor reformation circuitry 812 charges and discharges the capacitors. The capacitor reformation circuitry 812 periodically performs reformation at a set time interval. The set time interval can be stored in the memory 818. The time interval can also be adjusted by the reformation circuitry 812 depending on the performance of the capacitors. Although the principle purpose of capacitor reformation circuitry is to assure that the capacitors are function properly to provide a therapy signal, the capacitor reformation circuitry can also evaluate itself and any circuitry associated with charging the capacitors. The capacitor reformation circuitry 812 operates to transfer electrical energy from one energy source 816 (e.g., a battery) to the therapy energy source 810 (e.g., a capacitor or bank of capacitors). The capacitor reformation circuitry 812 then removes the electrical energy from the therapy energy source 810. In an example, the primary energy source 816 includes a rechargeable energy storage device and, hence, receives the charge from the therapy energy source 810 once during the reformation process. In a further example, the therapy energy source can include a set including a plurality of capacitors. The capacitors are sequentially charged by other capacitors in the set. For example, the first capacitor is charged from the energy source 816. The second capacitor is charged from the first capacitor. Once started, the first capacitor is charged by the $n^{th}$ capacitor, with n being the number of capacitors in the set. The circuitry 812 will monitor the amount of charge being supplied between capacitors to account for losses that occur when transmitting electrical energy to ensure that an adequate charge is provided to each individual capacitor for proper reformation.

Energy management circuitry 814A is to manage the energy usage in the implant device. The energy management circuitry 814A can operate to ensure separation of energy sources and to prevent flow of current from one energy source to the other when doing so would create a possible danger in the device. When the energy sources include rechargeable batteries, the energy management circuitry 814A can limit the energy flow, e.g., current flow (quantity and time) to assist in preventing failure of the batteries, an example of energy sources. The failure can be based on the chemistry of the batteries used in the device. In an example, the energy management circuitry can increase the charging time of the rechargeable energy source. When the energy source can handle a high energy, fast charge, then the energy management circuitry 814A can increase the quantity of electrical energy and/decrease the charging time.

Arbitration and decision circuitry 814B can act as the main controller for the device 800. It can arbitrate conflicts in operation between other circuitry of the device and determine which circuitry has priority over another. The circuitry 814B can include, but is not limited to, a processor (e.g., a central processing unit, logic circuits, application specific integrated circuit, logic gate arrays, etc.), cache memory, on-board random access memory, and on-board read only memory. The processor can be any one of numerous known general purpose processors or an application specific processor that operates in response to program instructions. The program instructions can be stored in memory 818, cache memory, on-board random access memory, on-board read only memory or combinations thereof.

Cardiac detection circuitry 814C operates to detect cardiac related signals in the subject's body. Any subject parameter that is useful in determining the cardiac health status can be sensed. Cardiac detection circuitry can operate either unipolar sensing or bipolar sensing. In an example, the circuitry 814 includes a sensing amplifier, which can include an amplifier module, a bandpass filter, a rectifier, and a threshold detector. The amplifier can have automatic gain control. The threshold detector can have auto-adjust threshold. Some of these structures can be integrated with each other.

Therapy output circuitry 814D is adapted to output a therapy signal from the device to provide therapy to a patient. The therapy output circuitry 814D can be electrically connected to the therapy energy source 810 to output electrical energy as part of the therapy signal. The therapy output circuitry 814D can also be electrically connected to the energy source 816.

Energy source 816 can include can include one or more of primary batteries or secondary batteries. For example, the energy source 316 may be a primary battery that would have a life of about 3 years, about 4 years or about 5 years. Additionally, the energy source 816 may have a reliable battery life after delivering shock therapy of about 1 month, about 2 months or about 3 months. The batteries can be rechargeable. In an example, some of the batteries are not rechargeable. Energy source 816 can optionally include at least one capacitor.

Leads 804 are to provide sensed data to the device 802 for analysis to detect patient parameters. The leads 804 can further provide therapy signals generated by the device 802 to a patient. The leads 804 can have cardioversion/defibrillation electrodes at an end distal from the housing. Other electrodes can be along the length of the lead 804. The electrodes can have a greater surface area than the body of the leads, e.g., greater than the cross section of the lead. The electrodes can be located in, on, or about the patient's heart. The leads 804 are implanted subcutaneously in a region of a patient's chest, e.g., the left chest. The lead(s) 804 can further extend transvenously and end adjacent or in the coronary sinus and great vein region of a heart or be located in the right ventricular chamber of the heart. The circuitry described herein can apply therapy signals between selected cardioversion/defibrillation electrodes. It is also within the scope of the present description to have at least one of the housing(s) act as an electrode.

Memory 818 can include volatile or non-volatile memory devices. These devices can store instructions to be accessed by circuitry described herein. The memory can also store sensed patient data related to the physiological parameters of a patient as well as derived data produced by the circuitry described herein that applies algorithms to the sensed data to diagnose the patient's condition and decide on the appropriate therapy.

Communication circuitry 820 is to receive data, such as programming data, and/or power from an external source, such a peripheral electrical device, e.g., a programmer. The communication circuitry 820 can further output data from implant device 800 to external electrical devices, which data can be sensed data or device performance data, which can be stored in memory 801. The communication circuitry 820 can wirelessly communicate with the external device. The communication circuitry 820 can include input/output (I/O) circuit and an antenna. The telemetry I/O circuit is coupled to the antenna, which can transmit and receive wireless, electromagnetic signals, e.g., radio frequency (RF) waves. The telemetry I/O circuit can function as a transmitter circuit or a receiver circuit. The telemetry I/O circuit can operate on one or more RF signals by modulating or demodulating the signals. The telemetry I/O circuit can further decode interrogation signals from the external communication device and provide such decoded signals to any of the circuitry of the device.

While the circuitry 808, 812, 814A, 814B, 814C, and 814D and sensor 806 are shown separately as discrete components, it will be understood that these components can be combined into various combinations of hardware and software instructions (tangible instructions stored on or in an apparatus for execution by a machine). It will further be understood that each of these components can communicate with each other to exchange data or store data to memory 818 or read instructions from or store data to memory 818. These connections are not shown for sake of ease of understanding. In an example, a bus, e.g., bus 708 of FIG. 7.

Figure 9:
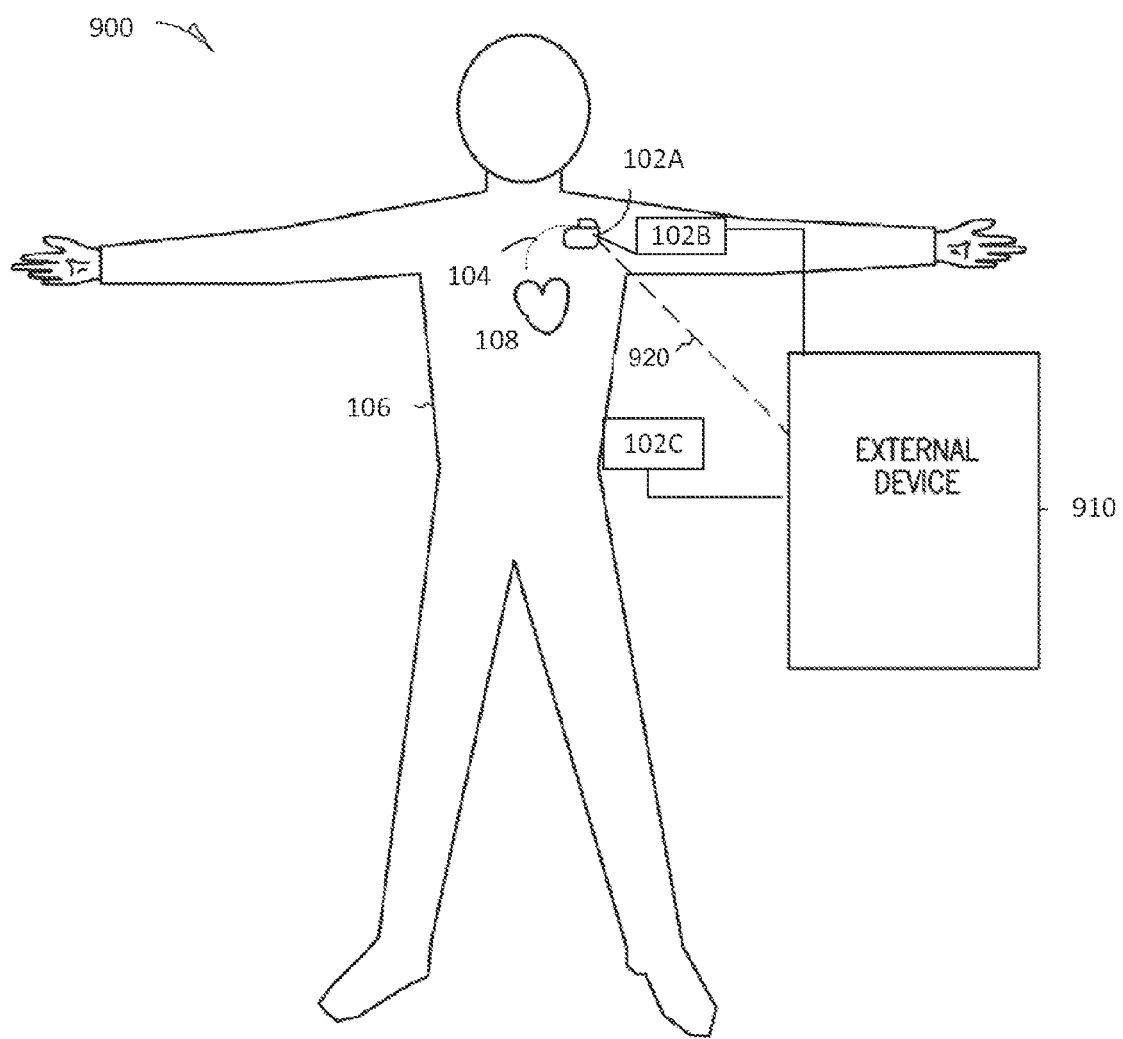
FIG. 9 is a schematic view of an implantable, medical system, according to some embodiments.

FIG. 9 shows a multiple housing system 900, which includes a first implantable housing 102A, a second implantable housing 102B, and a third, external housing 102C. It is within the scope of the present embodiment to include more than two implantable housings and more than one external housing. The housing 102A is connected to the leads 104 to sense physiological parameters of the subject, for example, a mammal or person 106. The physiological parameters can include indicators of cardiac performance of the subject. Housing 102A can include any of the circuitry or energy sources as described herein. In a specific example, the energy sources, such as batteries, are stored in at least one of the auxiliary housings 102B or 102C.

An external medical device 910 is positioned outside the subject's body 106. The device 910 includes a transceiver to wirelessly communicate with the implanted device 102A, which also include a wireless transceiver. The wireless signals 920 can be sent data between the device 910 and the device 102A. In an example, a trickle charge of electrical energy can be transmitted from external device directly to the implant 102A to supply electrical energy to its energy sources, e.g., a capacitor or a rechargeable battery. The device 910 can also be in electrical communication with the second implanted device 102B, for example, via a percutaneous system such as the system of FIGS. 12A-12C. The device 910 can also be in electrical communication with the external device 102C. The external device 910 can monitor the electrical charge being sent to any of the devices 102A-102C. Device 910 can act to prevent overcharging and/or overheating. In an example, battery temperature is monitored and fed back to device 910, which can adjust the amount of charge delivered. Device 910 can further control charge to any one of device 102A-102C so that runaway charging is prevented. Device 910 includes circuitry to vary charge delivery based on the state of the battery in any of the devices 102A-102C. Moreover, if it is known that the energy source is below a given threshold, then device, 910 can deliver high amount of energy at a fast rate. As temperature of energy sources of the device 102A-102C increases, then the device 910 will slow down the charge delivery, e.g., reduce current or the watts available for charging. Once the energy source is at a charge threshold, e.g., 90% charged or near full, then the device 910 will reduce the charge supplied to a trickle charge.

The external device 910 can transmit data received from the implanted medical devices 102A or 102B and external medical device 102C to a remote communication device, which can provide the data to a medical care provider. The external device 910, in an example, inductively communicates with the implanted devices 102A, 102B. Other radio frequency communication methods can be used. External device 910 can include a wand or other hand held device that is placed closely adjacent the patient's body and hence the implanted device 102A or 102B, which will wirelessly communicate with a single wireless hop from the implanted device and the external device 910. The external device 910 can be a bedside monitor that can be multiple feet away from the patient and implanted device. External device 910 can communicate with a further computer system to process the data. Device 910 can further trigger an alarm signal to be sent to a further communication device, e.g., a medical care provider's device such as a mobile phone, email system, text messaging device, paging, or other electrical communication. In the case where there is an external device 102C or one of devices 102A, 102B has a receptacle for a skin piercing probe (see e.g., FIGS. 12A-12C), the device 910 can connected to the device 102A, 102B, or 102C in a wired manner. The data could then be downloaded over the wired connection from the therapy devices 102A, 102B, or 102C to the external data process/storing device 910.

In an example, the device 910 includes a component locatable adjacent the patient. Device 910 can include a plurality of intermediate communication or data storage devices so that data is sent to the appropriate medical care provider. In an example, an intermediate device can be located in the hospital room with the patient to receive patient data stored on the implanted devices 102A or 102B. The intermediate device can be placed in the patient's home to receive patient data stored on the implanted devices 102A or 102B. In some embodiments, device 910 is a monitoring system that can include a distributed processing system with at least one processor comprising a tangible medium and a remote server.

The device 910 can operate to provide the alarm generated by the implanted device to the medical care provider, the patient or other people authorized by the patient via electronic communication. This will provide additional means to communicate the alarm from the implanted device to the patient or medical care provider.

In a further example, the implantable device 102A, 102B also senses and records its internal power level. It can send a signal, e.g., the alarm signal, indicating that the charge level is low. In the examples described herein with a rechargeable power source, the signal will indicate that the patient should recharge the power source or go to a medical facility to have the power source recharged. In an example, the skin piercing probe and receptacle embodiment show in FIG. 12 can be used to recharge the power source. In the embodiments described herein without a rechargeable power source, the low power signal will indicate that the patient should return to the medical care facility for evaluation of the device 102A, 102B and possible replacement.

Figure 10:
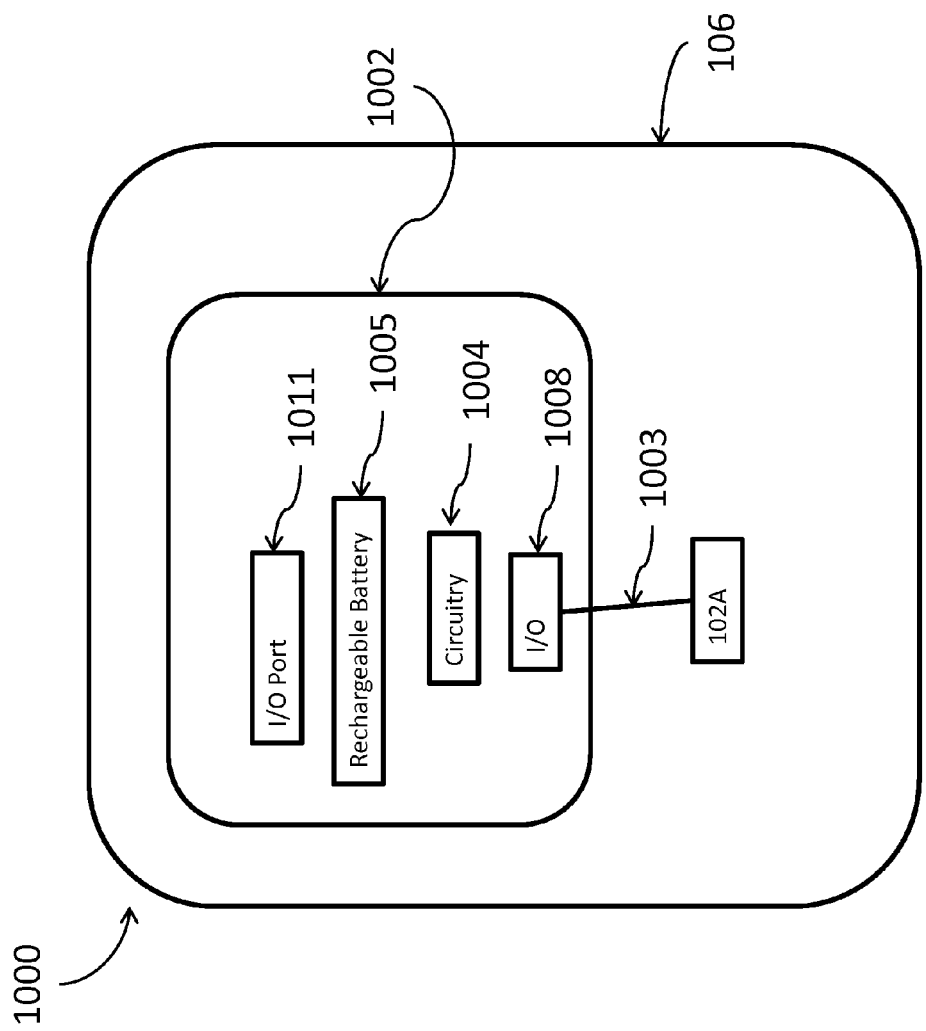
FIG. 10 is a schematic view of an implantable, medical system, according to some embodiments.

FIG. 10 shows an auxiliary housing system 1000 that can include housing 102A, which can be the same housing as shown in FIG. 9, and a further housing 1002. Housing 1002 can be an implantable structure that is biocompatible, e.g., inert, within the subject's body 106. The circuitry as described herein can be divided between the housing 102A and housing 1002. The circuitry in housing 102A and housing 1002 can electrically communicate through a communication line 1003. The line 1003 can be a wire that is implantable with the body of the subject. The wire can be similar to a lead but with connectors at each end to mate with a connector head on each of the housings. The line 1003 connects to an input/output port 1008 in the second housing 1002. Circuitry 1009 controls operation of the features of the second housing 1002, e.g., controls flow of data and/or power from the second housing 1002 to the housing 102A. Secondary housing 1002 further includes a second input/output port 1011, which is adapted to receive at least one of and possibly both power and data from outside the subject's body 106. In an example, the I/O port 1011 provides wireless, electromagnetic communication with external devices and circuitry. In a further example, the I/O port 1011 provides a mechanical and electromagnetic communication port. This example of port 1011 would require penetration of the skin of the subject's body 106. A housing 1002 with such a port 1011 would be implanted in a less sensitive location than the chest or pectoral region of the subject. Use of such a port with a probe is described in greater detail with reference to FIGS. 12A-12C.

The second housing 1002 can provide additional electrical power, e.g., through a battery 1005, to the system 1000. In the illustrated example of FIG. 10, the battery is rechargeable. In other examples, the batter is a non-chargeable battery. The battery 1005 can be recharged through port 1011 from power sources external to the housing 1002. Battery 1005 can also be used to transfer electrical charge to and from the power sources in the other housing 102A. In an example, housing 102A only has capacitors and not batteries as energy sources. In this example, the battery 1005 acts as the primary power source of the circuitry of housing 102A and charges the capacitors as needed for reformation and therapy.

Figure 11:
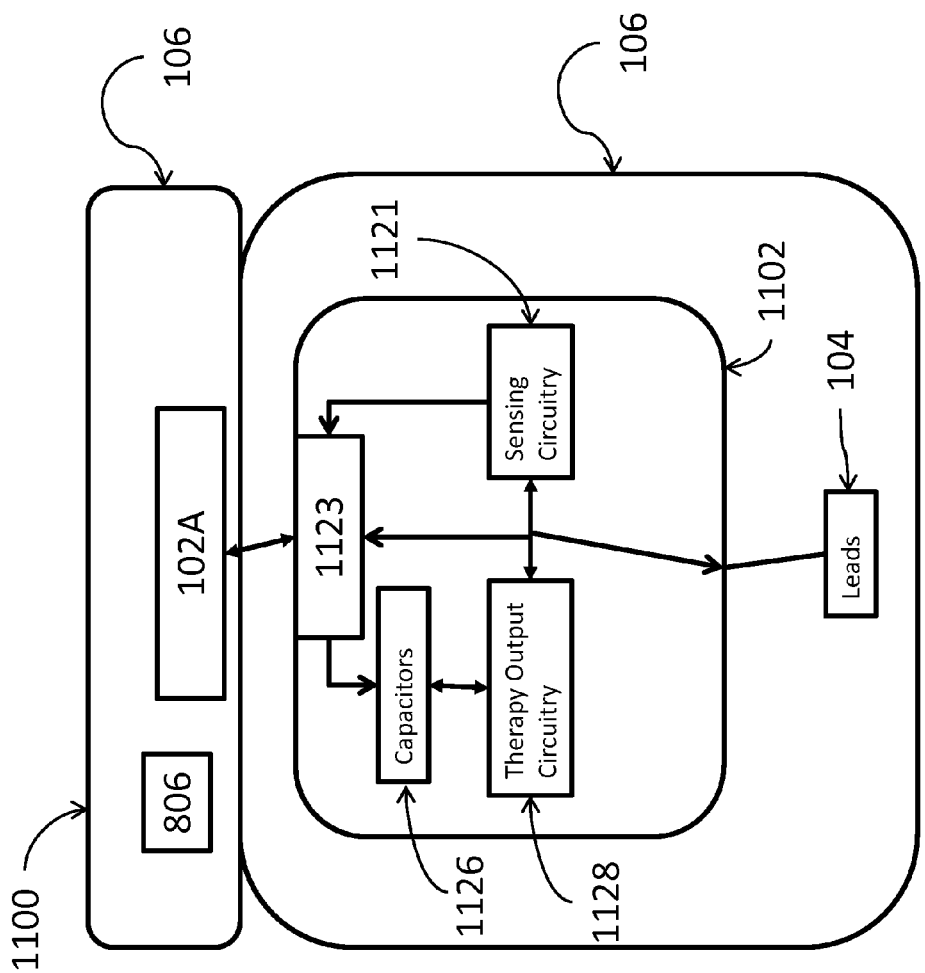
FIG. 11 is a schematic view of an implantable, medical system, according to some embodiments.

FIG. 11 shows an auxiliary housing system 1100 that can include housing 102A of FIG. 9 and housing 1102. The second housing 1102 is implanted in the subjects body 106 and connects with leads 104. The second housing 1102 includes sensing circuitry 1121 to sense the signals from the leads 104. These sensed signals are sent through an I/O port 1123 to the circuitry in housing 102A. The sensed signals are processed to determine the health status of the subject including the cardiac function and possible cardiac event. Housing 1102 further includes capacitors 1126 to provide a therapy signal, such as a defibrillation shock. Capacitors 1126 can be charged and reformed by circuitry in housing 102A through a communication line 1103 and I/O port 1123. Housing 1102 further includes a therapy output circuitry 1128 to control electrical discharge of the capacitors for therapeutic purposes.

The housing 102A, which includes arbitration and decision circuitry, cardiac detection circuitry, memory, power sources (e.g., batteries), capacitor reformation circuitry, etc. is positioned remote from the housing 1102. The housing 102A can be outside the subject's body 106. Optionally, the housing 102A can be implanted in the subject's body 106, preferably, apart from the housing 1102. Housing 102A can include the external port shown in FIG. 11 in housing 1002 and described in greater detail in FIGS. 12A-12C.

Figure 12A:
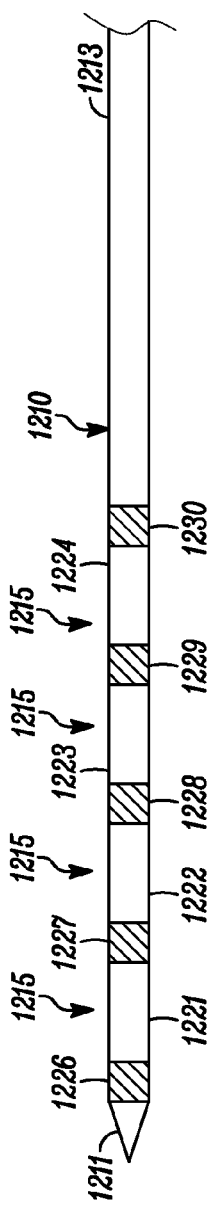
FIG. 12A shows a side view of a probe for use with an implantable, medical system, according to some embodiments.

FIG. 12A shows percutaneous system that includes a probe 1210 and a receptacle 1241. The probe 1210 that include a pointed tip 1211 at a proximal end and a distal end 1213 for connection to external circuitry (not shown) that provided data communication and power transmission. Probe 1210 is elongate and segmented along a length from the proximal end. The probe 1210 has a straight shaft body with a continuous contour, preferably smooth. Probe 1210 includes an electrical communication part 1215 adjacent the proximal end. The remainder of the elongate probe is not conductive. The electrical communication part 1215 includes a plurality of electrically conductive segments 1221, 1222, 1223, 1224 bound and separated by insulators (or electrical isolative segments) 1226-1230 to electrically separate the conductive segments 1221-1224. Each conductive segment 1221-1224 is positioned at a different longitudinal position of in the conductive part of the probe. In an example, a main shaft of the probe is principally made of a non-conductive polymer material. In an example, the polymer material of the probe shaft will operate to ensure better seal with the sealing membrane on top of the receptacle (See FIG. 12C). Insulators 1226-1230 can further contact membranes in a port to seal the port, see FIG. 12C for illustration and description. The probe 1210 can be essentially cylindrical, except for the tip 1211. In an example, the insulators 1226-1230 and the conductive segments 1221-1224 each have the same dimensions, e.g., outer surface shape and diameter, such that the probe can be inserted and withdrawn as comfortable as possible into the subject's body. The first segment 1221 and the second segment 1222 operate as positive and negative communication connectors to exchange data with implanted devices, e.g., circuitry in housings described herein. The third segment 1223 and the fourth segment 1224 act as power ports, e.g., positive and negative terminals or cathode and anode. A bus in formed in the probe 1210 to provide communication and power to the appropriate segment from external circuitry. The probe 1210 can further include an antibiotic coating on its outer surface. An antibiotic coating can further act to protect the subject (e.g., patient) from possible infections from a procedure that uses the probe.

The probe 1210 can be disposable and, in operation, is inserted like a syringe into the patient's body to the receptacle. In an example, the probe 1210 can include a light emitter such that the probe is visible beneath the skin. In an example, the light emitter is in the tip 1211 and can be a light emitting diode. The light emitter can be powered by the same power source as powered, conductive segments. In an example, the probe 1210 can include opaque material at the tip or along its shaft to allow visibility during medical imaging, e.g., X-Ray or fluoroscopy, viewing of the navigation of the probe inside the body of the patient.

Figure 12B:
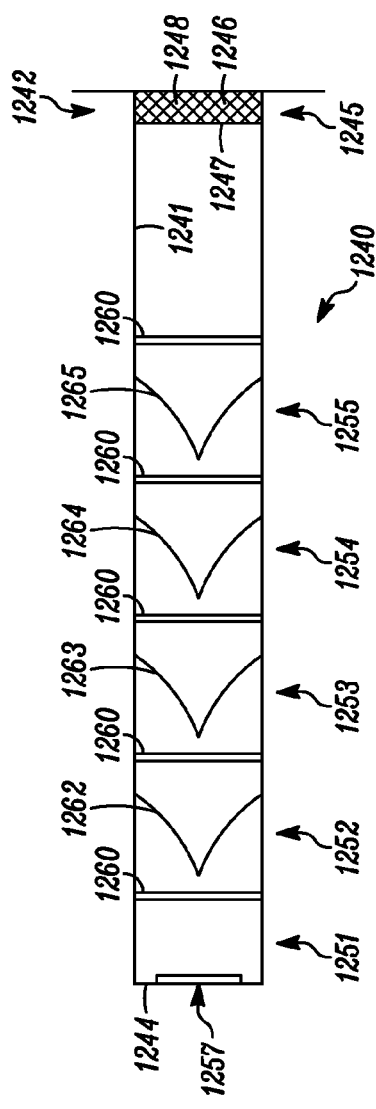
FIG. 12B shows a side, partial cutaway view of a port for use with an implantable, medical system, according to some embodiments.

FIG. 12B shows a port 1240 that includes a recess or receptacle 1241 with an open, proximal end 1242 of a surface of a housing and a closed, distal end 1244. The receptacle 1241 has a width or diameter greater than the width or diameter of the probe 1210 to receive the probe in the recess. The receptacle 1241 can be essentially cylindrical to form a female connector and the probe 1210 includes a male connector to mate with the female connector.

A membrane assembly 1245 is positioned at the proximal end to seal the open interior of the receptacle 1241. Membrane assembly 1245 include an outer membrane 1246 and in inner membrane 1247 that enclose a sealing fluid or gel 1248. In an example, the membranes 1246, 1247 are made of silicone. In an example, the outer membrane 1246 is thicker than the inner membrane 1247. In an example, the membranes are made of a rubber-like material. The membranes 1246, 1247 are easily penetrated by the tip end of the probe. Sealing fluid 1248 acts to assist in preventing penetration of bodily fluids or other moisture into the recess 1241 or allowing debris or fluids to escape from the recess if such material happens to enter the receptacle. The fluid 1248 inside the multi-layer membrane can include a quick-acting, medical-grade glue that activates upon contact with blood or other bodily fluid, causing fast closure of the hole in the membrane left behind by extraction of the probe 1210.

In an example, the receptacle 1241 is positioned on a housing as described herein, e.g., housing 102, 102A, 1002, 1102. In an example, the receptacle 1241 is on a header on the housing. The header can also include a port or multiple ports to mechanically and electrically connect the leads to the housings and appropriate circuitry. In another example, the housing includes a plurality of headers, e.g., one to have a charging receptacle or a receiving location for the probe and one for the leads. The header can define the receiving location for the probe from outside a body of a patient. The receiving location is at the open end of the receptacle 1241. The receiving location is viewable with medical imaging of outside a body of a patient to facilitate guidance and mating with the probe to the receiving location. In an example, the receiving location includes an opaque material that makes it visible under the medical imaging. An example of the medical imaging includes X-ray imaging. The probe at the receiving location can deliver at least one of energy and data to the implanted medical device through the receiving location. The probe mates with the receiving location by insertion through a patient's skin. The probe includes multiple segments to act as cathode connection and anode connection for energy delivery. The probe can further include multiple segments which can provide digital communication.

The receptacle 1241 includes individual segments 1251-1255 separated from each other by membranes 1260. Membranes 1260 operate to seal the interior of the receptacle segments from each other. In an example, the membranes 1260 are made of silicone. The receptacle segment 1251 at the distal end of the recess is bound by one membrane and is closed at one end. An activation switch 1257 is positioned at the closed end of the recess in the segment 1251. The switch 1257 can operate to disable the contacts until the probe is completely inserted in the housing and all connections are made with the segments of the probe receptacle and the switch is activated by the tip of a probe. The switch 1257 is activated only when it is contacted or depressed by the probe 1210 being fully inserted into the receptacle 1241. The switch 1257 holds the electrical contacts in a deactivated electrical state until the probe is fully inserted.

Receptacle segments 1252-1255 include contacts 1262-1265 between the membranes 1260 bounding the segments. The membranes 1260 operate to electrically isolate the contacts 1262-1265 in the case where fluids enter the recess. The contacts 1262-1265 can be conductive fibers or metal plate material that will yield to insertion of the probe and urge against the surface of the probe. In an example, contacts 1262-1265 can include laminates of thin electrically conductive materials or meshes of fibers. Use of meshes, plates or other relatively large area contact, will assist in preventing corrosion, for example, to due arcing and plasma, and reducing overheating, which can lead to further corrosion. Corrosion should be avoided as much as possible as mechanical breakdown can occur, which will degrade electrical performance. Additionally the corrosion inside the receptacle may introduce potential hazards to patients. Accordingly, the contacts 1262-1265 are designed to handle the electrical energy during electrical communication. Additionally I have current limiting circuitry inside the device that ensures the current pull is consistent with the capabilities of the system as a whole. The contacts 1262-1265 extend inwardly into the open interior of the recess and are to yieldably press to the center of the recess. The contacts 1262-1265 have mechanical push and makes tight mechanical connection with the probe 1210 when inserted in the probe receptacle (see FIG. 12C). In an example, the contacts 1262-1265 are biased into the position shown in FIG. 12B. In an example, the switch 1257 is activated and the contacts tested to be in electrical communication with the probe before data is exchanged between the probe and the implanted device through the receptacle contacts 1262-1265. The contacts 1262-1265 are disabled until the probe 1210 is completely inserted in the housing and all connections are made with the segments of the probe receptacle 1241.

The membrane assembly 1245 further acts to protect the contacts 1262-1265 from electrical signals in the subject's body. The membrane assembly 1245 electrically isolates the contacts 1262-1265, along with the body of the receptacle, from electrostatic shocks or a defibrillation signals.

Figure 12C:
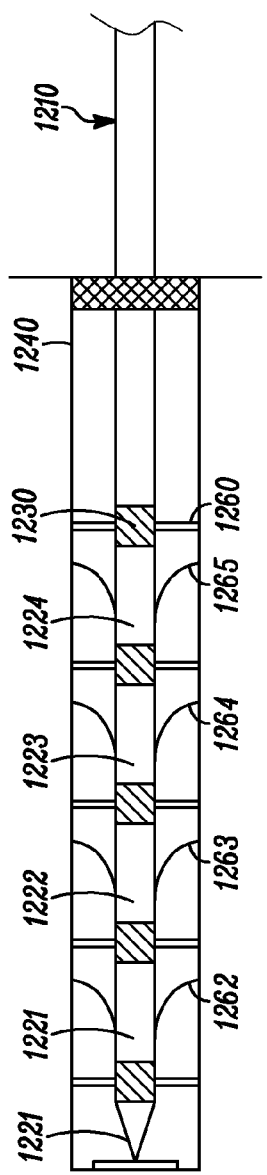
FIG. 12C shows a view of the probe in the port for use with an implantable, medical system, according to some embodiments.

FIG. 12C shows the probe 1210 inserted through the subject's skin and other body tissues into the receptacle 1241. The tip 1211 pierces the membrane assembly 1245, pierces the membranes 1260 and separates each of the contacts 1221-1224 as the probes moves into the receptacle 1241. Probe tip 1211, when the probe is fully inserted in the receptacle, contacts the switch 1257 to allow activation of the contacts 1262-1265. When fully inserted, the insulators 1226-11230 are longitudinally aligned with a respective membrane 1260 such that each paired contact 1262-1265 and conductive segment 1221-1224 are isolated from each other prior to either power being delivered from the probe segments 1223 and 1224 to the contacts 1264 and 1265 to recharge the energy sources of the implanted device. The isolation also occurs prior to any data being exchanged between the data probe segments 1221, 1222 and the data contacts 1262 and 1263 of the receptacle. In an example, the data and power signals are exchanged at different times to prevent corruption of the data, which can be used to diagnose the subject or to operate the implant, or prevent power deliver to data circuitry, which may not be able to handle a power signal.

The electrical communication system as shown in FIGS. 12A-12C requires the piercing the skin in order to mate the probe with the receptacle with the device, this procedure will preferable be done in a medical setting, e.g., the physician's office. The requirement that the patient be at the medical setting can assist to ensure proper supervision of the patient's medical status by a physician and a technician that help would guarantee patient monitoring and hopefully, improve compliance and patient outcome. Such routine intervention by medical experts and specialists will reduce issues with patient compliance and help ensure that the device is available to the patient at all times.

The receptacle 1241 can also have a light unit at the recess to indicate where the probe 1210 is to be inserted to assist in guiding the probe to the receptacle. In an example, the light turns off when the probe is successfully inserted into receptacle. In an example, the light turns on when the switch in the receptacle is activated to indicate that the mechanical connection has been made. The light can remain illuminated if there is also an electrical communication between the probe and receptacle. If the electrical communication is faulty the light can flash or turn off. In an example, the light remaining on indicates that the electrical communication continues. The light can further indicate when charging is complete. Once charging is complete, the probe can be removed.

The electrical communication system as shown in FIGS. 12A-12C provides many benefits. The unitary size and essentially smooth, continuous outer surface of the body of the probe allows for the ease of insertion into the subject's body and protects the contacts in the receptacle from unnecessary wear. The probe further creates clean, smooth penetration cites into the various membranes to extend their useful life. The use of multiple electrically conductive segments can increase the data rate and allow simultaneous data and power transmission. Moreover, the electrical power transmission receptacle contacts and probe segments can be made larger to increase the contact area for improved electrical energy transmission. A further advantage is the mechanical connections between the conductive probe segments and the receptacle contacts, which can provide reliable data and power transmissions. While shown and described as having both data and power contacts, it is within the present disclosure to have more than two of each type of segment or have all power segments depending on the particular needs of the system. For example, wireless data transmission between the implant and an external device can handle the data communication whereas the power transmission is handles by the presently described probe and receptacle system.

Referring to FIGS. 13A-13G, various schematic views of implantable devices 1300A-1300M for treating a patient at risk for a cardiac episode are shown, according to some embodiments. It will be recognized that similar components in the medical devices 1300A-1300G use a numbering scheme with the first two numbers representing the figure number with the other numbers and suffix, if any, being the same as those used in FIGS. 3-6 and 14-19. For example, the housing is labeled as 302 in FIGS. 3 and 1302A-1302C respectively in FIGS. 13A-13G. The numbering scheme represents that each of these views includes similar features unless explicitly stated otherwise in a specific embodiment with regard to a specific figure.

Figure 13A:
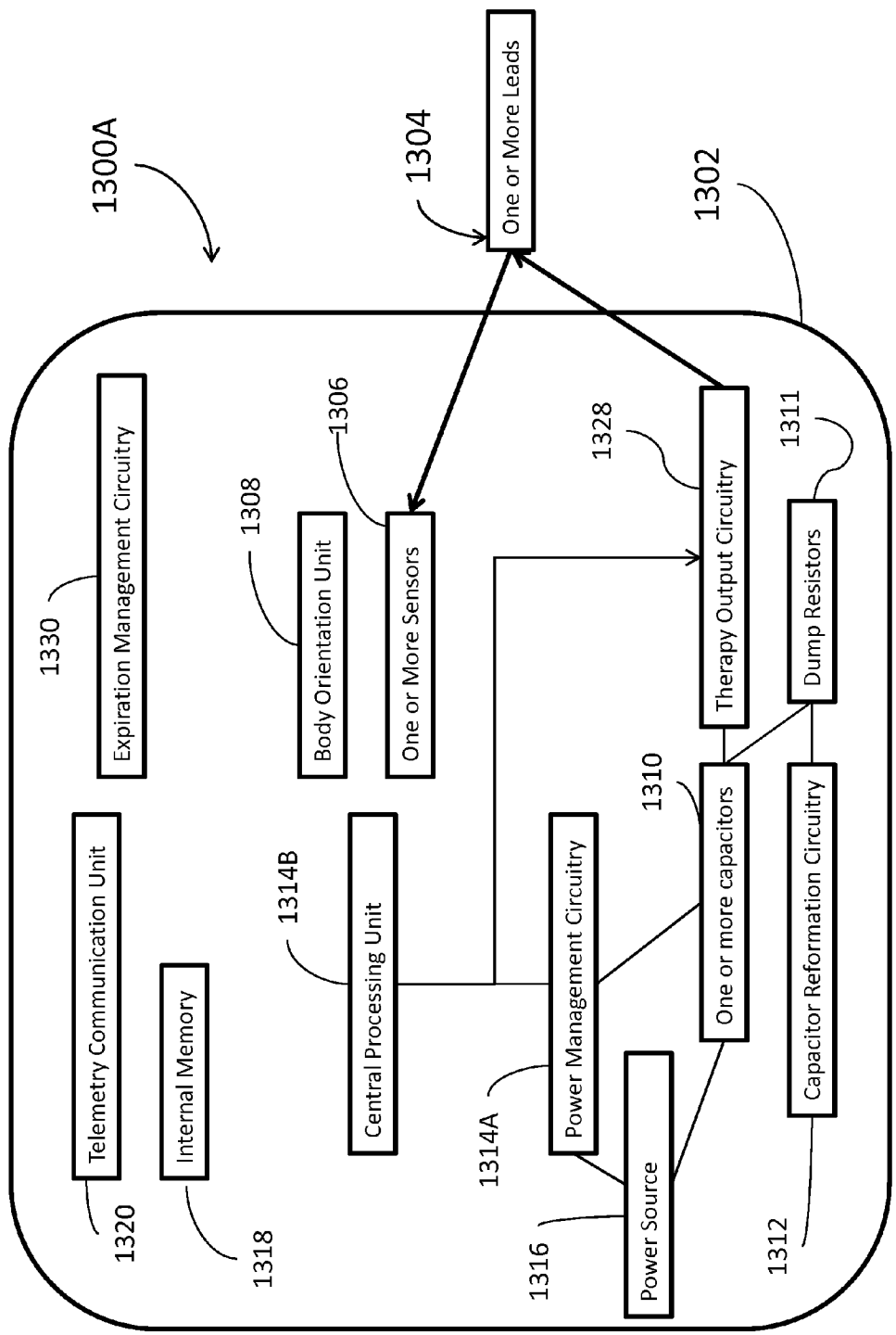
FIGS. 13A-13G show various schematic views of an implantable device for treating a patient at risk for a cardiac episode, according to some embodiments.
Figure 13B:
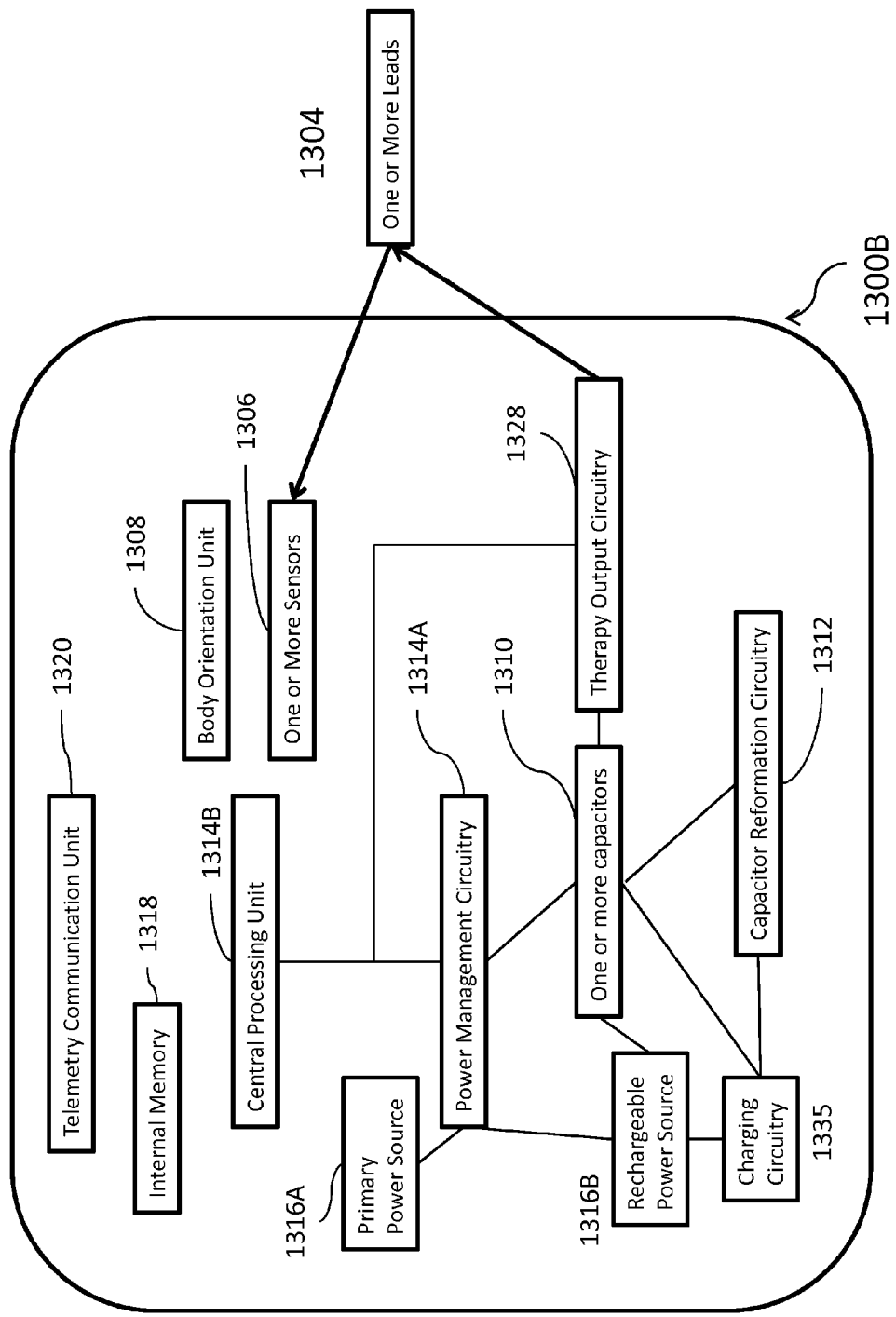

The devices 1300A, 1300B, and 1300C can include a housing 1302 including an integrated lead and/or connected to one or more leads 1304, which extend from the housing 1302 and are adapted to electrically interact with a patient's body to sense physiological parameters or to deliver therapeutic signals to a patient. The housing 1302 can also include sensors to sense physiological parameters or to deliver therapeutic signals to a patient. The sensors can also sense cardiac activity and the physical activity of the patient. The housing 1302 of devices 1300A, 1300B, and 1300C is a single housing that encases all of the electronics and power sources for implantation into the body of a patient. Device 1300A (FIG. 13A) includes one or more sensors 1306, a body orientation unit to detect orientation of the patient's body, one or more capacitors to store electrical energy for output as a therapeutic signal (e.g., defibrillation signal), dump resistors 1311 to bleed excess electrical energy as needed, capacitor reformation circuitry 1312, a power source 1316 (e.g., one or more batteries such as the batteries shown in FIGS. 20-24), power management circuitry 1314A to control electrical power usage and transfer of power between units in the device 1300A, processing circuitry 1314B, memory 1318 to store data and instructions for executions by units in the device 1300A, communication unit 1320, expiration management circuitry 1330 to control the expiration of the device 1300A, therapy output circuitry 1328, all encased in housing 1302. Each of these units in the housing 1300A can be in electrical communication with each other either by a direct electrical connection, a common bus, or through other units. For ease of illustration all of the electrical connections are not shown in FIG. 13A. Device 1300B of FIG. 13B is similar to device 1300A except device 1300B includes a plurality of power sources, which in the illustrated embodiment of FIG. 13B includes a bifurcated power source with a primary power source 1316A and a rechargeable power source 1316B. The primary power source 1316A can be a non-rechargeable battery and can be used to power the processor 1314B, the sensors 1306 and body orientation unit 1308. The rechargeable power source 1316B is used to power the signal generator functions, inclusive of the capacitors 1310, power management circuitry 1314A, therapy output circuitry 1328 and capacitor reformation circuitry 1312. The use of the rechargeable power source 1316B can provide more efficient power use in the device 1300B and provide for faster charging of the capacitors 1310 than conventional chemical batteries used in implanted medical devices.

Charging circuitry 1335 is electrically connected to the capacitor reformation circuitry 1312, the one or more capacitors 1310, and the rechargeable power source 1316B. The charging circuitry 1335 can operate to transfer electrical energy from an external power source to the rechargeable power source 1316B. The charging circuitry 1335 can operate to transfer electrical energy between the one or more capacitors 1310, capacitor reformation circuitry 1312 and the rechargeable power source 1316B.

Figure 13C:
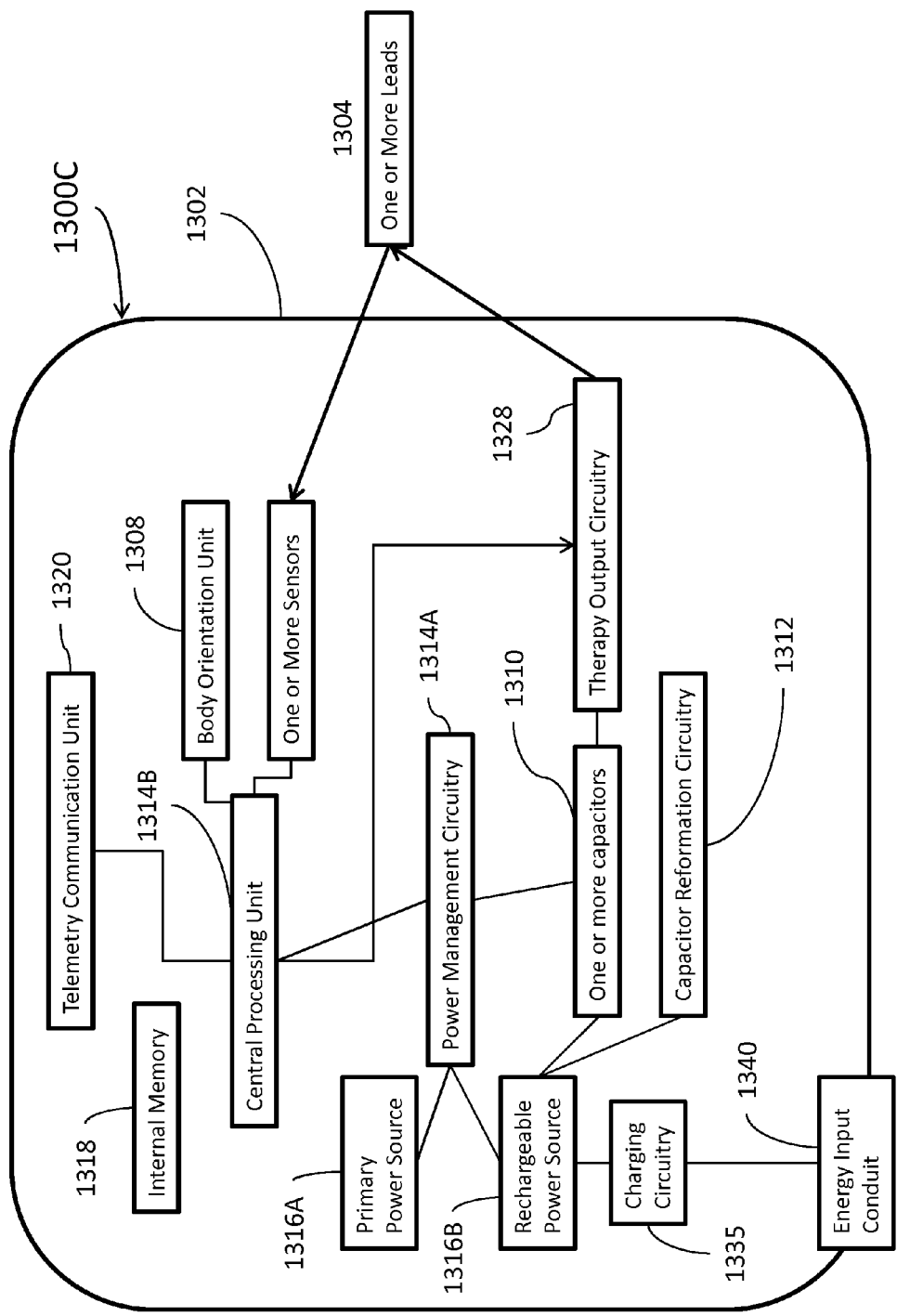

Device 1300C of FIG. 13C is similar to device 1300B expect the charging circuitry 1335 is connected between the rechargeable power source 1316B and an energy input conduit 1340. In an example, the energy input conduit 1340 is the receptacle shown in FIGS. 12B and 12C.

Devices 1300D-1300G (FIGS. 13D-13G) show embodiments with multiple housings 1302A and 1302B that house various units and components of the devices. In various embodiments, some components of the ICD devices described herein are in one housing and other components are in other housings. The components can communicate with other components in another housing. Referring to FIG. 1300D, the first housing 1302A encases one or more sensor circuitries 1306, which can be in electrical communication with the leads 1304. First housing 1302 further encases the body orientation unit 1308, a processor 1314B, a primary power source 1316A, memory 1318, and a telemetry communication unit 1320. A second housing 1302B encases control circuitry 1314E, a primary power source 1316A, power management circuitry 1314A, a secondary, rechargeable power source 1316B, one or more capacitors 1310, therapy output circuitry 1328, which can be in electrical communication with the one or more leads 1304, charging circuitry 1335, and capacitor reformation circuitry 1312. The power sources and related circuitry are in the second housing 1302B. Second housing 1302 can be the same as the housings 102B or 102C shown in FIG. 9. The second housing 1302B can also include systems as described in FIGS. 14-22 below. The circuitry in the two housings 1302A and 1302B can be in electrical communication with each other over a communication connection 1331. Communication connection 1331 allows power, data or instructions for the device to be transferred between circuitries in the two housings 1302A, 1302B. Accordingly, the two housings need not be implanted in the same location in the patient's body. For example, the two housings can be remote from each other, e.g., as shown in FIG. 9. The present embodiments that have two housings 1302A, 1302B can allow the housing with the power sources and related circuitry can be replaced without accessing the pouch in the patient's upper chest in which the first housing with the sensors and processor.

Figure 13D:
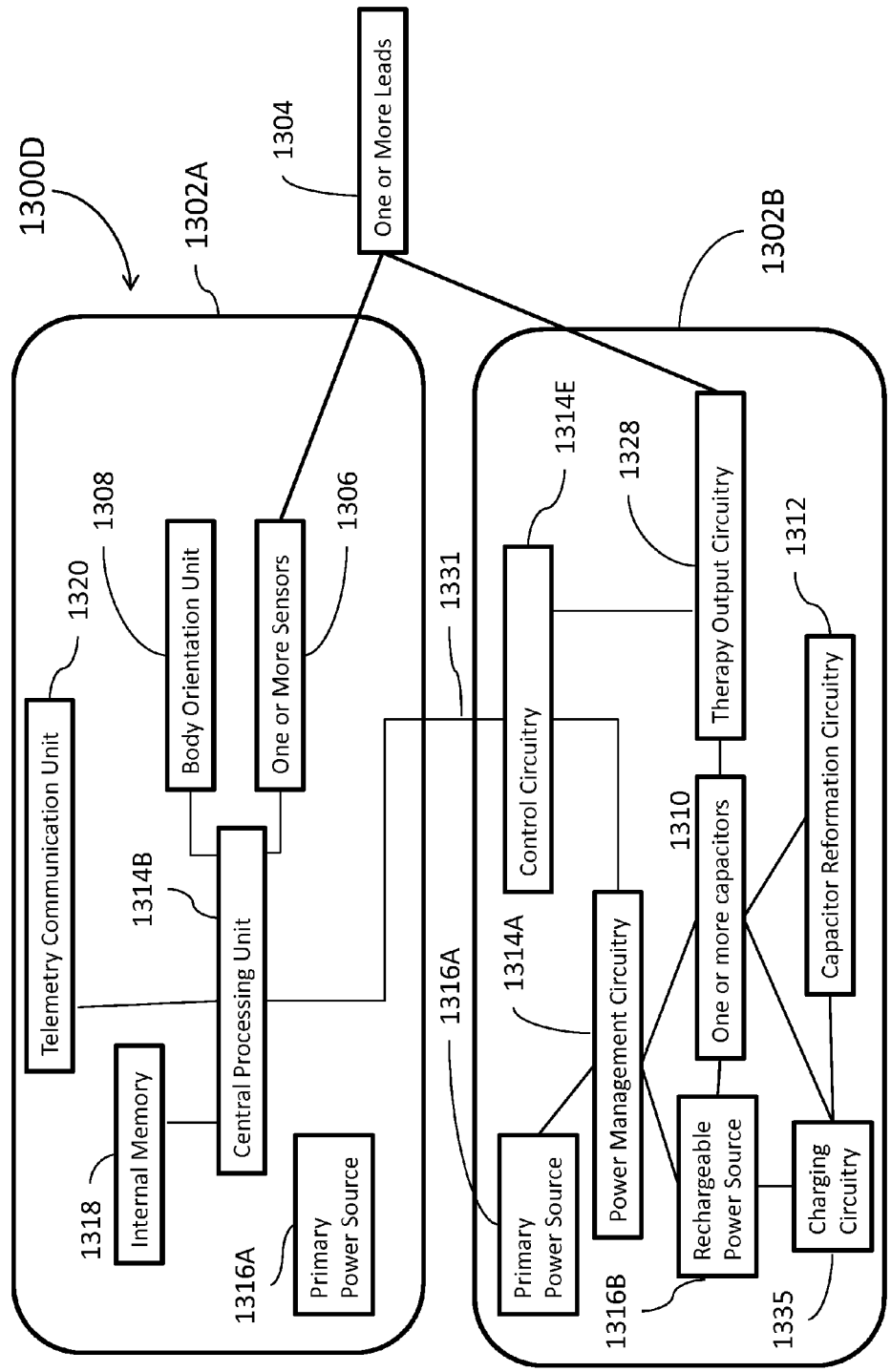
Figure 13E:
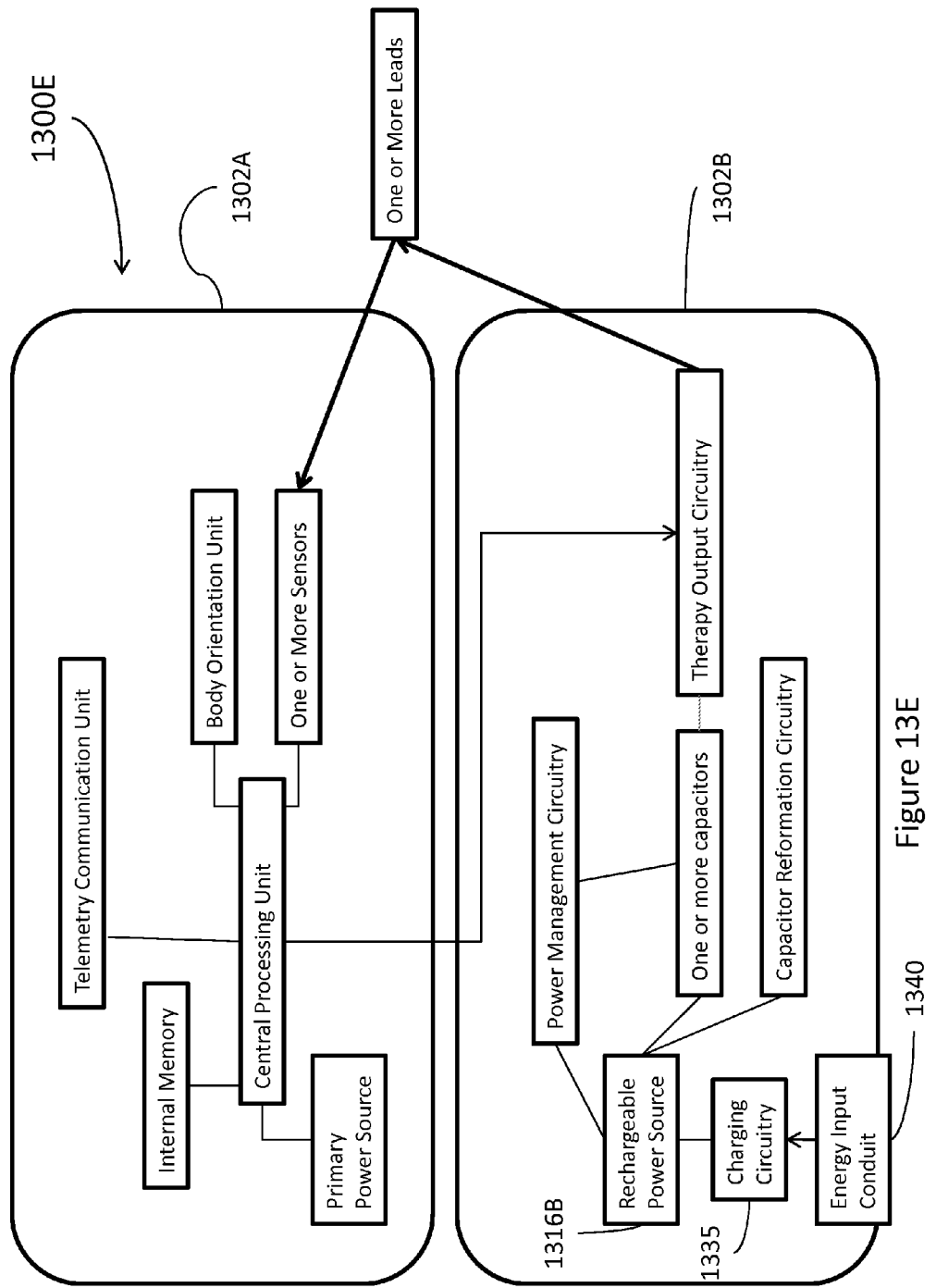

FIG. 13E shows a further multiple housing embodiment with housings 1302A and 1302B, which is similar to the device 1300D of FIG. 13D. However, the second housing 1302B includes a receptacle 1340 to receive energy input from an external source. In an embodiment, the receptacle 1340 is the same as the receptacle described with regard FIGS. 12B and 12C. The receptacle 1340 can receive a probe to engage the charging circuitry 1335 to charge the rechargeable power source 1316B. In an example, the power housing 1302 is adjacent the skin so that a needle-like probe can pierce the skin and electrically engage the receptacle.

Figure 13F:
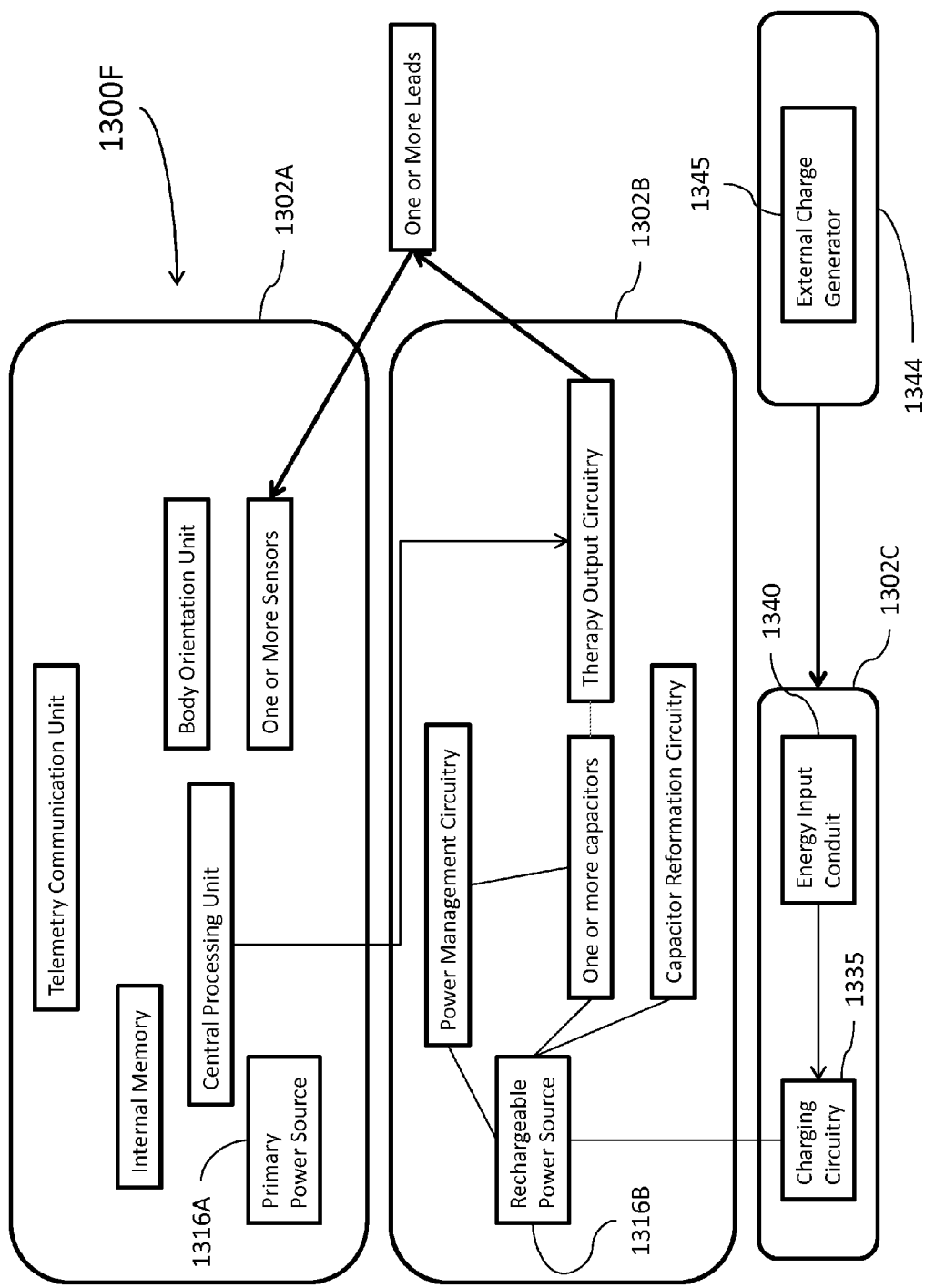

FIG. 13F shows a further multiple housing embodiment with housings 1302A, 1302B and 1302C. In this example, the processing/sensing, first housing 1302A is the same as those described in FIGS. 13D-13E. The second housing 1302B includes power management circuitry, one or more capacitor, a therapy output circuitry, capacitor reformation circuitry, and a rechargeable power source. The charging control circuitry 1335 and the energy input receptacle 1340 are moved to a third, energy input housing 1302C. The charging circuitry 1335 is electrically connected to the rechargeable power source 1316B. The receptacle 1340 can be the same as that described with regard to FIG. 13E. An external charge generator 1345 is in an external housing 1344. External housing 1344 is not designed to be implanted into a patient's body. The external charge generator 1345 can provide a charge through a probe (FIGS. 12A and 12C) that can pierce the patient's skin to engage the implantable housing 1302C.

Figure 13G:
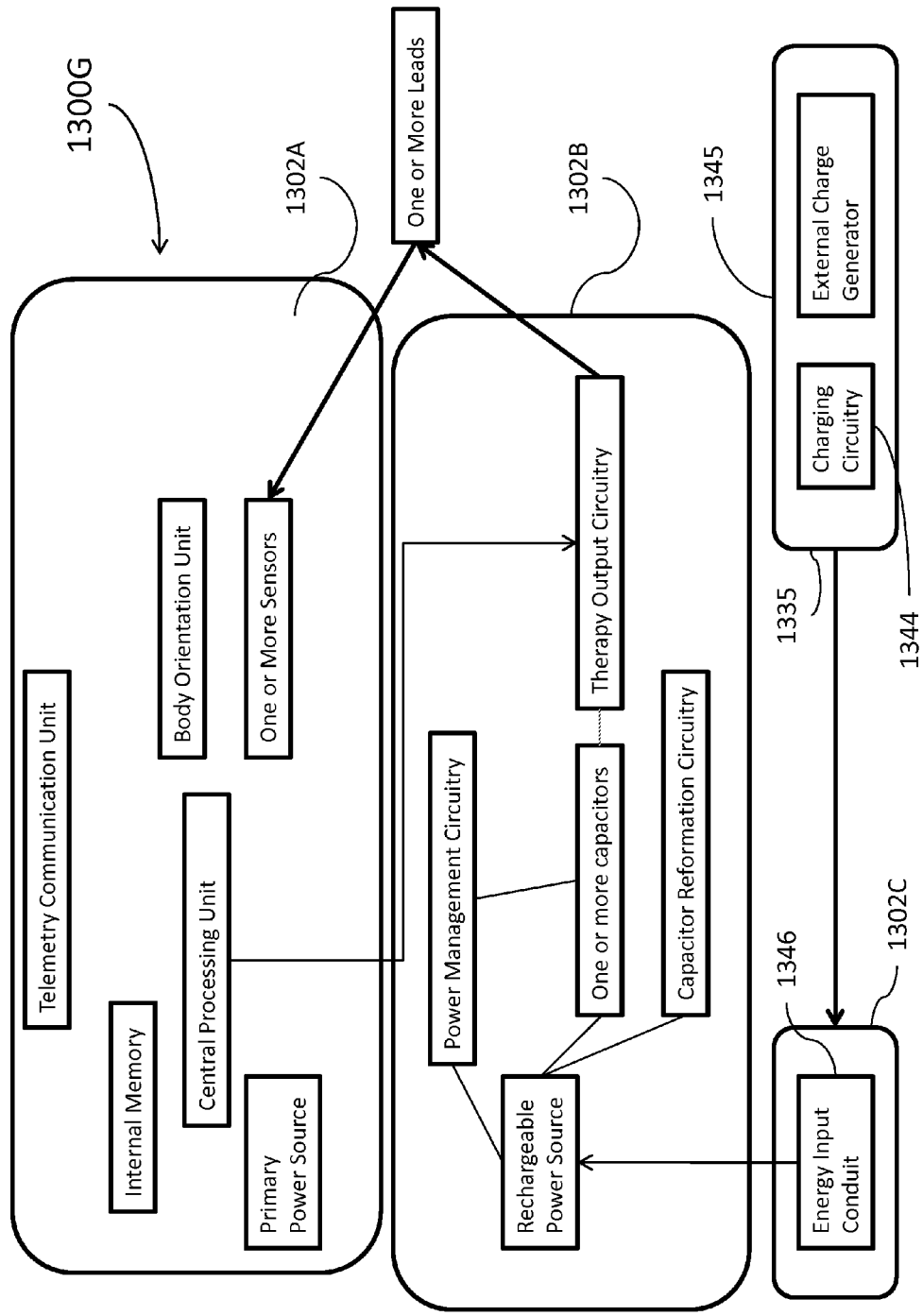

FIG. 13G shows a further multiple housing embodiment with housings 1302A, 1302B and 1302C. In this example, the processing/sensing, first housing 1302A is the same as those described in FIGS. 13D-13F. The second housing 1302B includes the same components as those described with regard to FIG. 13F. However, the energy input receptacle 1335 is positioned in the third housing 1302C. The external housing 1344 holds the charging control circuitry 1335 and the external charge generator 1345. In an example, the third housing is an implantable housing, which can be positioned separately from the first and second housings 1302A, 1302B.

The therapy output circuitry 1328 can include an expiration unit that can stop the output of a therapy signal from the device 1300A-1300G. The expiration unit can be instructions executed by a machine, e.g., instructions in circuitry, to end the output capability of the implantable device. The expiration unit can include a fuse, an antifuse, transistors, or operational amplifiers to end the ability of the device 1300A-1300G to output a therapy signal.

FIGS. 14-19 show various embodiments of implantable medical devices 1400-1900, according to various embodiments. It will be recognized that similar components in the medical devices 1400-1900 use a numbering scheme with the first two numbers representing the figure number with the other numbers and suffix, if any, being the same as those used in FIGS. 3-6 and 14-19. For example, the housing is labeled as 302 in FIG. 3, 1302 in FIGS. 13A-13G, and 1402 in FIG. 14.

In use, the primary power source 1316A can be used to power various monitoring and sensing functions with the rechargeable power source 1316B providing power for a therapy signal. The rechargeable power source 1316B can charge the therapy signal powering capacitors faster than conventional chemical batteries. However, if the rechargeable power source does not have sufficient electrical power to charge the capacitors for a sufficient energy for a therapy signal, then the primary power source 1316A can also be used to charge the capacitors even if the time to charge the capacitors increases relative to using the rechargeable power source alone. In cases where capacitor charge time is of importance, then both the non-rechargeable power source 1316A and the rechargeable power source 1316B can be used to charge the capacitors. In another embodiment, the rechargeable power source 1316B is designed to store sufficient charge for capacitor reformation but may not have sufficient charge to charge capacitors for a therapy signal. In this case, the non-rechargeable power source 1316A can store sufficient charge to run the other circuitry and charge capacitors for the therapy signal output by the device 1300A-1300G.

FIG. 14 shows an implantable device 1400 in an implantable housing 1402. The housing 1402 encases a power source 1416, capacitor reformation circuitry 1412, and a therapy output circuitry 1428. A plurality of high voltage capacitors 1410A, 1410B are provided to store sufficient energy to output a high voltage therapy signal. An electronic switch circuitry 1451 is positioned between the capacitor reformation circuitry 1412, high voltage capacitors 1410A, 1410B, therapy output circuitry 1428, and dump resistors 1452. The switch circuitry 1451 operates to control flow of electrical energy between the various components. The dump resistors 1452 can be used to bleed excess energy from the capacitors 1410A, 1410B, e.g., dissipate energy as heat. The dump resistors 1452 are used in this embodiment to remove charge from the capacitors 1410A, 1410B, if there are charged with sufficient energy for a therapy signal but the therapy is aborted, e.g., the body orientation unit determines that a shock signal should not be output.

FIG. 15 shows an implantable device 1500 in an implantable housing 1502. The housing 1502 encases a rechargeable power source 1516B, capacitor reformation circuitry 1512, and a therapy output circuitry 1528. A plurality of high voltage capacitors 1510A, 1510B are provided to store sufficient energy to output a high voltage therapy signal. An electronic switch circuitry 1551 is positioned between the capacitor reformation circuitry 1512, high voltage capacitors 1510A, 1510B, therapy output circuitry 1528, and charge recovery circuitry 1552. The switch circuitry 1551 operates to control flow of electrical energy between the various components. Charge recovery circuitry 1552 provides an electrical pathway from the electronic switch 1551 to rechargeable power source 1516B. The electrical energy fed to the capacitors 1510A, 1510B for either reformation or for an aborted therapy signal can be fed back to the rechargeable power source 1516 for later use by the device 1500. This embodiment can use the energy in the device 1500 more efficiently than the device 1400, which may waste energy as heat through its resistors 1452. Device 1500 can use energy for reformation, pre-charging for therapy, fully therapy charge that is aborted for other uses.

Figure 16:
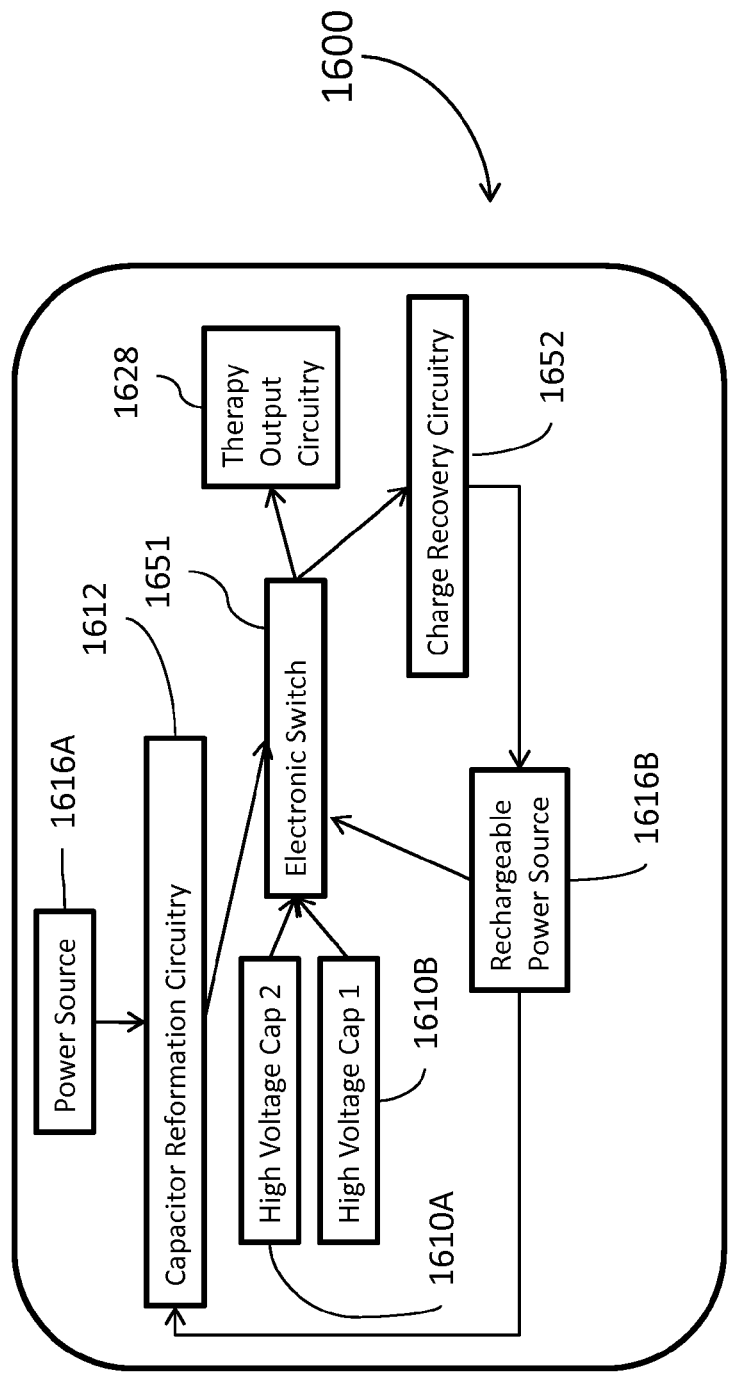

FIG. 16 shows an implantable device 1600 in an implantable housing 1602. The housing 1602 encases a plurality of power sources, here illustrated as a power source 1616A and rechargeable power source 1616B. In an example, power source 1616A is a non-rechargeable battery. Housing 1602 further encases capacitor reformation circuitry 1612, and a therapy output circuitry 1628. A plurality of high voltage capacitors 1610A, 1610B are provided to store sufficient energy to output a high voltage therapy signal. An electronic switch circuitry 1651 is positioned between the capacitor reformation circuitry 1612, high voltage capacitors 1610A, 1610B, therapy output circuitry 1628, and charge recovery circuitry 1652. The switch circuitry 1651 operates to control flow of electrical energy between the various components. Charge recovery circuitry 1652 provides an electrical pathway from the electronic switch 1651 to rechargeable power source 1616B. The electrical energy fed to the capacitors 1610A, 1610B for either reformation or for an aborted therapy signal can be fed back to the rechargeable power source 1616B for later use by the device 1600. This embodiment can use the energy in the device 1600 more efficiently than the device 1400, which may waste energy as heat through its resistors 1452. Device 1600 can use energy for reformation, pre-charging for therapy, fully therapy charge that is aborted for other uses. In addition to the rechargeable power source 1616B, the power source 1616A can provide the consistent electrical energy of a chemical battery. In this example, the power source 1616A provides electrical energy to the circuitry 1612 and, once the energy leaves the primary power source 1616A, it recirculates in the circuitry 1612, capacitors 1610A, 1610B, switch 1651, 1652 and rechargeable power source 1616B until the energy is dissipated due to internal resistances or output by the therapy output circuitry 1628. When a therapy needed event is determined, the primary power source 1616A and the rechargeable power source 1616B can be used to charge the capacitors 1610A, 1610B to provide sufficient energy for a therapy signal output by circuitry 1628. The use of multiple power sources to charge the output capacitors 1610A, 1610B can shorten the time it takes to prepare the device 1600 to output a therapy signal.

Figure 17:
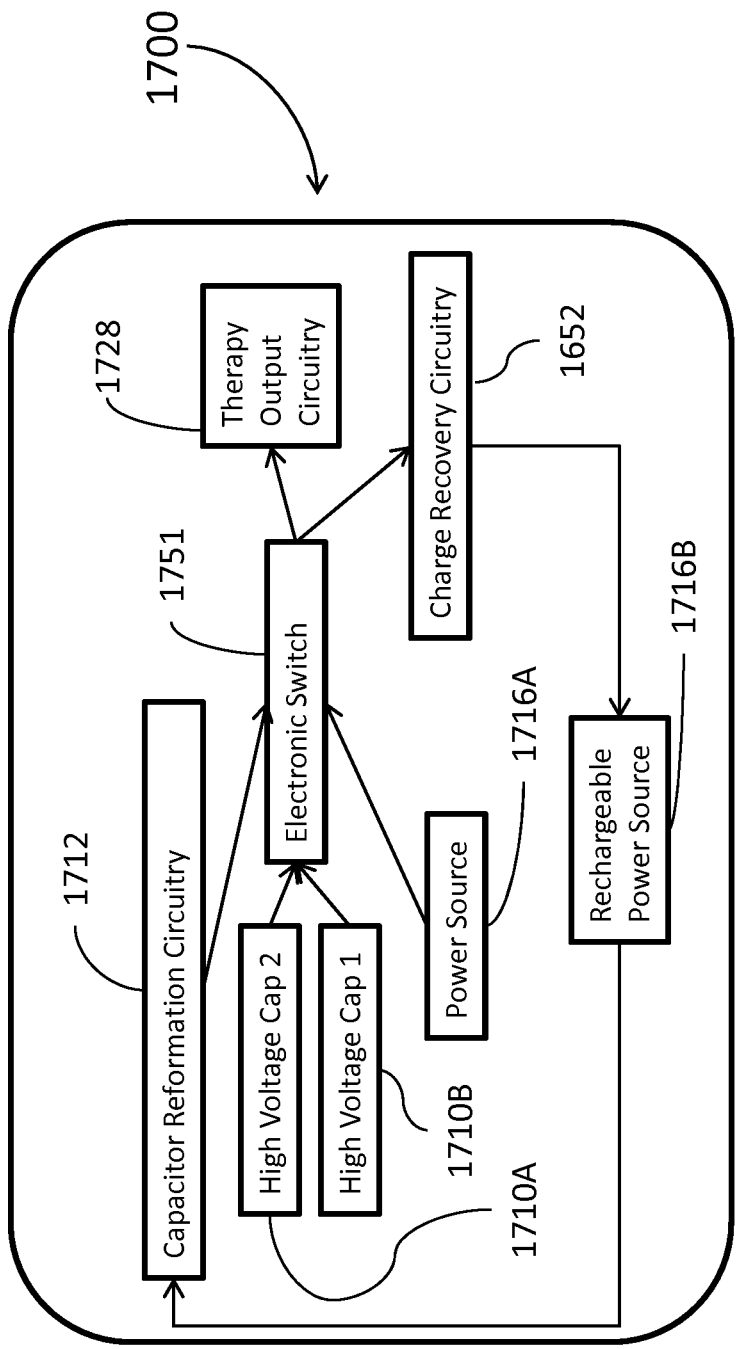

FIG. 17 shows an implantable device 1700, which is similar to device 1600 except that the power source 1716A is connected to the electronic switch and not to the capacitor reformation circuitry 1712. The power source 1716A can be a non-rechargeable battery. Unlike device 1600, the power source 1716A cannot be used for reformation or for charging the capacitors. Power for capacitor reformation is delivered by the rechargeable power source 1617B. In an example, the power source 1716A is used to only power the rechargeable power source 1716B. The rechargeable power source 1716B also powers the capacitors 1710A, 1710B for a therapy signal.

In another embodiment, the power source 1716A, e.g., the primary battery, is used to charge the capacitors 1710A, 1710B for delivery of a therapy signal via therapy output circuitry 1728. In an example, the switch circuitry 1751 can use the power source 1716A to charge a first capacitor 1710A and the rechargeable power source 1716B to charge another capacitor 1710B. This will reduce the charge time for the capacitors 1710A, 1710B as two different power sources are dedicated to different capacitors or groups of capacitors (if capacitor 1710A, 1710B individually represent more than one capacitor).

Figure 18:
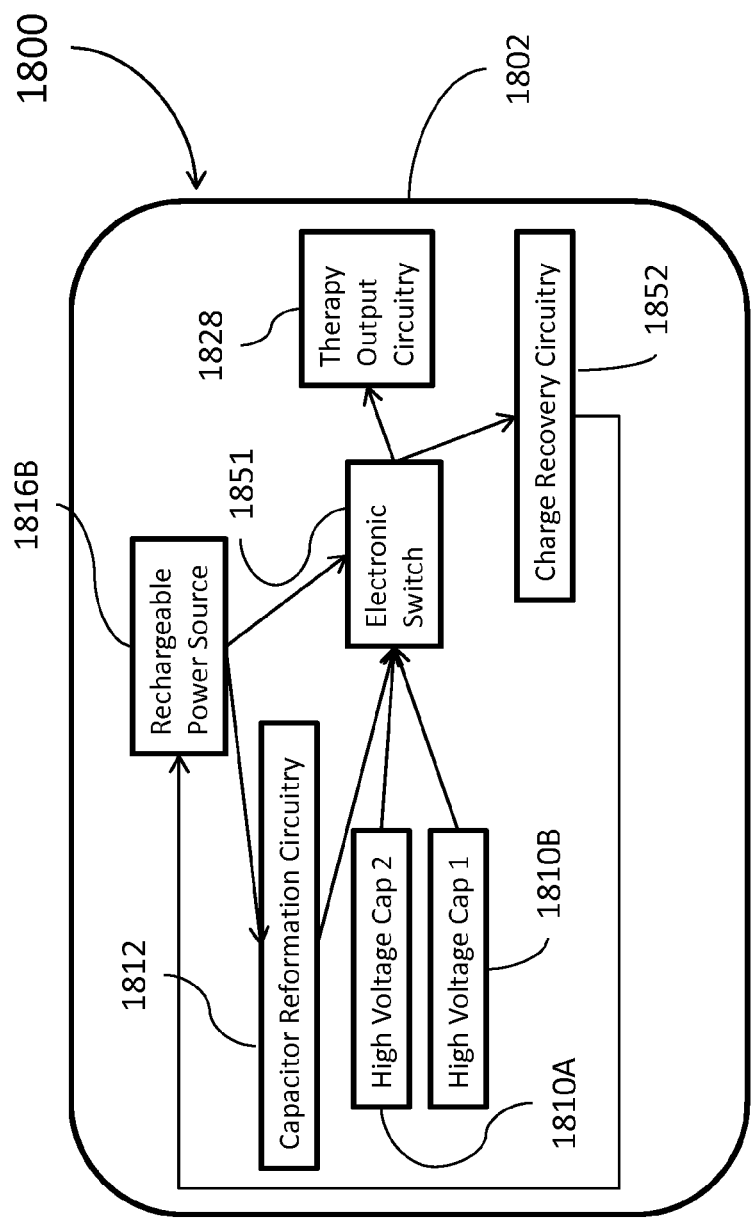

FIG. 18 shows an implantable device 1800, which is similar to device 1500 except that the power source is not included and the rechargeable power source 1816B provides the power to the device 1800. The single rechargeable battery 1816B allows for charge recovery in the battery, and operates to reduce unnecessary loss of energy due to cap reform. With the rechargeable power source 1816B, there is no need for dump resistors as shown in FIG. 14. When an output therapy signal is needed, the rechargeable power source 1816B charges the capacitors 1810A, 1810B.

Figure 19:
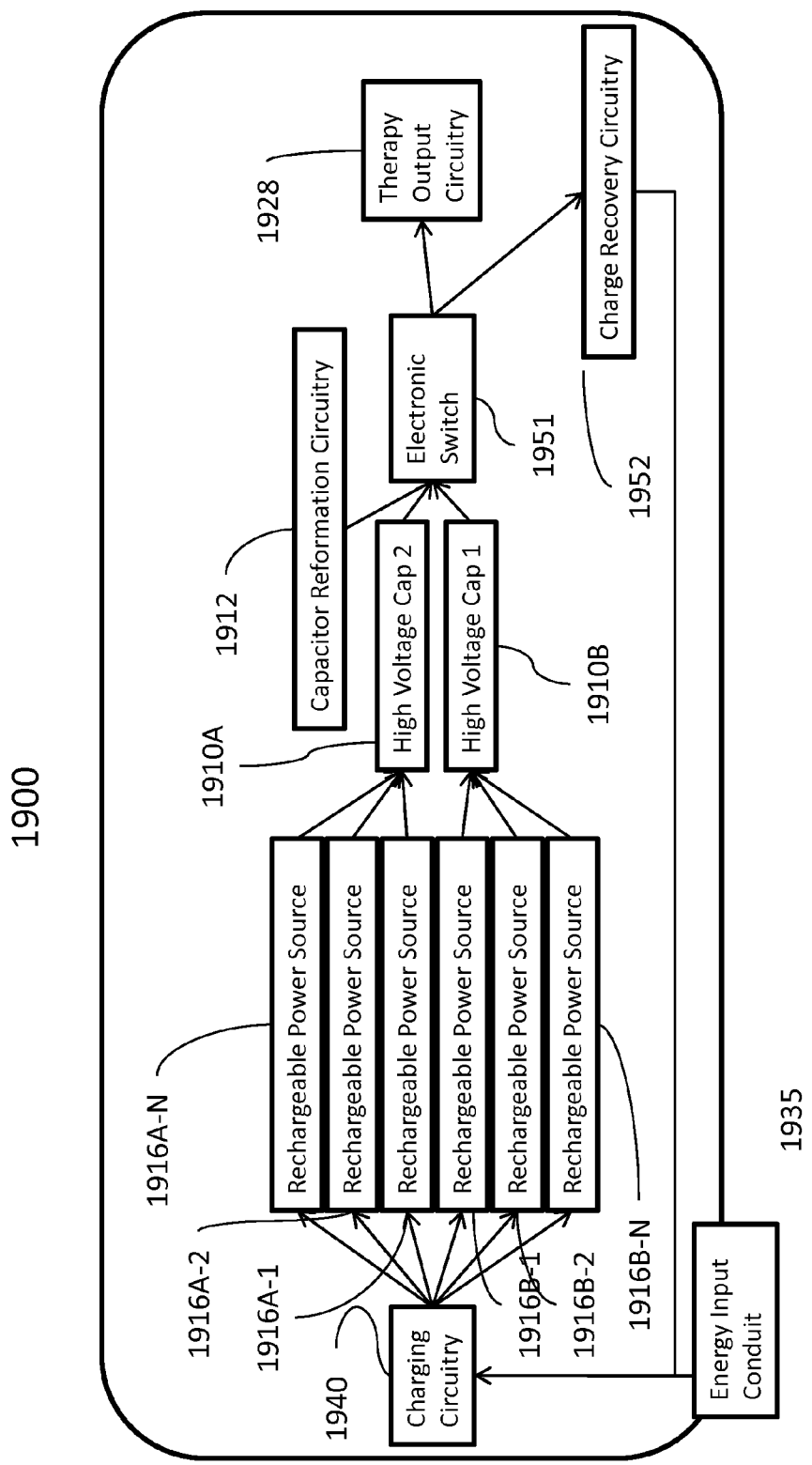

FIG. 19 shows an implantable device 1900, which is similar to the medical device 1800 described above with additional rechargeable batteries 1816A-1, 1816A-2, . . . 1816A-N and 1816B-1, 1816B-2, . . . 1816B-N, recharging circuitry 1940 and in electrical energy input 1935. The multiple rechargeable power sources can be used to recharge the capacitors to decrease the time to output of a therapy signal. Here as shown in FIG. 19, a plurality of first power sources 1916A is connected to a first capacitor 1910A. A plurality of second power sources 1916B is connected to a second capacitor 1910B. Charging circuitry 1940 is connected between charge recovery circuitry 1952 and the rechargeable power sources 1916A, 1916B to recover and reuse electrical energy not output as a therapy signal. A power input conduit 1935, e.g., a receptacle, is connected to the charging circuitry and allows an external energy source to input electrical energy into device 1900 to be stored in the rechargeable power sources 1916A, 1916B. The charging circuitry 1940 can control the flow of electrical energy into the power sources 1916A, 1916B to reduce the risk of thermal runaway. As the multiple rechargeable power sources can receive a greater charge volume over a period of time than a single rechargeable power source, the device 1900 can be recharged in a faster manner than a single rechargeable battery embodiment.

The above embodiments describe multiple housing embodiments (see FIGS. 9-11 and 14-19 and related description), which allow for the physical segregation of various device components and processes. The patient monitoring can be separate from the power sources for producing a therapy signal. The housings can be in electrical communication through, e.g., leads or other implantable wires. These multiple housing embodiments (see FIGS. 9-11 and 14-19 and related description) can transfer power between the power sources in the receptive housings as well as share data.

The switch 1451-1951 operates to control the flow of electrical signals in the various devices 1400-1900, respectively. The switch 1451-1951 can act as an output signal termination device to end the ability of the device 1400-1900 to output a therapy signal. The switch can include a fuse, and antifuse, circuitry that prevents an output signal from being supplied to output ports (e.g., ports connected to the leads or the housing), or instructions being executed by processing circuitry. In another example, the switch stops the ability to charge the capacitors with sufficient electrical charge to create a therapy signal. The switch can be triggered after the expiration of a time period or reaching a time period. The switch can also be triggered by the number of reformation cycles by the reformation circuitry. The switch can also be triggered by the number of therapy signals output by the device. The alarm signal can be output to the patient, the medical provider, or external computer device once the switch is triggered to end the therapy output ability of the device. The devices 1400-1900 can include the communication structures described above with regard to FIG. 9. The communication structures can be wired or wireless and can communicate the alarm signal to devices outside the implanted devices 1400-1900.

FIGS. 20-22 show various embodiments of power sources 2000-2200 for use with implantable medical devices as described herein, according to various embodiments. FIG. 20 shows a power source 2000 with a single battery 2016 in a single enclosure 2013. Contacts 2019 are provided through the enclosure 2013 to allow the flow of electrical energy to or from the battery 2016. In an example, the battery 2016 is a rechargeable battery. The enclosure 2013 is designed to fit with an implantable housing of an appropriate size along with the associated electronics. FIG. 21 shows two independent batteries 2116A, 2116B each in electrical communication with respective contacts 2119A, 2119B. The example shown in FIG. 21 shows that multiple, distinct and individual batteries can be used in place of a single battery, i.e., battery 2016 of FIG. 20, and yet have essentially the same volume or footprint in the medical device (not shown in FIGS. 20-22). In an example, at least one of batteries 2116A, 2116B are rechargeable. FIG. 22 shows power source 2000 that includes an enclosure 2213 enclosing a plurality of batteries 2216A and 2216B, which are connected to contacts 2219A, 2219B that extend outside the enclosure 2213 to provide electrical communication with external circuitry (not shown in FIG. 22). Batteries 2216A, 2216B are individually packaged. At least one of the batteries 2216A, 2216B can be a rechargeable battery. The example shown in FIG. 22 shows that multiple, distinct and individual batteries can be used in place of a single battery, i.e., battery 2016 of FIG. 20, and yet have essentially the same volume or footprint in the medical device (not shown in FIGS. 20-22).

FIGS. 23-24 show various embodiments of implantable medical devices 2300-2400, according to various embodiments. Both medical devices 2300 and 2400 include a housing 2302 and 2402, respectively. Housing 2302 and 2402 are biologically compatible with the patient's body and so that the housings can be implanted within the body of the patient. The housings 2302 and 2402 can each house the various components as described herein as long as the description relating to these components does not result in a conflict with the specific disclosure relating to the present embodiments of FIGS. 23 and 24. Housing 2302 includes a single battery 2316 that operates as the sole power source for the device 2300. Housing 2302 further includes input/output contacts 2319 to provide electrical communication between external circuitry (not shown in FIG. 23), e.g., recharging circuitry and the battery 2316 or regulation circuitry 2314. Circuitry 2314 is within the housing 2303 and acts to regulate the operation of battery 2316. In aspects, the circuitry 2314 can control the flow of electrical energy within the device 2302. In an example, the battery 2316 is a rechargeable battery. Circuitry 2314 regulates the recharging and charge of the battery 2316. Circuitry 2314 can reduce or stop the flow of electrical energy to or from the batter 2316 if the energy flow exceeds a threshold, e.g., rate or quantity. In an example, circuitry 2314 determines if the intake rate of electrical charge exceeds a safe threshold limit of the battery 2316. The circuitry 2314 can also include a temperature sensor to sense the temperature of the battery 2316. If battery temperature exceeds a threshold, then the circuitry 2314 can stop the flow of electrical energy to the battery. The circuitry 2314 can determine the rate of temperature change or the actual battery temperature. If one of these exceeds its respective threshold, then the circuitry can stop the flow of electrical energy to help prevent battery or device failure. Device 2300 can reduce the chance of incompatibility of the charger (external circuitry) being incompatible the battery 2316. If the thresholds of a rechargeable battery are allowed to be exceeded, design to the battery, then there is an increased risk of catastrophic results, e.g., thermal runaway.

FIG. 24 shows a device 2400 that includes a housing 2302 that encases a battery unit 2416, which itself encases a plurality of batteries 2416A and 2416B with regulation circuitry 2414. In an example, the left battery 2416A is a primary battery and is not rechargeable. In an example, the left battery 2416A is a primary battery and is rechargeable. The right battery 2316B is a rechargeable battery. Contacts 2419A and 2419B provide electrical pathways for the respective battery 2416A and 2416B. The regulation circuitry 2414 can operate similar to circuitry 2314 described with respect to FIG. 23. The batteries 2416A and 2416B can be packaged separately from each other. Battery 2416A is larger than secondary battery 2416B and has a larger energy storage capacity than the secondary battery 2416B. The regulation circuitry 2414 can be packaged with the secondary battery 2416B. In an example, regulation circuitry 2414 is adapted to regulate only the secondary battery. In an example, regulation circuitry 2414 is adapted to regulate operation, e.g., recharging or energy flow to both the primary battery 2416A and the secondary battery 2416B.

While described above as an implantable device, it will be recognized that various components can be in separate housings for implantation. It will be further recognized that some components can be positioned outside the body with other components positioned within the body. For example, the body orientation unit can be outside the body and can communicate wirelessly to the implant to send orientation data or a therapy allowed or therapy disallowed flag or signal.

The circuitry described herein as separate circuitry can variously be combined in some further examples. For example, the circuitries 812, 814A, 814A-814D can be combined in to a pulse generator to produce a therapy signal from the energy sources and/or capacitors. In an example, a pulse generator can include electronic circuitry, a battery, capacitors to store the electrical charge, and a electronic computing device to evaluate the heart rate, store it in memory, and determine when to deliver therapy and when to stand by and process sensed data.

The term "machine-readable medium" should be taken to include a single medium or multiple media (e.g., a centralized or distributed database, and/or associated caches and servers) that store the one or more sets of instructions or data on which instructions operate. The term "machine-readable medium" shall also be taken to include any medium that is capable of storing, encoding, or carrying a set of instructions for execution by the machine and that causes the machine to perform any of the one or more methodologies illustrated herein. The term "machine-readable medium" shall accordingly be taken to include, but not be limited to, solid-state memories, optical and magnetic media, and carrier wave signals. The machine-readable medium is used to store instructions for execution by the devices described herein. These instructions can include control instructions for processing devices and data interpretation instructions.

The prophylactic device will have the ability to monitor and store events as they occur. This feature will allow the physicians to recall the episodes and study them to further diagnose the root cause of the patient's arrhythmia in an attempt to better treat the patient with a combination of device and drug therapy.

In typical implant sessions, the administration of DFT is a means for testing the normal operation of the device before it is fully implanted. Given that the DFT is not necessary for the prophylactic device in this invention, the system contains a device test feature that is attached to the output lines of the device. This device has the ability to introduce impedance to the input lines of the device and receive shock output from the device. Using this mechanism, the ICD can be tested before fully inserted in the patient. This ensures any inoperative device is detected and isolated before implant.

The prophylactic device is limited in life to a predetermined duration of time set at factory, for example 5 years. During this period the device will have continuous monitoring and protection mechanisms operational. Once an event is detected, the device will have enough energy to proceed with a sequence of defibrillation shocks predetermined by the physician. Following the successful rescue of the patient, the device will have enough energy to rescue the patient for a few other episodes, for example 2 episodes, which could be experienced in a period no more than a predetermined period of time, for example one month. The patient has the responsibility to seek medical attention following the first rescue operation. Should the predetermined period of time expire, the patient is no longer in safe protection mode and could lose benefit of a fully operational device.

Signal analysis is dependent on signal quality. If the quality of the collected signal is low, then the algorithm is subject to mistakes. There are several factors that contribute to the quality of the signal. There are many inventions and technologies that try to address this deficiency in signal quality and deal with them on the therapy selection decision. Factors can include performance of leads, performance of electrodes, interface between the electrode and patient tissue (which can create a capacitive effect and/or resistive effect on the signal), patient tissue, and patient hydration, among others. These factors can all contribute to overall performance of the device. If the signal quality is not good, then it is possible for the device to output a defibrillation therapy when the patient does not need it. This phenomenon is called "inappropriate shock" by the industry. A defibrillation shock is a powerful intervention (electrical signal applied to the heart tissue) that can be quite painful. It is not an issue if it is administered at the right time as when the patient is in real need of a defibrillation therapy they are in an unconscious state and have lost the ability to feel pain that is the result of applying an electrical signal (over 30 joules) to heart. But if the device outputs a therapy signal when the patient is awake, and does not need defibrillation therapy, the pain to the patient would be intense and possibly unbearable.

Embodiments of the present invention use patient's body position to decide if a shock should be administered. Using these embodiments, the present device will use signal processing algorithms to decide if the patient is in need of a defibrillation therapy. Once the decision is made to administer the defibrillation therapy, the device uses information available from various sensors to determine the position of the body, levels of movement, etc. to decide if the patient is in fact incapacitated or not. The therapy will only be delivered if the electrical signal from the heart and the body sensors are in correlation with one another. This approach will reduce the number of inappropriate shocks that the patient will experience.

When the device decides that the patient needs a shock therapy, it starts the process by charging the high voltage capacitors to deliver defibrillation shock signal. The nature of this process is such that the charging of the capacitor results in a distinct sound that is detected by most patients. In cases where an inappropriate shock is about to be delivered, patients are told to brace themselves for the upcoming shock. The period of time between the start of capacitor charge, and delivery of the shock is an unpleasant and frustrating time that the patients know something bad is about to happen to them. In such circumstances conventional ICDs do not provide any means of termination of the process by a patient as there is no physician available nearby.

Embodiments of the present invention uses the information from body position sensor(s) to allow the patient to intervene if an inappropriate shock is about to be delivered. The device will have an alarming mechanism that generates a sound inside the device. This sound in conjunction with the capacitor charging sound is meant as an advance warning to the patients. Should a patient detect such an alarm, they are conscious and not in need of a defibrillation shock. At this point they can use their body position to let the device know of incorrectness of its decision. As the device will not deliver the shock unless the body position is consistent with the concluded physiological state, the patient only needs to stand up or sit up vertically to let the device know that the patient is not in need of a defibrillation shock. This mechanism and process will allow for elimination of a large portion of inappropriate shocks that can be delivered by a cardiac implant device.

Current ICDs have similar electronic design in that they all have electronics for processing, an energy source such as a primary battery, and a set of high-voltage capacitors that are used as means of collecting charge from the battery and accumulating them in order to deliver high voltage defibrillation shock needed to recover the heart from arrhythmic conditions. These capacitors are made up of various technologies, such as electrolytic, among others. Such capacitors have a need to be used in order to maintain the longevity of their chemistry. In order to address this inherent need of electrolytic capacitors, ICDs use a capacitor reformation process to maintain functional integrity of these components.

During a capacitor reformation process, the capacitors are charged up to max, and then discharged completely. This process occurs on a monthly basis, or any other periodicity seen fit by the manufacturer. Once the capacitors are charged up, the only way to discharge them is via using a dump resistor to release the charge and dissipate it. This dissipation process is similar to if the charge was delivered to the patient in a defibrillation shock. Although this is needed to maintain the integrity of the capacitors, it is a waste of energy and unnecessary drain to the battery. Should the system not lose this energy, they would last much longer than they do currently.

Embodiments of the present invention allows for use of a rechargeable battery that can be used in conjunction with the rest of the device to better conserve energy and increase life of the device. In an embodiment of the present disclosure, a small rechargeable battery can be incorporated in the device that can hold one full charge for both capacitors. The device's electronic circuitry is used to ensure that the rechargeable battery is full at all time. Should the energy level in the rechargeable battery drop below the level needed to fully charge both capacitors, additional energy is pulled from the primary battery and added to the rechargeable battery. During the capacitor reformation process, charge is pulled from the rechargeable battery in to fill the capacitors. Once the reformation process is completed, charge is removed from the capacitors and restored in the rechargeable battery. Using this approach the charge is not lost and is maintained in a reusable reservoir. This approach of preventing unnecessary energy loss contributes to extended life for the device by allowing the primary battery to last longer.

In another embodiment, the device has only a rechargeable battery to support all of its operational needs. In such system, capacitor formation is done using energy that is pulled from the rechargeable battery and then placed back in to the battery for future use.

ICDs are designed to provide life saving support by administering a defibrillation shock when the patient has been deemed in need of it. The medical community believes that the earlier this defibrillation shock is delivered from the onset of the event, the higher the chance of recovery for the patient. Therefore many technologies have been developed to allow the algorithms to detect the event faster, and the device to deliver the shock quicker. Once an event is detected that needs defibrillation therapy, the device starts the process by charging the capacitors. This process takes time in the order of 6-10 seconds. This time is due to limitation of the energy source and how much and how fast it can provide the energy to fill up the capacitors prior to discharge in the form of a defibrillation shock. Manufacturers have developed various technologies that allow faster detection, faster commitment, faster charging, etc. in order to shave off fractions of a second from this time.

An embodiment of current disclosure allows reduction of charge time by using multiple sources of energy. In an embodiment, the device has a primary battery and a secondary rechargeable battery. The rechargeable is used primarily for capacitor reformation process. In this design, the rechargeable battery is always full of energy, enough to charge up both capacitors. When the device decides to deliver a defibrillation shock and initiates the capacitor charging process, the electronic circuitry in the device will use energy from the primary battery to charge one of the capacitors, and the energy from the rechargeable battery to charge the second capacitor. With this design, the device will cut the charge time for the capacitors, for example, by 25% or by half, or less than 5 seconds or less than 3 seconds. The device will be charged for output and ready to deliver a life saving defibrillation shock signal less time than a current ICD.

Current ICDs implantation processes require multiple stages of evaluation prior to implantation of the device. As part of the process, patient is subjected to defibrillation threshold (DFT) testing. This is a procedure that evaluates the level of energy required to successfully recover the patient from an episode of VF, or SCD. In this phase, patient is induced in to VF and the device is used to administer various defibrillation shocks at different energy level. This process was made necessary over 20 years ago when the first implantable defibrillators were developed. The ICDs did not have enough energy to successfully defibrillate a patient to normal rhythm. So physician tested device in patients, before final implantation, to ensure that it can successfully recover them. Additionally, since the defibrillation shock is directly tied to the energy consumption and longevity of the device, it was and still is essential to make sure the least amount of energy is used to recover the patient in order to maximize the life of the device, while providing safe solution for the patient.

Since then higher energy devices have been developed that at 40 J can successfully recover the patient. Additionally, studies have been conducted that show setting lower level defibrillation threshold is not necessary as the high energy defibrillation shock is as effective as it could be with less number of shocks. Furthermore, in application of prophylactic devices that are implanted in patients without prior episode of fibrillation, a group of physicians and scientists believe that the administration of the DFT test may start the heart failure decompensation process unnecessarily.

The current invention allows for a defibrillation device that is set for one level of energy set at maximum, where this maximum may be 50 J, or may be 40 J, or other appropriate level that can successfully recover the patient from an episode of VF or SCD. Furthermore the current invention claims a process where the patient, who is identified at risk of a VF or SCA, or SCD, or VT, and in need of an ICD, can be implanted an ICD without conduct of a DFT test, or any other form of therapy evaluation that would require inducing a life critical event in the patient's heart.

The present prophylactic device, in various embodiments, can reduce device costs by not implanting a full-featured device. Moreover, unnecessary treatments may be avoided and the number of qualified health care surgeons is increased by utilizing the prophylactic device. The qualified health care surgeons can implant a correct prophylactic device for each patient, e.g., the patient not requiring a current "full feature" cardiac implant can use the present prophylactic device. As a result, the present prophylactic device can increase reliability (e.g., reduced design errors, electrical failures, etc.) and provide efficient operation (e.g., battery life).

In many of the above embodiments, the implantable device is shown with a charging receptacle or port and a lead-engaging port. The receptacle and the lead-engaging port are positioned in the housing, e.g., a can. The housing can have a header in which both the receptacle and the lead-engaging port are positioned.

The prophylactic device(s) described herein is implanted in any patient that is at risk of sudden cardiac death (SCD). The prophylactic device(s) described herein can be of a limited life device, e.g., about 5 years, with the capability to protect a patient from episodes of VF or SCD where there is no other way to recover other than a defibrillation shock, which is automatically produced by the prophylactic device. This device does not need any programming during its implantation or during its lifetime as it merely protects against cardiac failure events (e.g., SCD) and does not have programmable parameters. The device can feature a primary battery large enough to operate its internal circuitry (e.g., electronics) to well beyond the predetermined life of the device. This allows the circuitry to survive the end of life status of the device. The device can have circuitry to ensure that the device is not kept in operation beyond its predetermined life. Using such circuitry, the device outputs for therapy signals (e.g., defibrillation) will be permanently disabled, upon the predetermined end of life, and will not allow the device to output any therapeutic energy after the end of life. This is to ensure the device is not used beyond its reliable life, which can place a patient at risk. One reason for the present device to is based on the facts that decisions relating to applying therapy to a patient are medical decisions, typically decided by physicians with input from a patient and other medical care providers. However, decisions as to reliably of components of a medical device are an engineering decisions. It is unfair to put this decision in the hands of physicians as they are highly qualified with regard to medical decisions; they are typically not qualified to make decisions with regard to engineering related decisions for medical devices. For example, physicians would have to make trade-offs among physiological and medical outcomes, along with electronic and engineering outcomes.

The devices, as described herein, can have primary battery that can support patient for one therapeutic intervention and stay in operation for a minimum time after the intervention, e.g., up to one month, which will give a patient enough time to seek medical attention. The patients are properly informed of the limitations of the product at the time of selection and implantation. The patients are further informed of the need for them to keep in touch with their care provider for long term management of the device and the patient's health.

Examples of the devices, as described herein, can have only one energy setting, 40 J or 50 J, depending on the specific device. Studies have shown that performing Defibrillation Threshold Testing ("DFT") testing to evaluate defibrillation threshold and programming the device to lower energy has no medical benefit with regard to SCD. In devices that have limited battery power, this is used to set the lowest level of energy that is safe for the patient, in order to maximize the device life. The devices described herein will have sufficient energy to provide the safest therapy to the patient without the need for further testing. Medical studies have suggested that the performance of the DFT testing could be the genesis of the heart failure progression and subject the patient to an unnecessary event that could actually harm the patient's heart. In cases where the testing is necessary to evaluate the effectiveness of the device, this could be important. But in the case of a preferred embodiment of the present device, the test is not necessary as the physician has no choice in programming and has to live with the device in its pre-programmed state.

The other use of the DFT testing is to ensure that the device is performing properly before it is implanted in the patient. In the present system, the device will have a test tool that is connected to the device at the point of implant, to test all its functionality before the device is committed to the patient. This tool connects to the output ports of the device, where leads typically get connected, and subjects the device to simulated heart rate, tissue impedance and load, allowing the device to exhibit its ability to output a shock at the right time, and at the right level of energy.

Various embodiments of the present device will have full monitoring and data storage capability to collect episodes of cardiac arrhythmia and store them for review by the patient's physician. The information from physiological sensors is collected to make therapy decision by the device. Additionally such information is stored in the device to allow the physician to review and assess the health of the patient and operation of their heart, at any subsequent visits. This information can also be downloaded from the device through communication connections, e.g., wireless or mechanically contacts, to a computing system for review by other programs and the medical care provider.

The devices, as described herein, can have additional body position sensors and algorithms that will use the position of the body, in addition to trends in the body activity to corroborate the assessment of physiological sensors. In particular, once the device's physiological sensors have determined that the patient is in SCD, the device evaluates information from body position sensors and activity sensors, in addition to trends from other physiological sensors available in the device, to validate the conclusions of the device, before allowing the device to output any defibrillation shock to the patient. This level of rigor is put in place to ensure that the patients are receiving defibrillation shocks when they in fact need them, reducing the probability of outputting inappropriate shocks. For example, if the cardiac ECG analysis determines that the patient is experiencing an episode of SCD, the device will review to ensure that the respiration signal is also down showing low levels of respiratory activity, if any, and then look to see if the physical activity of the patient has exhibited any change from before the onset of the event, and the body position of the patient is also consistent with a patient in cardiac arrest. If all of these factors persist, then the device is authorized to output a shock. Once the device has determined that the patient is in need of intervention, it starts pumping energy in the high-voltage capacitors. This process will take seconds until the capacitors are charged with adequate electrical energy for the defibrillation shock signal. In an embodiment, the device outputs an alert (or alarm) signal to inform the patient of an upcoming defibrillation shock while preparing the defibrillation shock signal. This alert could be in the form of a sound generated by the device inside the body, or vibration of the housing (e.g., can) to raise awareness in the patient. If the patient is in fact not incapacitated, they can raise their torso (e.g., into the vertical orientation) and cause the body position detection sensor to terminate the defibrillation attempt. This approach puts some control in the hands of patients who may be shocked inappropriately.

The prophylactic device(s), as described herein, can have the ability to communicate with the outside through the means of inductive telemetry signal or wireless RF communication. These methods of communications are used by external physician programmers to connect with the device and collect physiological information in addition to device performance from the device. In situations where the patient is under the care of a remote monitoring system, such as Latitude™ system offered by Boston Scientific, or C are Link® offered by Medtronic, the device can communicate alerts related to shock attempt and battery life to the physician through these intermediary subsystems.

The device(s), as described herein, can be used in patients without any prior episode of SCD or VF, but are determined to be at risk, it is meant as a simple system that protects the patient from death, in case an episode presents itself. Once an episode is experienced, the patient is not longer at risk, but is then medically indicated in need for long term protection. The present prophylactic device is designed to protect the patient up to and including the first episode. Once the first episode is experienced they are to reach out to their physician and determine a longer term solution. Once the device has rescued the patient from their first episode, it can begin outputting an alert signal through the remote monitoring system, to the physician and medical institution, urging them to attend to the patient as the device will expire soon. Additionally, the internal alerting system of the device will initiate an ongoing alert to the patient, indicating a need to seek medical attention. As the device gets closer to expiration date, as determined by the predetermined expiration time of the device, the level of alerting becomes more intense, further urging the patient to seek medical attention. The progression of the alerting is described in more detail herein. As similar progression in intensity of alert signaling the patient if the patient does not seek medical care when a first episode has occurred.

Once the prophylactic device has successfully rescued a patient from a cardiac episode, it can use its internal RF communication mechanism to report an alarm to the bedside monitoring system, e.g., external device 910 of FIG. 9. This alarm is then transferred to the hospital, monitoring company, physician or any combination thereof, the need for attention as the device may expire soon. The remote monitoring service (devices and methods) will reduce the need for attention from the patient as the automatic system will perform the necessary review and reporting.

In the event of a battery depletion and need for recharging, the implanted device can wirelessly communicate with a patient monitoring system the status of the battery and the need for recharging. The remote monitoring device can communicate the situation to the physician or clinic through electronic communication, e.g., internet or wireless communication. This method will alarm the physician of the issue and will allow the physician to intervene ensuring device recharge and continued operation. In an example, if the patient is mobile, the device alerts the patient through internal sounds or alerting mechanisms. When the patient is in the remote monitoring zone, the device communicates the issue to the remote monitor (e.g., device 910 of FIG. 9), informing the monitoring company or the physician of the need for attention.

The present devices described herein can also include rechargeable power sources. The rechargeable device(s), as described herein, can include all the capabilities in the prophylactic device(s), in addition to having a rechargeable battery and mechanism for recharging over time. This device is designed to last a longer time that the prophylactic device, for example, 10 years, 12 years, or more, without the need for battery replacement. The device can have an expiration date dictated by reliable life of the circuitry and other components inside or part of the device. The device can have defibrillation capability and post shock pacing to assist heart in recovery from a shock until the normal sinus rhythm picks up. The device can have additional features for diagnosis and monitoring of the patient, for example, as described herein.

Typical rechargeable devices have small batteries and recharging mechanism that uses inductive method of charge transfer through the skin. Due to limitations of charge transfer using this method, medical devices need to be charged almost daily. Such approach may be acceptable for applications that need occasional use, but are not useful for applications that require continuous use, which includes potentially life-saving implantable medical device as described herein. On the other hand, if a medical device has a larger battery in it, then the charging mechanism would require hours and perhaps days of charging to restore the energy in the battery to its full capacity. Obviously multiple hour-long charging is not acceptable, nor is it practical. Devices, systems and methods described herein can use a mechanism for directly connecting, e.g., a mechanical connections to transfer electrical energy and data, the device inside the patient to a charge transfer device that is positioned outside the body. This method of direct connection will allow charge transfer in orders of magnitude faster than current, induction mechanisms allow. The ability to recharge the battery at a much faster rate allows design of devices that have denser and larger rechargeable batteries that offer patients longer use between charges. This ability of longer use on a single charge makes the device more practical and acceptable to the patients and their physicians.

Additionally current limitation of power and energy in the conventional devices has limited their capabilities in terms of additional features and components. Once devices have unlimited energy available to them, they can do more and more and better justify the cost of implantation. For example, a device with unlimited energy can have a combined capability for cardiac therapy and neurostimulation, all in one box.

An implanted medical device performs two major functions, monitoring and therapy. The rechargeable battery of the presently described devices can be designed with power management circuitry to ensure that there is enough charge in the device to carry the monitoring and data collection portion of the device for the life of the product. The additional energy in the device can be directed to therapy output. As the energy in the battery falls below the available energy limit, without compromise to monitoring, the device will stop attempting any therapy output.

This process of energy preservation not only ensures the device will maintain monitoring information for physician to review for future diagnosis and therapy decisions, but also will ensure the proper longevity of the rechargeable battery. Some rechargeable battery chemistries are susceptible to zero charge, such that if they reach total depletion levels, they lose their ability to get back to full charge, therefore reducing life and longevity. The power management circuitry in this device will ensure that the device will never reach the zero level charge by keeping the device from outputting charge if charge is not available, and using its alerting (e.g., alarm signal) capability to inform the patient at various stages of battery life to seek medical and technical attention.

Availability of rechargeable battery inside this device can allow the device to take advantage of another invention provided in this application around capacitor reformation. All implantable defibrillators on the market currently use primary, non-rechargeable batteries. Such devices have internal, high-voltage capacitors that are used as temporary charge accumulation mechanisms that pull energy from the low voltage battery, to create high voltage output that is needed to defibrillate stressed heart muscles. These capacitors use various electrolytic chemistries that need continuous revitalization to keep their chemical integrity. To keep the capacitors at their rated charge accumulation level, they have to be fully charged periodically on a pre-specified schedule that is based on weeks and/or a month or two. Since patient's need for therapy is event based and not time based, the device has to ensure the capacitors are maintained by periodically charging them to full capacity, and then discharge them. This process is known as capacitor reformation. The presently described devices can use capacitor reformation, e.g., once a month, to fully charge the capacitors and then discharge them through a dump resistor that pulls the energy from the caps and destroys it.

Embodiments of the present description can include built in recuperating circuitry that allows the charge used in capacitor reformation to get restored in the battery. This process of restoration of energy is important in that it maintains energy in the battery to be used for actual therapeutic purpose and not used only for device maintenance. This energy preservation mechanism adds significant amount to the life of the device, especially in the recapture of electrical energy used in periodic capacitor reformation, e.g., once a month.

Various aspects of the present disclosure are summarized below.

An example of the present implantable medical device, according to the present disclosure, can include one or more cardiac sensors to detect a cardiac episode and outputting cardiac data, a body orientation unit to determine an orientation of a body and to output orientation data and; therapy circuitry to apply cardiac therapy using the cardiac data and the orientation data. An example can include any above example and the body orientation unit including an accelerometer. An example can include any above example and the accelerometer including at least one of a capacitive device, a MEMS device, a plurality of two-axis devices, a single three-axis device, and a six-axis device, which are to output a signal indicative of an orientation of a patient. An example can include any above example and the body orientation unit including an inclinometer. An example can include any above example and the inclinometer including at least one of a capacitive device and a MEMS device, which can output a signal indicative of an orientation of a patient. An example can include any above example and the body orientation unit including a gyrometer. An example can include any above example and the gyrometer including at least one of a MEMS device and a three-axis device, which can output a signal indicative of an orientation of a patient. An example can include any above example and the therapy circuitry is to deliver only a defibrillation signal. An example can include any above example and the therapy circuitry is free from pacing determinations and is free from delivering pacing signals.

An example of the present device can include any above example and an implantable cardiac device with: a housing to be implantable and essentially biologically insert in a body of a person; cardiac detection circuitry to detect a cardiac episode; cardiac therapy circuitry to deliver a cardiac therapy signal; a body orientation unit to determine an orientation of a body, wherein the body orientation unit is to control delivery of the cardiac therapy signal to a heart when the body orientation unit determines that the orientation is essentially vertical. An example can include any above example and the body orientation unit is to allow delivery of the therapy signal to a heart with the orientation being essentially horizontal. An example can include any above example and wherein the body orientation unit includes an accelerometer. An example can include any above example and wherein the accelerometer includes a MEMS device that is senses 3-axis orientation of a person. An example can include any above example and wherein the body orientation unit includes an inclinometer. An example can include any above example and wherein the inclinometer includes a MEMS device that is senses 3-axis orientation of a person. An example can include any above example and wherein the body orientation unit includes a gyrometer. An example can include any above example and wherein the gyrometer includes a MEMS device that is senses 3-axis orientation of a person. An example can include any above example and wherein the cardiac therapy circuitry includes a processor to receive orientation data from the body orientation unit and to control delivery of a defibrillation signal to the heart. An example can include any above example and wherein the cardiac therapy circuitry includes one or more capacitors to supply energy for a defibrillation signal and capacity reformation circuitry. An example can include any above example and wherein the cardiac detection circuitry includes sensors to connect to leads, the sensors to analyze a heart signal and indicate an abnormal heart rhythm. An example can include any above example and wherein the housing includes a data storage system in the housing to store device performance data and patient related data.

An example can include any above example and an implantable cardioverter defibrillator for prevention of sudden cardiac death comprising: one or more housings; one or more sources of energy; one of more cardiac sensors to detect a cardiac episode; one or more sensors to detect of body orientation; electronic circuitry to manage energy sources and energy stored therein; electronic circuitry to perform capacitor reformation; electronic circuitry to arbitrate and decide to use one or more of energy sources to power various portions of the system; electronic circuitry to deliver energy for cardiac defibrillation therapy only; electronic circuitry to detect sudden cardiac death or presence of cardiac ventricular fibrillation episode; and electronic circuitry to alert a patient. An example can include any above example and including one or more leads that connect the electronics from the housing to the heart tissue to detect cardiac signal and to deliver of defibrillation energy to the heart tissue. An example can include any above example and the housing includes one of more headers to connect to components outside the housing. An example can include any above example and wherein the housing includes at least one high voltage capacitor to store and deliver high voltage defibrillation energy to the heart. An example can include any above example and wherein the energy source is a primary, non-rechargeable battery. An example can include any above example and wherein the energy source is a rechargeable battery. An example can include any above example and wherein the electronic circuitry to manage the energy stored in the energy sources comprises a recharging circuitry in the housing, and wherein the housing includes a recharging port to receive electrical energy from outside the housing. An example can include any above example and wherein the recharging port includes a connector in the housing through which an external charge generation system can directly connect to the implantable device. An example can include any above example and wherein the recharging circuitry includes a magnetic coil that receives electromagnetic charge from an external electromagnetic charge generating system. An example can include any above example and wherein the energy source includes a primary battery and a rechargeable battery. An example can include any above example and wherein the energy sources are packaged separately for leak prevention and safety, inside the housing. An example can include any above example and where the housing for rechargeable battery also contains the charge regulation circuitry to manage the recharging process. An example can include any above example and wherein the energy sources are packaged together inside the housing. An example can include any above example and wherein the primary battery is to power the electronics in the housing and the rechargeable battery is used to power the high voltage capacitors and defibrillation therapy. An example can include any above example and wherein the primary battery is large enough to only supply energy to operate the electronics, and the rechargeable is used to continuously deliver therapy energy to patient, and to be recharged from outside the housing. An example can include any above example and wherein the primary battery is large enough to last the entire life of the device, and the rechargeable battery is limited in electrical energy to two full therapy charges to be delivered to the capacitor without recharging the rechargeable battery from outside the housing. An example can include any above example and wherein the electronic circuitry to manage energy sources and energy stored therein can pull energy from the primary battery to power the rechargeable battery as needed. An example can include any above example and wherein the rechargeable battery is to power the electronics in the housing and the primary battery is used to power the high-voltage capacitors and defibrillation therapy. An example can include any above example and wherein the electronic circuitry to deliver energy uses both the rechargeable battery and the primary battery to charge the high energy capacitors to expedite the capacitor charging process. An example can include any above example and wherein the electronic circuitry to manage energy sources and energy stored therein can pull energy from the primary battery to power the rechargeable battery as needed. An example can include any above example and wherein the primary battery is large enough to only supply energy to operate the electronics, and the rechargeable is used to continuously deliver therapy energy to patient, and to be recharged from outside the housing. An example can include any above example and wherein the primary battery is large enough to last the entire life of the device, and the rechargeable battery is limited in electrical energy to two full therapy charges to be delivered to the capacitor without recharging the rechargeable battery from outside the housing. An example can include any above example and wherein the rechargeable battery receives a standby charge from the primary battery, uses the charge for a capacitor reformation process, and uses the energy to charge the capacitors for first future therapy delivery attempt. An example can include any above example and wherein the electronic circuitry to perform capacitor reformation is to pull energy from the rechargeable battery to power a capacitor reformation process, and once done restore the energy in the capacitors to the rechargeable battery to reduce loss of energy. An example can include any above example and wherein the electronic circuitry to deliver energy uses both the rechargeable battery and the primary battery to charge the high energy capacitors to expedite the capacitor charging process. An example can include any above example and wherein the primary battery is to charge the rechargeable battery, after the capacitors are charged up for therapy delivery, allowing fast delivery of defibrillation shocks as the patient needs them. An example can include any above example and wherein the primary battery is to charge the rechargeable battery, after the capacitors are charged up for therapy delivery, allowing fast delivery of defibrillation shocks as the patient needs them. An example can include any above example and wherein the sensor to detect body orientation is an accelerometer, gyrometer, inclinometer or any combination thereof. An example can include any above example and wherein the sensor to detect body orientation is used to detect a horizontal position of the body. An example can include any above example and wherein the sensor to detect body orientation is used to detect a vertical position of the body. An example can include any above example and wherein the energy source is a single, high-voltage battery with Barium Titanate chemistry inside to run the electronic circuitry and the therapy delivery circuitry. An example can include any above example and wherein the housing is free from a high voltage capacitor. An example can include any above example and wherein the therapy delivery electronic circuitry is programmed to allow only a set amount of energy and power to be pulled directly from the battery and delivered to the patients through the lead. An example can include any above example and wherein the energy source includes a first energy storage source for general operation of the system and a second, high-voltage battery including Barium Titanate chemistry capable of storing high energy, enough for one defibrillation shock, and direct delivery of high voltage shock, wherein the second battery receives charge from the first battery for each shock output. An example can include any above example and wherein the energy source includes a first energy source for general operation of the system, and a second, high-voltage, rechargeable battery, including Barium Titanate chemistry, to store high levels of energy and to output high power for defibrillation shocks for in sequence, and a delivery system to recharge the high-voltage battery from outside the housing as needed. An example can include any above example and wherein the position of the body is used to validate conclusions made by the electronic circuitry and algorithms performed by the circuitry of presence of sudden cardiac death, cardiac arrest, or ventricular fibrillation, or any combination thereof. An example can include any above example and wherein the electronic circuitry to deliver defibrillation therapy will only deliver a therapy signal if at the time of delivery the patient's body is in an essentially horizontal position. An example can include any above example and wherein the electronic circuitry to deliver defibrillation therapy will terminate attempt to deliver the planned therapy once the patient's body has returned to an essentially vertical position. An example can include any above example and wherein the electronic circuitry to alert a patient will alert the user of attempts to deliver therapy. An example can include any above example and wherein the electronic circuitry to alert a patient uses at least one of sound vibration, or any other modality to alert the patient of attempt to deliver a defibrillation shock. An example can include any above example and wherein the electronic circuitry to alert a patient alerts the user of the need to seek attention to recharge the device. An example can include any above example and wherein the electronic circuitry to alert a patient uses wireless communication to send a signal from the implantable housing to be received by an external device to alert at least one of the patient and a medical care provider. An example can include any above example and wherein the electronic circuitry to alert is to provide alerts that are more severe as time elapses from when the alert was initiated. An example can include any above example and wherein the electronic circuitry to alert only emits an alert when the patient is vertical and stops when the patient is horizontal to allow for sleep and rest. An example can include any above example and wherein the electronic circuitry to alert continues alerting unless the device has proper level of charge for normal operation. An example can include any above example and wherein the electronic circuitry to alert a patient alerts the user through means of wireless communication with monitoring equipment outside a body of the patient. An example can include any above example and wherein the energy sources include a first high-voltage capacitor, a second high-voltage capacitor, and at least one rechargeable battery, and wherein the energy management circuitry is to control use of the rechargeable battery to perform capacitor formation on first and second capacitors, one at a time, and cycling the charge between the first and second capacitors. An example can include any above example and wherein the energy management circuitry cycles charge through the first and second capacitors before storing the charge back in the rechargeable battery. An example can include any above example and wherein the energy sources include first high-voltage capacitor, a second high-voltage capacitor, and a fast charge/discharge, rechargeable battery, large enough in capacity to at least double the size of energy held on one capacitor, to use for a capacitor reformation process, and wherein the rechargeable battery is used for immediate charging of the first and second capacitors for defibrillation shock delivery when the electronic circuitry to detect sudden cardiac death determines the need for a defibrillation shock signal, thereby reducing a shock readiness time to a few seconds. An example can include any above example and wherein the energy sources include multiple energy sources, and wherein the energy management electronic circuitry is to ensure separation of energy sources and to prevent flow of current from one energy source to the other. An example can include any above example and wherein the housing includes a first housing including the electronic circuitry to diagnose and monitor and an associated energy source, and a second housing including therapy delivery electronic circuitry and an associated energy source, and the first housing and the second housing being in electrical communication with each other. An example can include any above example and wherein the first housing and the second housing are electrically coupled by at least one of a cable, set of wires, leads, or combinations thereof. An example can include any above example and wherein the first housing and the second housing are wirelessly connected to each other. An example can include any above example and wherein the second housing contains a rechargeable battery and an external connector to deliver charge from outside the second housing. An example can include any above example and wherein the electronic circuitry to diagnose and monitor in the first housing is connected to the patient via a lead to sense and assess patient parameters, and the therapy delivery electronic circuitry in the second housing is attached to the patient for therapy delivery, and wherein each can be replaced independent of the other.

Examples as described herein can include communication circuitry to provide communications to, from and within the medical device. An example can include any above example and where the communication circuitry includes a port to receive a probe that pierces through skin of a patient and makes direct connection for electrical communication of at least one of control signals, data exchange, and charge delivery. An example can include any above example and wherein the housing includes a first housing including the electronic circuitries and a second housing including communication circuitry to receive charge and control commands, and the first housing and the second housing being in electrical communication with each other. An example can include any above example and wherein the second housing includes a port to receive a probe that pierces through skin of a patient and makes direct connection for electrical communication of at least one of control signals, data exchange, and charge delivery. An example can include any above example and wherein the probe includes a needle with electrically conductive segments.

An example can include any above example and wherein the charge management circuitry pulls energy from all internal batteries to charge one or more high-voltage capacitors in less than seven seconds to get the defibrillation shock ready for delivery to a patient.

An example can include any above example and wherein the defibrillation therapy circuitry includes a switch to terminate therapy delivery upon receipt of an external signal. An example can include any above example and, wherein the switch can be activated by an external a magnet during a time the notification circuitry is alerting the patient of a sensed cardiac event and imminent delivery of a shock. An example can include any above example and wherein the switch can be activated by an internal system using position of the body of the patient, or level of activity of the body of the patient, or detection of physiological activity of internal organs of the patient, or any combination thereof.

An example of the medical device can have certain therapy signal levels. An example can include any above example and wherein the device has only one or two defibrillation energy levels. An example can include any above example and wherein the device has one defibrillation energy level and the said defibrillation energy level set at 40 J.

An implantable medical device, as described herein can consist essentially of: housing; circuitry to monitor device life using device implant information and an operational life of the device; and circuitry to deliver therapy to a patient. An example can include any above example and wherein the circuitry to deliver therapy is adapted to deliver at least one of cardiac pacing, cardiac defibrillation, electrical stimulation for management of pain, electrical stimulation for prevention of treatment of obesity, electrical stimulation for treatment of neurological disability, ailment or deficiency, electrical stimulation for treatment of physical disability, chemical release for treatment of pain or any other physiological or neurological ailment, or combinations thereof. An example can include any above example and wherein circuitry to monitor device life uses at least one of a fixed period of time since the device was put in to operation, an amount of therapy the circuitry to deliver therapy had delivered to the patient, a shorter period of time programmed into the device by the manufacturer or physician or user, or any combination thereof. An example can include any above example and wherein the circuitry to monitor device life signals the circuitry to deliver therapy to stop operation. An example can include any above example and wherein the circuitry to monitor device life, upon determining that the device life has been exceeded, prevents therapy output. An example can include any above example and wherein the circuitry to monitor device life includes a shut down circuit to halt operation of the device completely. An example can include any above example and wherein the circuitry to monitor device life is to disable electronics permanently. An example can include any above example and wherein the circuitry to monitor device life is to at least one of such as burn a fuse or flip an internal non-reversible switch to cause an irreversible shutdown condition. An example can include any above example and wherein the circuitry to monitor device life is to mechanically disconnect at least one electrode from the electronic circuitry inside the device. An example can include any above example and wherein the circuitry to monitor device life is to electrically disconnect at least one electrode from the electronic circuitry inside the device.

An implantable medical device, as described herein can consist essentially of an implantable housing; two or more rechargeable batteries in the housing; at least one sensor to sense physiological parameters outside the housing; circuitry, in the housing, to manage the batteries and energy stored in therein; and circuitry to receive energy from outside the housing to charge the rechargeable batteries. An example can include any above example and wherein the batteries are connected in parallel to speed up charging and discharging process. An example can include any above example and wherein the circuitry to manage the batteries includes a temperature sensor to sense the internal temperature of at least one of the rechargeable batteries during charging. An example can include any above example and wherein the circuitry to manage the batteries regulates speed of charge transfer using a temperature signal from the temperature sensor associated with the batteries.

An implantable medical device, as described herein, can include or consisting of: an implantable housing; one or more batteries in the housing; at least one sensor to sense physiological parameters outside the housing; circuitry, in the housing, to manage the batteries and energy stored in therein; and circuitry to receive energy from outside the housing to charge the rechargeable batteries. An example can include any above example and wherein the circuitry inside the housing contains charge regulation electronics to manage the charge injection rate in to the rechargeable battery. An example can include any above example and wherein the circuitry for charge regulation is integrated in the electronics outside of the housing to reduce size of the electronics and demand for energy inside the housing. An example can include any above example and wherein the energy from outside the housing is delivered to the inside via inductive methods of energy transfer using coils that are located outside the metal portion of the housing, and connected to the electronics inside the metal portion of the housing through electrical conductive wires. An example can include any above example and wherein the energy from the outside is delivered to the inside via a conduit that mates with the housing mechanical connection or contact. An example can include any above example and wherein the circuitry to manage the batteries contains overcharge protection electronics received for charging the rechargeable batteries.

A medical system, as described herein, can include and of the above examples and can comprise: an implantable, medical device housing with header, wherein the header includes a receiving location to receive a probe from outside a body of a patient; and wherein the receiving location is viewable with medical imaging of inside a body of a patient to facilitate guidance and mating with the probe to the receiving location. An example can include any above example and wherein the receiving location includes an opaque material that makes it visible under the medical imaging. An example can include any above example and wherein the medical imaging includes X-ray imaging. An example can include any above example and can include a probe to deliver at least one of energy and data to the medical device through the receiving location. An example can include any above example and wherein the probe mates with the receiving location by insertion through a patient's skin. An example can include any above example and wherein the probe includes multiple segments to act as cathode connection and anode connection for energy delivery. An example can include any above example and wherein the probe includes multiple segments which can provide digital communication. An example can include any above example and wherein the needle is smooth from top to the tip to ease penetration of the skin. An example can include any above example and wherein the probe includes a smooth outer surface to at least the depth to penetrate a patient's body to reach and engage the receiving location. An example can include any above example and wherein the probe is tapered from a tip to ease penetration into a patient's body. An example can include any above example and wherein the probe includes multiple sets of cathode and anode for electrical energy delivery into the device. An example can include any above example and wherein the device housing includes a probe receptacle comprising multiple segments, with each segment electrically separated from the other to electrically connect to the multiple sets of cathode and anode, and wherein the housing includes a membrane covering the probe receptacle to prevent moisture from leaking into the recess. An example can include any above example and wherein the recess is generally cylindrical. An example can include any above example and wherein the individual segments includes contacts that have mechanical push and makes tight mechanical connection with the probe when inserted in the probe receptacle. An example can include any above example and wherein the contacts are disabled until the probe is completely inserted in the housing and all connections are made with the segments of the probe receptacle. An example can include any above example and wherein the probe receptacle includes a switch adjacent a bottom of the probe receptacle to activate the electrical contacts when the probe is fully inserted. An example can include any above example and wherein the switch holds the electrical contacts in a deactive electrical state until the probe is fully inserted. An example can include any above example and wherein the recess is essentially cylindrical to form a female connector and the probe includes a male connector to mate with the female connector. An example can include any above example and wherein the receptacle housing membrane includes a first layer and a second layer with a fluid intermediate the first and second layers to prevent material or fluid from outside to enter the housing. An example can include any above example and wherein the receptacle housing membrane is to prevent material from inside the housing to exit. An example can include any above example and wherein the fluid inside the two layer membrane includes a quick acting medical glue that activates upon contact with blood or bodily fluid, causing fast closure of the hole in the membrane left behind by extraction of the probe. An example can include any above example and wherein the probe includes an antibiotic coating that further protects the patient from possible infections from a procedure.

An example of an implantable system can include any of the above examples and can comprise a plurality of housings, circuitry inside each housing, means for energy exchange between the electronics in two or more housings, means for information exchange between the two housings, and means for cooperation between the housings. An example can include any above example and wherein the means for energy exchange is a set of electrical conductors connecting one housing to the other. An example can include any above example and wherein the means for information exchange between the housings is a set of electrical conductors connecting one housing to the other. An example can include any above example and wherein the system and all its housings function as a cardiac rhythm management device. An example can include any above example and wherein one housing contains the circuitry and support to sense and assess physiological events. An example can include any above example and wherein the housing also contains the circuitry and support to decide on therapeutic intervention such as pacing, defibrillation, cardiac re-synchronization, or any combination thereof, or other forms of physiological stimulation or modulation. An example can include any above example and wherein another housing contains circuitry and battery for delivering therapy to the body of the patient. An example can include any above example and wherein the battery is a rechargeable battery. An example can include any above example and wherein a third housing contains the electronics and components for receiving charge from the outside of patient's body. An example can include any above example and wherein the three housings are connected together using electrically conductor conduits. An example can include any above example and wherein the battery to power all electronics is contained in one housing and is used to power the electronics in the other housings through the conductive medium used to electrically connect the housings together.

The present examples can execute various methods to provide diagnosis and prepare therapeutic signals within the devices described in any of the above examples. The methods can include a method for treatment of patients with cardiac rhythm irregularities, comprising: implanting a prophylactic device in anticipation of a sudden cardiac death event; monitoring a heart of a patient for episodes of ventricular fibrillation or sudden cardiac arrest; applying defibrillation therapy to the heart in response to a first occurrence of ventricular fibrillation or sudden cardiac arrest; determining, using the cardiac monitoring information, a nature of the irregularities and reason for exhibited ventricular fibrillation or sudden cardiac arrest; extracting the prophylactic device; and implanting a longer term, more permanent, patient specific device. An example can include any above example and wherein the prophylactic device has limited capability and therefore is smaller, less invasive, easier to manage for the physician and cheaper for the healthcare system. An example can include any above example and wherein the prophylactic device is limited to at most 5 years in life for monitoring, applying and determining. An example can include any above example and wherein applying includes limiting life of the prophylactic device to at least one month from applying a first defibrillation therapy. An example can include any above example and wherein monitoring includes continuing monitoring cardiac and episode information to be observed by physician after life of the prophylactic device has expired. An example can include any above example and wherein applying includes limiting life of the prophylactic device to a set number of defibrillation therapies. An example can include any above example and wherein monitoring includes continuing monitoring cardiac and episode information to be observed by physician after life of the prophylactic device has expired. An example can include any above example and wherein the implanting does not perform Defibrillation Threshold Testing ("DFT") testing during implantation. An example can include any above example and wherein the implanting does not include programming controls of the implanted device and does not include a programming function.

An example of an implantable system can include any of the above examples and can comprise electronic system with a housing, a connector that can mate with other systems, an circuitry to receive electrical energy from outside the housing, an electronics to evaluate and communicate with outside the housing, circuitry to generate electrical signal to communicate status with outside the housing. An example can include any above example and wherein the system is developed to mate with a human implantable cardiac arrhythmia treatment devices, such as pacemakers, ICDs, and resynchronization therapy devices. An example can include any above example and wherein the connector can mate with an IS-4 connector in place of a cardiac lead. An example can include any above example and wherein the electronics inside the system has electrical load placed on the input connector at values selectable through the electronic circuitry. An example can include any above example and wherein the indicator is one or more LEDs that communicate status and results to user. An example can include any above example and wherein the indicator is a display, e.g. LCD display, that can communicate messages to the user. An example can include any above example and wherein the system can be used to assess proper operation of an ICD, or pacemaker before it is connected and implanted inside a patient. An example can include any above example and wherein the internal signal generator can be programmed to output signal to imitate heart rhythm to evaluate signal detection capability of the connecting cardiac device. An example can include any above example and The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed, is:

1. A cardiac care, medical system comprising:
   an implantable, medical device housing comprising a header, wherein the header includes a port comprising a probe receptacle and a membrane assembly positioned at an entrance to the probe receptacle, wherein the probe receptacle is configured to receive a probe from outside a body of a patient through the membrane assembly after the housing has been implanted inside the body of the patient, and wherein the probe receptacle comprises multiple, separate conductive segments arranged serially along a longitudinal axis of the probe receptacle and configured to align with corresponding multiple, separate conductive segments arranged serially along a longitudinal axis of the probe when the probe is inserted through the patient's skin and into the probe receptacle; and
   wherein the port is viewable with medical imaging while inside the body of the patient to facilitate guidance and mating of the probe to the port.

2. The medical system of claim 1, wherein the port includes an opaque material that makes it viewable with the medical imaging.

3. The medical system of claim 2, wherein the medical imaging includes X-ray imaging.

4. The medical system of claim 1, wherein the separate conductive segments arranged serially along the longitudinal axis of the probe receptacle comprise one or more contacts configured to provide one or more connections for transmitting communication signals to and/or from the medical system via the corresponding separate conductive segments of the probe when the probe is inserted into the probe receptacle.

5. The medical system of claim 1, wherein the port is configured to receive the probe in electrical isolation from the body of the patient.

6. The medical system of claim 1, wherein the probe receptacle includes one or more seals arranged serially along the longitudinal axis of the probe receptacle and configured to electrically isolate the individual conductive segments of the probe receptacle from each other.

7. The medical system of claim 6, wherein the membrane assembly includes a bodily fluid seal configured to seal the probe receptacle segments from bodily fluid when the probe enters the probe receptacle through the port after piercing the patient's skin.

8. The medical system of claim 7, wherein the bodily fluid seal is adjacent to the entrance to the probe receptacle.

9. The medical system of claim 1, wherein the housing includes a body orientation sensing unit configured to determine a physical orientation of at least a portion of the patient's body and to output orientation data corresponding to the physical orientation of the at least a portion of the patient's body.

10. A medical system comprising:
    an implantable medical device comprising a header, wherein the header includes a port comprising a probe receptacle and a membrane assembly positioned at an entrance to the probe receptacle, wherein the probe receptacle is configured to receive a probe from outside a patient's body through the membrane assembly after the medical device has been implanted inside the body of the patient, and wherein the probe receptacle includes multiple electrically-conductive segments arranged serially along a longitudinal axis of the probe receptacle;
    a probe comprising one or more electrically-conductive segments arranged serially along a longitudinal axis of the probe, and wherein the probe is configured to deliver at least one of energy and data to the medical device from outside of the patient's body after the probe has been inserted into the probe receptacle of the medical device through the port, thereby causing individual electrically-conductive segments of the probe to contact corresponding individual electrically-conductive segments of the probe receptacle; and
    wherein the port is viewable with medical imaging while inside the patient's body to facilitate guidance and mating of the probe to the port.

11. The medical system of claim 10, wherein the probe is configured to mate with the implantable medical device via the port by inserting the probe through the patient's skin and into the probe receptacle after the medical device has been implanted inside the body of the patient.

12. The medical system of claim 11, wherein the multiple electrically-conductive segments of the probe are configured to act as one or more cathode connections and one or more anode connections for energy delivery to the implantable medical device from a power source located outside of the patient's body.

13. The medical system of claim 11, wherein the multiple electrically-conductive segments of the probe are configured to provide one or more connections for transferring communication signals to and/or from the implantable medical device to/from a communications device located outside of the patient's body.

14. The medical system of claim 10, wherein the multiple electrically-conductive segments of the probe are electrically isolated from each other, and wherein the multiple electrically-conductive segments of the probe receptacle are electrically isolated from each other.

15. The medical system of claim 14, wherein the probe has a needle-shape, is smooth along its outer surface, and has a tip to ease penetration of the skin.

16. The medical system of claim 15, wherein the probe includes a smooth outer surface to at least a depth required to penetrate the patient's body to reach and engage a distal end of the probe receptacle.

17. The medical system of claim 14, wherein the probe is tapered from a tip to ease penetration into the patient's body.

18. The medical system of claim 14, wherein the probe includes one or more sets of cathode and anode segments configured to transfer electrical energy into the implantable medical device from a power source located outside of the patient's body, and one or more sets of communications interfaces configured to transmit data to/from the implantable medical device to/from a communications systems located outside of the patient's body.

19. The medical system of claim 18, wherein the membrane assembly positioned at the entrance to the probe receptacle is configured to prevent moisture from leaking into the probe receptacle.

20. The medical system of claim 19, wherein the probe receptacle is generally cylindrical.

21. The medical system of claim 19, wherein each segment of the probe receptacle includes one or more electrical contacts that have mechanical push and make mechanical connection with corresponding segments of the probe when the probe is inserted into the probe receptacle.

22. The medical system of claim 21, where the electrical contacts of the probe receptacle are disabled until the probe is inserted into the probe receptacle to a depth where each electrical contact of the probe receptacle physically engages a corresponding anode or cathode of the probe.

23. The medical system of claim 22, wherein the probe receptacle includes a switch at the distal end of the probe receptacle opposite the entrance to the probe receptacle, wherein the switch is configured to activate the electrical contacts when the probe is inserted into the probe receptacle to a depth where the tip of the probe activates the switch.

24. The medical system of claim 23, wherein the switch holds the electrical contacts of the probe receptacle in a deactive electrical state until the probe is inserted into the probe receptacle to a depth where the tip of the probe activates the switch.

25. The medical system of claim 24, wherein the probe receptacle includes a recess that is essentially cylindrical to form a female connector and the probe includes a male connector configured to mate with the female connector.

26. The medical system of claim 19, wherein the membrane assembly positioned at the entrance to the probe receptacle includes a first layer and a second layer with a fluid between the first and second layers, and wherein the membrane assembly is arranged to prevent material or fluid from the patient's body from entering the probe receptacle.

27. The medical system of claim 26, wherein the membrane assembly is configured to prevent material from inside the probe receptacle from exiting the probe receptacle.

28. The medical system of claim 27, wherein the fluid between the first and second layers of the membrane assembly includes a medical glue that activates upon contact with blood or bodily fluid to close a hole in the membrane assembly left behind by extraction of the probe from the probe receptacle.

29. The medical system of claim 19, where the probe includes an antibiotic coating arranged to protect the patient from possible infections from piercing the patient's skin to insert the probe into the probe receptacle.

30. The medical system of claim 10, wherein the probe is configured to deliver at least one of (i) energy to circuitry within the implantable medical device from a power source located outside of the patient's body or (ii) data to/from circuitry within the implantable medical to/from a communication system located outside of the patient's body.

* * * * *